US011578138B2

(12) United States Patent
Miyake et al.

(10) Patent No.: US 11,578,138 B2
(45) **Date of Patent: *Feb. 14, 2023**

(54) ANTI-HUMAN TLR7 ANTIBODY

(71) Applicants: Daiichi Sankyo Company, Limited, Tokyo (JP); The University of Tokyo, Tokyo (JP)

(72) Inventors: Kensuke Miyake, Tokyo (JP); Yusuke Murakami, Tokyo (JP); Yuji Motoi, Tokyo (JP); Atsuo Kanno, Tokyo (JP); Toshiyuki Shimizu, Tokyo (JP); Umeharu Ohto, Tokyo (JP); Takaichi Shimozato, Tokyo (JP); Atsushi Manno, Tokyo (JP); Takashi Kagari, Tokyo (JP); Jun Ishiguro, Tokyo (JP); Kensuke Nakamura, Tokyo (JP); Takashi Isobe, Tokyo (JP)

(73) Assignees: Daiichi Sankyo Company, Limited, Tokyo (JP); The University of Tokyo, Tokyo (JP)

( * ) Notice: Subject to any disclaimer, the term of this patent is extended or adjusted under 35 U.S.C. 154(b) by 34 days.

This patent is subject to a terminal disclaimer.

(21) Appl. No.: 17/366,820

(22) Filed: Jul. 2, 2021

(65) Prior Publication Data

US 2021/0332149 A1 Oct. 28, 2021

Related U.S. Application Data

(63) Continuation of application No. 17/069,760, filed on Oct. 13, 2020, now Pat. No. 11,091,560, which is a continuation-in-part of application No. PCT/JP2019/021466, filed on May 30, 2019.

(30) Foreign Application Priority Data

May 31, 2018 (JP) ............................ JP2018-104676

(51) Int. Cl.
*C07K 16/28* (2006.01)

(52) U.S. Cl.
CPC ...... *C07K 16/2896* (2013.01); *C07K 2317/24* (2013.01); *C07K 2317/52* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 11,091,560 B2 * | 8/2021 | Miyake .................... | C12N 5/10 |
| 2003/0032090 A1 | 2/2003 | Hardiman et al. | |
| 2016/0185871 A1 | 6/2016 | Miyake et al. | |

FOREIGN PATENT DOCUMENTS

| | | | |
|---|---|---|---|
| EP | 2 990 419 | A1 | 3/2016 |
| JP | 2003533996 | A | 11/2003 |
| WO | 03/080672 | A1 | 10/2003 |
| WO | 2010/054288 | A2 | 5/2010 |
| WO | 2014/174704 | A1 | 10/2014 |
| WO | 2016/201300 | A1 | 12/2016 |
| WO | 2016/210108 | A1 | 12/2016 |
| WO | 2017004144 | A1 | 1/2017 |

OTHER PUBLICATIONS

Search Report and Written Opinion dated May 19, 2022, issued in corresponding Singaporean Application No. 11202010939W, filed May 30, 2019, 8 pages.
"Anti-TLR7 Antibody (4F4): sc-57463," Santa Cruz Biotechnology Inc., 2015, <https://www.scbt.com/p/tlr7-antibody-414>, 11 pages.
"Recombinant Anti-TLR7 antibody [EPR2088(2)] (ab124928)," Abcam plc., 2015, <https://www.abcam.com/tlr7-antibody-epr20882-ab124928.html>, 4 pages.
Filippovich Yu.B. et al, Biochemical foundations of human life, M. Vlados, 2005, p. 49-50, 70.
Yarilin A. A, Fundamentals of Immunology, M. Medicine, 1999, p. 172-173.
Data base GenBank acc. No. BC033651.1, "*Homo sapiens* toll-like receptor 7, mRNA (cDNA clone MGC:45096 IMAGE:5582912), complete cds," Jul. 15, 2006, 3 pages.
Liu, Hongcheng, et al. "In vitro and in vivo modifications of recombinant and human IgG antibodies." MAbs. vol. 6., No. 5. Taylor & Francis, 2014, pp. 1145-1154.
Office Action dated Apr. 22, 2022, issued in corresponding Russian Application No. RU2020140526, filed May 30, 2019, 27 pages.
Christensen, S.R., et al., "Toll-Like Receptor 7 and TLR9 Dictate Autoantibody Specificity and Have Opposing Inflammatory and Regulatory Roles in a Murine Model of Lupus," Immunity 25:417-428, Sep. 2006.
Chuang, T-H. and R.J. Ulevitch, "Cloning and Characterization of a Sub-Family of Human Toll-Like Receptors: hTLR7, hTLR8 and hTLR9," European Cytokine Network 11(3):372-378, Sep. 2000.
International Search Report dated Aug. 27, 2019, issued in corresponding Application No. PCT/JP2019/021466, filed May 30, 2019, 3 pages.
Kanno, A., et al., "Essential Role for Toll-Like Receptor 7 (TLR7)-Unique Cysteines in an Intramolecular Disulfide Bond, Proteolytic Cleavage and RNA Sensing," International Immunology 25 (7):413-422, 2013.
Lyn-Cook, B.D., et al., "Increased Expression of Toll-Like Receptors (TLRs) 7 and 9 and Other Cytokines in Systemic Lupus Erythematosus (SLE) Patients: Ethnic Differences and Potential New Targets for Therapeutic Drugs," Molecular Immunology 61:38-43, 2014.

(Continued)

*Primary Examiner* — Phillip Gambel
(74) *Attorney, Agent, or Firm* — Christensen O'Connor Johnson Kindness PLLC

(57) ABSTRACT

The present invention provides a pharmaceutical composition comprising an antibody which binds specifically to human TLR7 or monkey TLR7 and does not bind to mouse TLR7 or rat TLR7, and has an activity of inhibiting a function of human TLR7 or monkey TLR7, and the like.

39 Claims, 26 Drawing Sheets

Specification includes a Sequence Listing.

(56) References Cited

OTHER PUBLICATIONS

Takeuchi, O., and S. Akira, "Pattern Recognition Receptors and Inflammation," Cell 140:805-820, Mar. 2010.
Rudikoff Stuart, et al., "Single amino acid substitution altering antigen-binding specificity," Proc. Natl. Acad. Sci. USA, Mar. 1982, vol. 79, pp. 1979-1983.
Colman, P. M., "Effects of amino acid sequence changes on antibody-antigen interactions," Research in Immunology, 1994, vol. 145, pp. 33-36.
Kussie, Paul H. et al., "A Single Engineered Amino Acid Substitution Changes Antibody Fine Specificity," Journal of Immunology, 1994, vol. 152, pp. 146-152.
Chen, Ching, et al., "Enhancement and destruction of antibody function by somatic mutation: unequal occurrence is controlled by V gene combinatorial associations," The EMBO Journal, 1995, vol. 14, No. 12, pp. 2784-2794.
D'Angelo, Sara, et al., "Many Many Routes to an Antibody Heavy-Chain CDR3: Necessary, Yet Insufficient, for Specific Binding," Frontiers in Immunology, Mar. 2018, vol. 9, Article 395, pp. 1-13.
Piche-Nicholas, Nicole M. et al., Changes in complementarity-determining regions significantly after IgG binding to the neonatal Fc receptor (FcRn) and pharmacokinetics, MABS, 2018, vol. 10, No. 1, pp. 81-94.
Hennessy, Elizabeth J. et al., "Targeting Toll-like Receptors: Emerging Therapeutics?," Nature Reviews / Drug Discovery, Apr. 2010, vol. 9, pp. 293-307.
Tamura, M., et al., "Structural Correlates of an Anticarcinoma Antibody: Identification of Specificity-Determining Residues (SDRs) and Development of a Minimally Immunogenic Antibody Variant by Retention of SDRs Only," The Journal of Immunology 164:1432-1441, Feb. 2000.
Office Action dated Dec. 9, 2021, issued in corresponding Canadian Application No. 3,099,900, filed Nov. 10, 2020, 7 pages.
Written Opinion dated Aug. 27, 2019, issued in corresponding International Patent Application No. PCT/JP2019/021466, filed May 30, 2019, 12 pages.
Extended European Search Report dated Feb. 18, 2022, issued in corresponding European Patent Application No. 19811934.9, filed May 30, 2019, 13 pages.
N.N.: "Human TLR7 Antibody: Monoclonal Mouse IgG2A Clone #533707," R&D Systems Product Catalogue No. MAB5875. Oct. 13, 2015, <https://resources.rndsystems.com/pdfs/datasheets/mab5875.pdf> [Retrieved Nov. 30, 2016], whole document.
N.N.:"Idera Pharmaceuticals Announces Positive Top-Line Results From Phase 2 Trial of IMO-3100 in Patients With Moderate-to-Severe Plaque Psoriasis," Idera Press Release. Dec. 19, 2012, <http://ir.iderapharma.com/phoenix.zhtml?c=208904&p=irol-newsArticle_print&ID=1768483> [Retrieved Dec. 1, 2016], whole document.
Wu, Y-W., et al., "Toll-Like Receptors: Potential Targets for Lupus Treatment," Acta Pharmacologica Sinica 36(12):1395-1407, Dec. 1, 2015.

* cited by examiner

Figure 1

Amino acid sequence (SEQ ID NO: 2) of human TLR7 (variant 1)

mvfpmwtlkrqililfniiliskllgarwfpktlpcdvtldvpknhvivdctdkhlt
eipggiptnttnltltinhipdispasfhrldhlveidfrcncvpiplgsknnmcik
rlqikprsfsgltylkslyldgnqlleipqglppslqllsleannifsirkenltel
anieilylgqncyyrnpcyvsysiekdaflnltklkvlslkdnnvtavptvlpstlt
elylynnmiakiqeddfnnlnqlqildlsgncprcynapfpcapcknnsplqipvna
fdaltelkvlrlhsnslqhvpprwfkninklqeldlsqnflakeigdakflhflpsl
iqldlsfnfelqvyrasmnlsqafsslkslkilrirgyvfkelksfnlsplhnlqnl
evldlgtnfikianlsmfkqfkrlkvidlsvnkispsgdssevgfcsnartsvesye
pqvleqlhyfrydkyarscrfknkeasfmsvnescykygqtldlsknsiffvkssdf
qhlsflkclnlsgnlisqtlngsefqplaelryldfsnnrldllhstafeelhklev
ldissnshyfqsegithmlnftknlkvlqklmmndndissstsrtmeseslrtlefr
gnhldvlwregdnrylqlfknllkleeldisknslsflpsgvfdgmppnlknlslak
nglksfswkklqclknletldlshnqlttvperlsncsrslknlilknnqirsltky
flqdafqlryldlssnkiqmiqktsfpenvlnnlkmlllhhnrflctcdavwfvwwv
nhtevtipylatdvtcvgpgahkgqsvisldlytceldltnlilfslsisvslflmv
mmtashlyfwdvwyiyhfckakikgyqrlispdccydafivydtkdpavtewvlael
vakledprekhfnlcleerdwlpgqpvlenlsqsiqlskktvfvmtdkyaktenfki
afylshqrlmdekvdviiliflekpfqkskflqlrkrlcgssvlewptnpqahpyfw
qclknalatdnhvaysqvfketv

Figure 2

Amino acid sequence (SEQ ID NO: 4) of human TLR7 (variant 2)

mvfpmwtlkrqililfniiliskllgarwfpktlpcdvtldvpknhvivdctdkhlt
eipggiptnttnltltinhipdispasfhrldhlveidfrcncvpiplgsknnmcik
rlqikprsfsgltylkslyldgnqlleipqglppslqllsleannifsirkenltel
anieilylgqncyyrnpcyvsysiekdaflnltklkvlslkdnnvtavptvlpstlt
elylynnmiakiqeddfnnlnqlqildlsgncprcynapfpcapcknnsplqipvna
fdaltelkvlrlhsnslqhvpprwfkninklqeldlsqnflakeigdakflhflpsl
iqldlsfnfelqvyrasmnlsqafsslkslkilrirgyvfkelksfnlsplhnlqnl
evldlgtnfikianlsmfkqfkrlkvidlsvnkispsgdssevgfcsnartsvesye
pqvleqlhyfrydkyarscrfknkeasfmsvnescykygqtldlsknsiffvkssdf
qhlsflkclnlsgnlisqtlngsefqplaelryldfsnnrldllhstafeelhklev
ldissnshyfqsegithmlnftknlkvlqklmmndndissstsrtmeseslrtlefr
gnhldvlwregdnrylqlfknllkleeldisknslsflpsgvfdgmppnlknlslak
nglksfswkklqclknletldlshnqlttvperlsncsrshknlilknnqirsptky
flqdafqlryldlssnkiqmiqktsfpenvlnnlkmlllhhnrflctcdavwfvwwv
nhtevtipylatdvtcvgpgahkgqsvisldlytceldltnlilfslsisvslflmv
mmtashlyfwdvwyiyhfckakikgyqrlispdccydafivydtkdpavtewvlael
vakledprekhfnlcleerdwlpgqpvlenlsqsiqlskktvfvmtdkyaktenfki
afylshqrlmdekvdviiliflekpfqkskflqlrkrlcgssvlewptnpqahpyfw
qclknalatdnhvaysqvfketv

Figure 3

Amino acid sequence (SEQ ID NO: 83) of mouse TLR7 mvfsmwtrkrqiliflnmllvsrvfgfrwfpktlpcevkvnipeahvivdctdkhlt eipegiptnttnltltinhipsispdsfrrlnhleeidlrcncvpvllgskanvctk rlqirpgsfsglsdlkalyldgnqlleipqdlpsslhllsleannifsitkenltel vnietlylgqncyyrnpcnvsysiekdaflvmrnlkvlslkdnnvtavpttlppnll elylynniikkiqendfnnlnelqvldlsgncprcynvpypctpcennsplqihdna fnsltelkvlrlhsnslqhvpptwfknmrnlqeldlsqnylareieeakflhflpnl veldfsfnyelqvyhasitlphslsslenlkilrvkgyvfkelknsslsvlhklprl evldlgtnfikiadlnifkhfenlklidlsvnkispseesrevgfcpnaqtsvdrhg pqvlealhyfrydeyarscrfknkeppsflplnadchiygqtldlsrnniffikpsd fqhlsflkclnlsgntigqtlngselwplrelryldfsnnrldllystafeelqsle vldlssnshyfqaegithmlnftkklrlldklmmndndistsasrtmesdslrilef rgnhldvlwragdnryldffknlfnlevldisrnslnslppevfegmppnlknlsla knglksffwdrlqllkhleildlshnqltkvperlancskslttlilkhnqirqltk yfledalqlryldissnkiqviqktsfpenvlnnlemlvlhhnrflcncdavwfvww vnhtdvtipylatdvtcvgpgahkgqsvisldlytceldltnlilfsvsissvlflm vvmttshlffwdmwyiyyfwkakikgyqhlqsmescydafivydtknsavtewvlqe lvakledprekhfnlcleerdwlpgqpvlenlsqsiqlskktvfvmtqkyaktesfk mafylshqrlldekvdviiliflekplqkskflqlrkrlcrssvlewpanpqahpyf wqclknalttdnhvaysqmfketv

Figure 4

Amino acid sequence (SEQ ID NO: 84) of rat TLR7 mvfpmwtlkrqsfiflnmilvsrvlgfrwypktlpcdvsldstnthvivdctdkhlt
eipegiptnttnltltinhipsispdsfhrlkhleeldlrcncvpillgskanvctk
rlqirpgsfsglsdlkslyldgnqlleipqdlpsslqllsleannifsitkenlsel
vnieslylgqncyyrnpcnvsysiekdaflvmknlkvlslkdnnvtavptilppnll
elylynniikriqehdfnklsqlqvldlsgncprcynvpypctpcennsplqihdna
fdsltelkvlrlhsnslqhvpaewfknmsnlqeldlsqnylareieeakflnslpnl
vqldlsfnyelqvyhasitlphslssltklknlyikgyvfkelkdsslsvlhnlsnl
evldlgtnfikiadlnifqqfenlkfidlsvnkispseesrevglcpnaqtsvdwhg
pqvlealhyfrydeyarscrfknkepptflplnadchtygktldlsrnniffikpsd
fkhlsflkclnlsgnaigqtlngselqplrelryldfsnnrldllystafeelqnle
ildlssnshyfqaegithmlnftkklrhleklmmndndistsasrtmeseslrvlef
rgnhldvlwrdgdnryldffknllnleeldisrnslnsvppgvfegmppnlttlsla
knglrsfswgrlqllkhlknldlshnqlttvparlancsksltklilnhnqirqltk
yfledalqlryldissnkiqviqktsfpenvlnnlnmlllhhnrflcncdavwfvww
vnhtdvtipylatdvtcagpgahkgqsvisldlytceldltnlilfsvsissvlflm
ivmttshlffwdmwyiyyfwkakikgyqhlqsmescydafivydtknsavtewvlqe
lvvkledprekhfnlcleerdwlpgqpvlenlsqsiqlsrktvfvmtqkyaktesfk
mafylshqrlmdekvdviiliflekplqkskflqlrkrlcsssvlewptnpqahpyf
wqclknalttdnhvaysqmfketv

Figure 5

Amino acid sequence (SEQ ID NO: 85) of monkey TLR7 mmfpvwtlkrqililfniiliskllgarwfpktlpcdvtldvsknhvivdctdkhlt
eipggiptnttnltltinhipdispasfhrlvhlveidfrcncvpirlgsksnmcpr
rlqikprsfsgltylkslyldgnqlleipgglppslqllsleannifsirkenltel
anieilylgqncyyrnpcyvsysiekdaflnltklkvlslkdnnvttvptvlpstlt
elylynnmiaeiqeddfnnlnqlqildlsgncprcynapfpctpcknnsplqipvna
fdaltelkvlrlhsnslqhvpprwfkninnlqeldlsqnflakeigdakflhflpnl
iqldlsfnfelqvyrasmnlsqafsslkslkilrirgyvfkelksfnlsplhnlqnl
evldlgtnfikianlsmfkqfkrlkvidlsvnkispsgdssevgfcsnartsvesye
pqvleqlyyfrydkyarscrfknkeasftsvnescykygqtldlsknsiffikssdf
qhlsflkclnlsgnlisqtlngsefqplaelryldfsnnrldllhstafeelrklev
ldissnshyfqsegithmlnftknlkvlqklmmndndissstsrtmeseslrtlefr
gnhldvlwrdgdnrylqlfknllkleeldisknslsflpsgvfdgmppnlknlslak
nglksfiweklrylknletldlshnqlttvperlsncsrslknlilknnqirsltky
flqdafqlryldlssnkiqmiqktsfpenvlnnlkmlllhhnrflctcdavwfvwwv
nhtevtipylatdvtcvgpgahkgqsvisldlytceldltnlilfslsisvslflmv
mmtashlyfwdvwyiyhfckakikgyqrlispdccydafivydtkdpavtewvlael
vakledprekhfnlcleerdwlpgqpvlenlsqsiqlskktvfvmtdkyaktenfki
afylshqrlmdekvdviiliflekpfqkskflqlrkrlcgssvlewptnpqahpyfw
qclknalatdnhvaysqvfketv

Figure 7

Amino acid sequence (SEQ ID NO: 35) of heavy chain (including signal sequence thereof) of cAT01 antibody and amino acid sequence (SEQ ID NO: 36) of light chain (including signal sequence thereof)

MKHLWFFLLLVAAPRWVLSQVQLQQPGAELVKPGASVNLSCKASGYTFTNNWLHWVK
QRPGRGLEWIGDIYPSNGRTNYNEQFKTKATLTVDKSSSTAYMQLSSLTSEDSAVYF
CARERGYFDYWGQGTALTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK (SEQ ID NO: 35)

MVLQTQVFISLLLWISGAYGDIQMTQSPSSLSTSLGGKVTITCKASQDINKYIAWYQ
HKPGKGPRLLIHYTSTLQPGIPSRFSGSGSGRDYSFSISNLEPEDIATYYCLQYDYL
LTFGAGTKLELKRAVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC (SEQ ID NO: 36)

Figure 8

Amino acid sequence (SEQ ID NO: 37) of heavy chain (including signal sequence thereof) of cNB7 antibody and amino acid sequence (SEQ ID NO: 38) of light chain (including signal sequence thereof)

MKHLWFFLLLVAAPRWVLSDVQLQESGPGLVKPSQSLSLTCTVTGYSITSDYAWNWI
RQFPGNKLEWMGHISYRGNTNYNPSLKSRISITRDTSKNQFFLQLNSVTTEDTATYY
CASWNYYGYVDYAMDYWGQGTSVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKRVEPKSCDKTHTCPPCPAPELLGGPSVFLFPPKPKDTLMISRTPEVTC
VVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEAL
HNHYTQKSLSLSPGK (SEQ ID NO: 37)

MVLQTQVFISLLLWISGAYGDIQMTQTPSSLSASLGDRVTISCRASQDISNYLNWYQ
QKPDGTVKLLIYYTSRLHSGVPSRFSGSGSGTDYSLTINNLEQEDIATYFCQQGDTF
PTFGGGTKLEIKRAVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC (SEQ ID NO: 38)

Figure 9

Amino acid sequence (SEQ ID NO: 39) of heavy chain (including signal sequence thereof) of cFAN2 antibody and amino acid sequence (SEQ ID NO: 40) of light chain (including signal sequence thereof)

MKHLWFFLLLVAAPRWVLSQVQLKESGPGLVAPSQSLSITCTVSGFSLTGYGVNWVR
QPPGKGLEWLGMIWGDGSTDYNSALKSRLSIRKDNSKSQVFLKMNSLQTDDTARYYC
ARDKGYDGYYYAMDYWGQGTSVTVSSASTKGPSVFPLAPSSKSTSGGTAALGCLVKD
YFPEPVTVSWNSGALTSGVHTFPAVLQSSGLYSLSSVVTVPSSSLGTQTYICNVNHK
PSNTKVDKRVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCLVKGFYPSD
IAVEWESNGQPENNYKTTPPVLDSDGSFFLYSKLTVDKSRWQQGNVFSCSVMHEALH
NHYTQKSLSLSPGK (SEQ ID NO: 39)

MVLQTQVFISLLLWISGAYGDIQMTQSPASLSASVGETVTITCRASENIYSYLAWYQ
QKQGKSPQLLVYDAKTLAEGVPSRFSGSGSGTQFSLKINSLQPEDFGSYYCQHHYGI
PYTFGGGTKLEIKRAVAAPSVFIFPPSDEQLKSGTASVVCLLNNFYPREAKVQWKVD
NALQSGNSQESVTEQDSKDSTYSLSSTLTLSKADYEKHKVYACEVTHQGLSSPVTKS
FNRGEC (SEQ ID NO: 40)

Figure 11

Amino acid sequence (SEQ ID NO: 45) (including signal sequence) of humanized heavy chain huAT01_H1_IgG1LALA MKHLWFFLLLVAAPRWVLSQVQLVQSGAEVKKPGASVKVSCKASGYTFTNNWLHWVR
QAPGQGLEWMGDIYPSNGRTNYAQKFQGRVTITADKSTSTAYMELSSLRSEDTAVYY
CARERGYFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK

Figure 12

Amino acid sequence (SEQ ID NO: 46) (including signal sequence) of humanized heavy chain huAT01_H3_IgG1LALA MKHLWFFLLLVAAPRWVLSQVQLVQSGAEVKKPGASVKVSCKASGYTFTNNWLHWVR
QAPGQGLEWMGDIYPSNGRTNYAQKFQGRVTLTVDKSTSTAYMELSSLRSEDTAVYF
CARERGYFDYWGQGTLVTVSSASTKGPSVFPLAPSSKSTSGGTAALGCLVKDYFPEP
VTVSWNSGALTSGVHTFPAVLQSSGLYSLSSVVTVPSSSLGTQTYICNVNHKPSNTK
VDKRVEPKSCDKTHTCPPCPAPEAAGGPSVFLFPPKPKDTLMISRTPEVTCVVVDVS
HEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQ
KSLSLSPGK

Figure 13

Amino acid sequence (SEQ ID NO: 47) (including signal sequence) of humanized heavy chain huAT01_H3_IgG4Pro MKHLWFFLLLVAAPRWVLSQVQLVQSGAEVKKPGASVKVSCKASGYTFTNNWLHWVR
QAPGQGLEWMGDIYPSNGRTNYAQKFQGRVTLTVDKSTSTAYMELSSLRSEDTAVYF
CARERGYFDYWGQGTLVTVSSASTKGPSVFPLAPCSRSTSESTAALGCLVKDYFPEP
VTVSWNSGALTSGVHTFPAVLQSSGLYSLSSVVTVPSSSLGTKTYTCNVDHKPSNTK
VDKRVESKYGPPCPPCPAPEFLGGPSVFLFPPKPKDTLMISRTPEVTCVVVDVSQED
PEVQFNWYVDGVEVHNAKTKPREEQFNSTYRVVSVLTVLHQDWLNGKEYKCKVSNKG
LPSSIEKTISKAKGQPREPQVYTLPPSQEEMTKNQVSLTCLVKGFYPSDIAVEWESN
GQPENNYKTTPPVLDSDGSFFLYSRLTVDKSRWQEGNVFSCSVMHEALHNHYTQKSL
SLSLGK

Figure 14

```
cbAT01_H     1 QVQLQQPGAELVKPGASVNLSCKASGYTFTNNWLHWVKQRPGRGLEWIGDIYPSNGRTNY 60
huAT01_H1    1 ....V.S...VK......KV.................R.A..Q....M............ 60
huAT01_H3    1 ....V.S...VK......KV.................R.A..Q....M............ 60

cbAT01_H    61 NEQFKTKATLTVDKSSSTAYMQLSSLTSEDSAVYFCARERGYFDYWGQGTALTVSS     116
huAT01_H1   61 AQK.QGRV.I.A...T....E...R..T..Y...................LV....     116
huAT01_H3   61 AQK.QGRV.......T....E...R..T......................LV....     116
```

Figure 15

Amino acid sequence (SEQ ID NO: 48) (including signal sequence) of humanized light chain huAT01_L1

MVLQTQVFISLLLWISGAYGDIQMTQSPSSLSASVGDRVTITCKASQDINKYIAWYQ
QKPGKAPKLLIHYTSTLQPGVPSRFSGSGSGRDFTLTISSLQPEDFATYYCLQYDYL
LTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC

Figure 16

Amino acid sequence (SEQ ID NO: 49) (including signal sequence) of humanized light chain huAT01_L2

MVLQTQVFISLLLWISGAYGDIQMTQSPSSLSASVGDRVTITCKASQDINKYIAWYQ
QKPGKAPKLLIHYTSTLQPGIPSRFSGSGSGRDYTLTISSLQPEDFATYYCLQYDYL
LTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC

Figure 17

```
chAT01_L    1 DIQMTQSPSSLSTSLGGKVTITCKASQDINKYIAWYQHKPGKGPRLLIHYTSTLQPGIPS 60
huAT01_L1   1 ............A.V.DR...................Q....A.K............V.. 60
huAT01_L2   1 ............A.V.DR...................Q....A.K............... 60

chAT01_L   61 RFSGSGSGRDYSFSISNLEPEDIATYYCLQYDYLLTFGAGTKLELK               106
huAT01_L1  61 ..........FTLT..S.Q...F...............Q...V.I.               106
huAT01_L2  61 ...........TLT..S.Q...F...............Q...V.I.               106
```

Figure 18

Amino acid sequence (SEQ ID NO: 52) (including signal sequence) of humanized heavy chain huNB7_H3_IgG1LALA MKHLWFFLLLVAAPRWVLSDVQLQESGPGLVKPSDTLSLTCTVTGYSITSDYAWNWI
RQPPGNKLEWIGHISYRGNTNYNPSLKSRVTISRDTSKNQFSLKLSSVTAADTAVYY
CASWNYYGYVDYAMDYWGQGTTVTVSSASTKGPSVFPLAPSSKSTSGGTAALGCLVK
DYFPEPVTVSWNSGALTSGVHTFPAVLQSSGLYSLSSVVTVPSSSLGTQTYICNVNH
KPSNTKVDKRVEPKSCDKTHTCPPCPAPEAAGGPSVFLFPPKPKDTLMISRTPEVTC
VVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEAL
HNHYTQKSLSLSPGK

Figure 19

Amino acid sequence (SEQ ID NO: 54) (including signal sequence) of humanized heavy chain huNB7_H3_IgG4Pro

```
MKHLWFFLLLVAAPRWVLSDVQLQESGPGLVKPSDTLSLTCTVTGYSITSDYAWNWI
RQPPGNKLEWIGHISYRGNTNYNPSLKSRVTISRDTSKNQFSLKLSSVTAADTAVYY
CASWNYYGYVDYAMDYWGQGTTVTVSSASTKGPSVFPLAPCSRSTSESTAALGCLVK
DYFPEPVTVSWNSGALTSGVHTFPAVLQSSGLYSLSSVVTVPSSSLGTKTYTCNVDH
KPSNTKVDKRVESKYGPPCPPCPAPEFLGGPSVFLFPPKPKDTLMISRTPEVTCVVV
DVSQEDPEVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKGFYPSDIA
VEWESNGQPENNYKTTPPVLDSDGSFFLYSRLTVDKSRWQEGNVFSCSVMHEALHNH
YTQKSLSLSLGK
```

Figure 20

```
chNB7_H     1 DVQLQESGPGLVKPSQSLSLTCTVTGYSITSDYAWNWIRQFPGNKLEWMGHISYRGNTNY  60
huNB7_H3    1 ...............DT.......................P.......I...........  60

chNB7_H    61 NPSLKSRISITRDTSKNQFFLQLNSVTTEDTATYYCASWNYYGYVDYAMDYWGQGTSVTV 120
huNB7_H3   61 .......VT.S........S.K.S...AA...V.......................T... 120

chNB7_H   121 SS                                                           122
huNB7_H3  121 ..                                                           122
```

Figure 21

Amino acid sequence (SEQ ID NO: 53) (including signal sequence) of humanized light chain huNB7_L3

```
MVLQTQVFISLLLWISGAYGDIQMTQSPSSLSASVGDRVTITCRASQDISNYLNWYQ
QKPGKAVKLLIYYTSRLHSGVPSRFSGSGSGTDYTLTISSLQPEDFATYFCQQGDTF
PTFGQGTKVEIKRTVAAPSVFIFPPSDEQLKSGTASVVCLLNNFYPREAKVQWKVDN
ALQSGNSQESVTEQDSKDSTYSLSSTLTLSKADYEKHKVYACEVTHQGLSSPVTKSF
NRGEC
```

Figure 22

```
chNB7_L    1 DIQMTQTPSSLSASLGDRVTISCRASQDISNYLNWYQQKPDGTVKLLIYYTSRLHSGVPS 60
huNB7_L3   1 ......S.......V......T..................GKA................. 60

chNB7_L   61 RFSGSGSGTDYSLTINNLEQEDIATYFCQQGDTFPTFGGGTKLEIK               106
huNB7_L3  61 ...........T...SS.QP..F...............Q...V...               106
```

Amino acid sequence of CDRs of the AT01 antibody

Amino acid sequence (SEQ ID NO: 17) of CDRH1: GYTFTNNWLH

Amino acid sequence (SEQ ID NO: 18) of CDRH2: DIYPSNGRTN

Amino acid sequence (SEQ ID NO: 19) of CDRH3: ERGYFDY

Amino acid sequence (SEQ ID NO: 20) of CDRL1: KASQDINKYIA

Amino acid sequence (SEQ ID NO: 21) of CDRL2: YTSTLQP

Amino acid sequence (SEQ ID NO: 22) of CDRL3: LQYDYLLT

Figure 24-2

Amino acid sequence of CDRs of the NB7 antibody

Amino acid sequence (SEQ ID NO: 23) of CDRH1: GYSITSDYAWN

Amino acid sequence (SEQ ID NO: 24) of CDRH2: HISYRGNTN

Amino acid sequence (SEQ ID NO: 25) of CDRH3:

WNYYGYVDYAMDY

Amino acid sequence (SEQ ID NO: 26) of CDRL1: RASQDISNYLN

Amino acid sequence (SEQ ID NO: 27) of CDRL2: YTSRLHS

Amino acid sequence (SEQ ID NO: 28) of CDRL3: QQGDTFPT

Figure 24-3

Amino acid sequence of CDRs of the FAN2 antibody

Amino acid sequence (SEQ ID NO: 29) of CDRH1: GFSLTGYGVN

Amino acid sequence (SEQ ID NO: 30) of CDRH2: MIWGDGSTD

Amino acid sequence (SEQ ID NO: 31) of CDRH3:

DKGYDGYYYAMDY

Amino acid sequence (SEQ ID NO: 32) of CDRL1: RASENIYSYLA

Amino acid sequence (SEQ ID NO: 33) of CDRL2: DAKTLAE

Amino acid sequence (SEQ ID NO: 34) of CDRL3: QHHYGIPYT

SEQUENCE LISTING

<160> NUMBER OF SEQ ID NOS: 87

<210> SEQ ID NO 1
<211> LENGTH: 3150
<212> TYPE: DNA
<213> ORGANISM: Homo sapiens

<400> SEQUENCE: 1
atggtgtttc caatgtggac actgaagaga caaattctta tcctttttaa cataatccta 60
atttccaaac tccttggggc tagatggttt cctaaaactc tgccctgtga tgtcactctg 120
gatgttccaa agaaccatgt gatcgtggac tgcacagaca agcatttgac agaaattcct 180
ggaggtattc ccacgaacac cacgaacctc accctcacca ttaaccacat accagacatc 240
tccccagcgt cctttcacag actggaccat ctggtagaga tcgatttcag atgcaactgt 300
gtacctattc cactggggtc aaaaaacaac atgtgcatca agaggctgca gattaaaccc 360
agaagcttta gtggactcac ttatttaaaa tccctttacc tggatggaaa ccagctacta 420
gagataccgc agggcctccc gcctagctta cagcttctca gccttgaggc caacaacatc 480
ttttccatca gaaaagagaa tctaacagaa ctggccaaca tagaaatact ctacctgggc 540
caaaactgtt attatcgaaa tccttgttat gtttcatatt caatagagaa agatgccttc 600
ctaaacttga caaagttaaa agtgctctcc ctgaaagata acaatgtcac agccgtccct 660
actgttttgc catctacttt aacagaacta tatctctaca acaacatgat tgcaaaaatc 720
caagaagatg attttaataa cctcaaccaa ttacaaattc ttgacctaag tggaaattgc 780
cctcgttgtt ataatgcccc atttccttgt gcgccgtgta aaaataattc tcccctacag 840
atccctgtaa atgcttttga tgcgctgaca gaattaaaag ttttacgtct acacagtaac 900
tctcttcagc atgtgccccc aagatggttt aagaacatca acaaactcca ggaactggat 960
ctgtcccaaa acttcttggc caaagaaatt ggggatgcta aatttctgca ttttctcccc 1020
agcctcatcc aattggatct gtctttcaat tttgaacttc aggtctatcg tgcatctatg 1080
aatctatcac aagcattttc ttcactgaaa agcctgaaaa ttctgcggat cagaggatat 1140
gtctttaaag agttgaaaag ctttaacctc tcgccattac ataatcttca aaatcttgaa 1200
gttcttgatc ttggcactaa ctttataaaa attgctaacc tcagcatgtt taaacaattt 1260
aaaagactga aagtcataga tctttcagtg aataaaatat caccttcagg agattcaagt 1320
gaagttggct tctgctcaaa tgccagaact tctgtagaaa gttatgaacc ccaggtcctg 1380
gaacaattac attatttcag atatgataag tatgcaagga gttgcagatt caaaaacaaa 1440
gaggcttctt tcatgtctgt taatgaaagc tgctacaagt atgggcagac cttggatcta 1500
agtaaaaata gtatattttt tgtcaagtcc tctgattttc agcatctttc tttcctcaaa 1560
tgcctgaatc tgtcaggaaa tctcattagc caaactctta atggcagtga attccaacct 1620
ttagcagagc tgagatattt ggacttctcc aacaaccggc ttgatttact ccattcaaca 1680
gcatttgaag agcttcacaa actggaagtt ctggatataa gcagtaatag ccattatttt 1740
caatcagaag gaattactca tatgctaaac tttaccaaga acctaaaggt tctgcagaaa 1800
ctgatgatga acgacaatga catctcttcc tccaccagca ggaccatgga gagtgagtct 1860
cttagaactc tggaattcag aggaaatcac ttagatgttt tatggagaga aggtgataac 1920
agatacttac aattattcaa gaatctgcta aaattagagg aattagacat ctctaaaaat 1980
tccctaagtt tcttgccttc tggagttttt gatggtatgc ctccaaatct aaagaatctc 2040
tctttggcca aaaatgggct caaatctttc agttggaaga aactccagtg tctaaagaac 2100

-continued

```
ctggaaactt tggacctcag ccacaaccaa ctgaccactg tccctgagag attatccaac   2160

tgttccagaa gcctcaagaa tctgattctt aagaataatc aaatcaggag tctgacgaag   2220

tattttctac aagatgcctt ccagttgcga tatctggatc tcagctcaaa taaaatccag   2280

atgatccaaa agaccagctt cccagaaaat gtcctcaaca atctgaagat gttgcttttg   2340

catcataatc ggtttctgtg cacctgtgat gctgtgtggt ttgtctggtg ggttaaccat   2400

acggaggtga ctattcctta cctggccaca gatgtgactt gtgtggggcc aggagcacac   2460

aagggccaaa gtgtgatctc cctggatctg tacacctgtg agttagatct gactaacctg   2520

attctgttct cactttccat atctgtatct ctctttctca tggtgatgat gacagcaagt   2580

cacctctatt tctgggatgt gtggtatatt taccatttct gtaaggccaa gataaagggg   2640

tatcagcgtc taatatcacc agactgttgc tatgatgctt ttattgtgta tgacactaaa   2700

gacccagctg tgaccgagtg ggttttggct gagctggtgg ccaaactgga agacccaaga   2760

gagaaacatt ttaatttatg tctcgaggaa agggactggt taccagggca gccagttctg   2820

gaaaaccttt cccagagcat acagcttagc aaaaagacag tgtttgtgat gacagacaag   2880

tatgcaaaga ctgaaaattt taagatagca ttttacttgt cccatcagag gctcatggat   2940

gaaaaagttg atgtgattat cttgatattt cttgagaagc cctttcagaa gtccaagttc   3000

ctccagctcc ggaaaaggct ctgtgggagt tctgtccttg agtggccaac aaacccgcaa   3060

gctcacccat acttctggca gtgtctaaag aacgccctgg ccacagacaa tcatgtggcc   3120

tatagtcagg tgttcaagga aacggtctag                                    3150
```

<210> SEQ ID NO 2
<211> LENGTH: 1049
<212> TYPE: PRT
<213> ORGANISM: Homo sapiens

<400> SEQUENCE: 2

```
Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160

Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190
```

-continued

```
Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605
```

-continued

```
Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
    690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe  Leu Gln Leu Arg Lys  Arg Leu Cys
        995                 1000                1005

Gly Ser  Ser Val Leu Glu Trp  Pro Thr Asn Pro Gln  Ala His Pro
    1010                1015                1020
```

-continued

```
Tyr Phe  Trp Gln Cys Leu Lys  Asn Ala Leu Ala Thr  Asp Asn His
    1025                1030                1035

Val Ala  Tyr Ser Gln Val Phe  Lys Glu Thr Val
    1040                1045
```

<210> SEQ ID NO 3
<211> LENGTH: 3150
<212> TYPE: DNA
<213> ORGANISM: Homo sapiens

<400> SEQUENCE: 3

```
atggtgtttc caatgtggac actgaagaga caaattctta tcctttttaa cataatccta     60

atttccaaac tccttggggc tagatggttt cctaaaactc tgccctgtga tgtcactctg    120

gatgttccaa agaaccatgt gatcgtggac tgcacagaca agcatttgac agaaattcct    180

ggaggtattc ccacgaacac cacgaacctc accctcacca ttaaccacat accagacatc    240

tccccagcgt cctttcacag actggaccat ctggtagaga tcgatttcag atgcaactgt    300

gtacctattc cactggggtc aaaaaacaac atgtgcatca agaggctgca gattaaaccc    360

agaagcttta gtggactcac ttatttaaaa tccctttacc tggatggaaa ccagctacta    420

gagataccgc agggcctccc gcctagctta cagcttctca gccttgaggc caacaacatc    480

ttttccatca gaaaagagaa tctaacagaa ctggccaaca tagaaatact ctacctgggc    540

caaaactgtt attatcgaaa tccttgttat gtttcatatt caatagagaa agatgccttc    600

ctaaacttga caaagttaaa agtgctctcc ctgaaagata acaatgtcac agccgtccct    660

actgttttgc catctacttt aacagaacta tatctctaca acaacatgat tgcaaaaatc    720

caagaagatg attttaataa cctcaaccaa ttacaaattc ttgacctaag tggaaattgc    780

cctcgttgtt ataatgcccc atttccttgt gcgccgtgta aaaataattc tcccctacag    840

atccctgtaa atgcttttga tgcgctgaca gaattaaaag ttttacgtct acacagtaac    900

tctcttcagc atgtgccccc aagatggttt aagaacatca acaaactcca ggaactggat    960

ctgtcccaaa acttcttggc caaagaaatt ggggatgcta aatttctgca ttttctcccc   1020

agcctcatcc aattggatct gtctttcaat tttgaacttc aggtctatcg tgcatctatg   1080

aatctatcac aagcattttc ttcactgaaa agcctgaaaa ttctgcggat cagaggatat   1140

gtctttaaag agttgaaaag ctttaacctc tcgccattac ataatcttca aaatcttgaa   1200

gttcttgatc ttggcactaa ctttataaaa attgctaacc tcagcatgtt taaacaattt   1260

aaaagactga aagtcataga tctttcagtg aataaaatat caccttcagg agattcaagt   1320

gaagttggct tctgctcaaa tgccagaact tctgtagaaa gttatgaacc ccaggtcctg   1380

gaacaattac attatttcag atatgataag tatgcaagga gttgcagatt caaaaacaaa   1440

gaggcttctt tcatgtctgt taatgaaagc tgctacaagt atgggcagac cttggatcta   1500

agtaaaaata gtatattttt tgtcaagtcc tctgattttc agcatctttc tttcctcaaa   1560

tgcctgaatc tgtcaggaaa tctcattagc caaactctta atggcagtga attccaacct   1620

ttagcagagt tgagatattt ggacttctcc aacaaccggc ttgatttact ccattcaaca   1680

gcatttgaag agcttcacaa actggaagtt ctggatataa gcagtaatag ccattatttt   1740

caatcagaag gaattactca tatgctaaac tttaccaaga acctaaaggt tctgcagaaa   1800

ctgatgatga acgacaatga catctcttcc tccaccagca ggaccatgga gagtgagtct   1860

cttagaactc tggaattcag aggaaatcac ttagatgttt tatggagaga aggtgataac   1920

agatacttac aattattcaa gaatctgcta aaattagagg aattagacat ctctaaaaat   1980
```

```
tccctaagtt tcttgccttc tggagttttt gatggtatgc ctccaaatct aaagaatctc   2040

tctttggcca aaaatgggct caaatctttc agttggaaga aactccagtg tctaaagaac   2100

ctggaaactt tggacctcag ccacaaccaa ctgaccactg tccctgagag attatccaac   2160

tgttccagaa gccacaagaa tctgattctt aagaataatc aaatcaggag tccgacgaag   2220

tattttctac aagatgcctt ccagttgcga tatctggatc tcagctcaaa taaaatccag   2280

atgatccaaa agaccagctt cccagaaaat gtcctcaaca atctgaagat gttgcttttg   2340

catcataatc ggtttctgtg cacctgtgat gctgtgtggt ttgtctggtg ggttaaccat   2400

acggaggtga ctattcctta cctggccaca gatgtgactt gtgtggggcc aggagcacac   2460

aagggccaaa gtgtgatctc cctggatctg tacacctgtg agttagatct gactaacctg   2520

attctgttct cactttccat atctgtatct ctctttctca tggtgatgat gacagcaagt   2580

cacctctatt tctgggatgt gtggtatatt taccatttct gtaaggccaa gataaagggg   2640

tatcagcgtc taatatcacc agactgttgc tatgatgctt ttattgtgta tgacactaaa   2700

gacccagctg tgaccgagtg ggttttggct gagctggtgg ccaaactgga agacccaaga   2760

gagaaacatt ttaatttatg tctcgaggaa agggactggt taccagggca gccagttctg   2820

gaaaaccttt cccagagcat acagcttagc aaaaagacag tgtttgtgat gacagacaag   2880

tatgcaaaga ctgaaaattt taagatagca ttttacttgt cccatcagag gctcatggat   2940

gaaaaagttg atgtgattat cttgatattt cttgagaagc cctttcagaa gtccaagttc   3000

ctccagctcc ggaaaaggct ctgtgggagt tctgtccttg agtggccaac aaacccgcaa   3060

gctcacccat acttctggca gtgtctaaag aacgccctgg ccacagacaa tcatgtggcc   3120

tatagtcagg tgttcaagga aacggtctag                                    3150
```

<210> SEQ ID NO 4
<211> LENGTH: 1049
<212> TYPE: PRT
<213> ORGANISM: Homo sapiens

<400> SEQUENCE: 4

```
Met Val Phe Pro Met Trp Thr Leu Lys Arg Gln Ile Leu Ile Leu Phe
1               5                   10                  15

Asn Ile Ile Leu Ile Ser Lys Leu Leu Gly Ala Arg Trp Phe Pro Lys
            20                  25                  30

Thr Leu Pro Cys Asp Val Thr Leu Asp Val Pro Lys Asn His Val Ile
        35                  40                  45

Val Asp Cys Thr Asp Lys His Leu Thr Glu Ile Pro Gly Gly Ile Pro
    50                  55                  60

Thr Asn Thr Thr Asn Leu Thr Leu Thr Ile Asn His Ile Pro Asp Ile
65                  70                  75                  80

Ser Pro Ala Ser Phe His Arg Leu Asp His Leu Val Glu Ile Asp Phe
                85                  90                  95

Arg Cys Asn Cys Val Pro Ile Pro Leu Gly Ser Lys Asn Asn Met Cys
            100                 105                 110

Ile Lys Arg Leu Gln Ile Lys Pro Arg Ser Phe Ser Gly Leu Thr Tyr
        115                 120                 125

Leu Lys Ser Leu Tyr Leu Asp Gly Asn Gln Leu Leu Glu Ile Pro Gln
    130                 135                 140

Gly Leu Pro Pro Ser Leu Gln Leu Leu Ser Leu Glu Ala Asn Asn Ile
145                 150                 155                 160
```

-continued

```
Phe Ser Ile Arg Lys Glu Asn Leu Thr Glu Leu Ala Asn Ile Glu Ile
                165                 170                 175

Leu Tyr Leu Gly Gln Asn Cys Tyr Tyr Arg Asn Pro Cys Tyr Val Ser
            180                 185                 190

Tyr Ser Ile Glu Lys Asp Ala Phe Leu Asn Leu Thr Lys Leu Lys Val
        195                 200                 205

Leu Ser Leu Lys Asp Asn Asn Val Thr Ala Val Pro Thr Val Leu Pro
    210                 215                 220

Ser Thr Leu Thr Glu Leu Tyr Leu Tyr Asn Asn Met Ile Ala Lys Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Ala Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Lys Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Ser Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu His
    450                 455                 460

Tyr Phe Arg Tyr Asp Lys Tyr Ala Arg Ser Cys Arg Phe Lys Asn Lys
465                 470                 475                 480

Glu Ala Ser Phe Met Ser Val Asn Glu Ser Cys Tyr Lys Tyr Gly Gln
                485                 490                 495

Thr Leu Asp Leu Ser Lys Asn Ser Ile Phe Phe Val Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu His Lys Leu Glu Val Leu Asp Ile Ser Ser Asn
                565                 570                 575
```

-continued

```
Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620

Glu Phe Arg Gly Asn His Leu Asp Val Leu Trp Arg Glu Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ser Trp Lys Lys Leu Gln Cys Leu Lys Asn Leu Glu Thr Leu
    690                 695                 700

Asp Leu Ser His Asn Gln Leu Thr Thr Val Pro Glu Arg Leu Ser Asn
705                 710                 715                 720

Cys Ser Arg Ser His Lys Asn Leu Ile Leu Lys Asn Asn Gln Ile Arg
                725                 730                 735

Ser Pro Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990
```

-continued

```
Lys Pro Phe Gln Lys Ser Lys Phe  Leu Gln Leu Arg Lys  Arg Leu Cys
        995                1000                 1005

Gly Ser  Ser Val Leu Glu Trp  Pro Thr Asn Pro Gln  Ala His Pro
    1010                1015                 1020

Tyr Phe  Trp Gln Cys Leu Lys  Asn Ala Leu Ala Thr  Asp Asn His
    1025                1030                 1035

Val Ala  Tyr Ser Gln Val Phe  Lys Glu Thr Val
    1040                1045


<210> SEQ ID NO 5
<211> LENGTH: 116
<212> TYPE: PRT
<213> ORGANISM: Mus musculus

<400> SEQUENCE: 5

Gln Val Gln Leu Gln Gln Pro Gly Ala Glu Leu Val Lys Pro Gly Ala
1               5                   10                  15

Ser Val Asn Leu Ser Cys Lys Ala Ser Gly Tyr Thr Phe Thr Asn Asn
            20                  25                  30

Trp Leu His Trp Val Lys Gln Arg Pro Gly Arg Gly Leu Glu Trp Ile
        35                  40                  45

Gly Asp Ile Tyr Pro Ser Asn Gly Arg Thr Asn Tyr Asn Glu Gln Phe
    50                  55                  60

Lys Thr Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Glu Arg Gly Tyr Phe Asp Tyr Trp Gly Gln Gly Thr Ala Leu
            100                 105                 110

Thr Val Ser Ser
        115


<210> SEQ ID NO 6
<211> LENGTH: 348
<212> TYPE: DNA
<213> ORGANISM: Mus musculus

<400> SEQUENCE: 6

caggtgcagc tgcagcagcc tggcgccgaa ctcgtgaaac ctggcgcctc cgtgaacctg      60

agctgcaagg ccagcggcta caccttcacc aacaactggc tgcactgggt caagcagagg     120

cccggcagag gcctggaatg gatcggcgac atctacccca gcaacggccg gaccaactac     180

aacgagcagt tcaagaccaa ggccaccctg accgtggaca agagcagcag caccgcctac     240

atgcagctgt ccagcctgac cagcgaggac agcgccgtgt acttctgcgc cagagagcgg     300

ggctacttcg actattgggg ccagggaacc gctctgaccg tcagctca                  348


<210> SEQ ID NO 7
<211> LENGTH: 122
<212> TYPE: PRT
<213> ORGANISM: Mus musculus

<400> SEQUENCE: 7

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30
```

-continued

Tyr Ala Trp Asn Trp Ile Arg Gln Phe Pro Gly Asn Lys Leu Glu Trp
35 40 45

Met Gly His Ile Ser Tyr Arg Gly Asn Thr Asn Tyr Asn Pro Ser Leu
50 55 60

Lys Ser Arg Ile Ser Ile Thr Arg Asp Thr Ser Lys Asn Gln Phe Phe
65 70 75 80

Leu Gln Leu Asn Ser Val Thr Thr Glu Asp Thr Ala Thr Tyr Tyr Cys
85 90 95

Ala Ser Trp Asn Tyr Tyr Gly Tyr Val Asp Tyr Ala Met Asp Tyr Trp
100 105 110

Gly Gln Gly Thr Ser Val Thr Val Ser Ser
115 120

<210> SEQ ID NO 8
<211> LENGTH: 366
<212> TYPE: DNA
<213> ORGANISM: Mus musculus

<400> SEQUENCE: 8
gacgtgcagc tgcaggaatc tggccctggc ctcgtgaagc ctagccagag cctgagcctg 60
acatgcaccg tgaccggcta cagcatcacc agcgactacg cctggaactg gatccggcag 120
ttccccggca acaagctgga atggatgggc cacatcagct accggggcaa caccaactac 180
aaccccagcc tgaagtcccg gatctccatc acccgggaca ccagcaagaa ccagttcttt 240
ctgcagctga acagcgtgac caccgaggac accgccacct actactgcgc cagctggaac 300
tactacggct acgtggacta tgccatggac tactggggcc agggcacctc cgtgaccgtc 360
agctca 366

<210> SEQ ID NO 9
<211> LENGTH: 121
<212> TYPE: PRT
<213> ORGANISM: Mus musculus

<400> SEQUENCE: 9

Gln Val Gln Leu Lys Glu Ser Gly Pro Gly Leu Val Ala Pro Ser Gln
1 5 10 15

Ser Leu Ser Ile Thr Cys Thr Val Ser Gly Phe Ser Leu Thr Gly Tyr
20 25 30

Gly Val Asn Trp Val Arg Gln Pro Pro Gly Lys Gly Leu Glu Trp Leu
35 40 45

Gly Met Ile Trp Gly Asp Gly Ser Thr Asp Tyr Asn Ser Ala Leu Lys
50 55 60

Ser Arg Leu Ser Ile Arg Lys Asp Asn Ser Lys Ser Gln Val Phe Leu
65 70 75 80

Lys Met Asn Ser Leu Gln Thr Asp Asp Thr Ala Arg Tyr Tyr Cys Ala
85 90 95

Arg Asp Lys Gly Tyr Asp Gly Tyr Tyr Tyr Ala Met Asp Tyr Trp Gly
100 105 110

Gln Gly Thr Ser Val Thr Val Ser Ser
115 120

<210> SEQ ID NO 10
<211> LENGTH: 363
<212> TYPE: DNA
<213> ORGANISM: Mus musculus

<400> SEQUENCE: 10

```
caggtgcagc tgaaagagtc tggccctgga ctggtggccc ctagccagag cctgagcatc     60

acctgtaccg tgtccggctt cagcctgacc ggctacggcg tgaactgggt gcgccagcct    120

cctggcaaag gcctggaatg gctgggcatg atctggggcg acggcagcac cgactacaac    180

agcgccctga agtcccggct gagcatccgg aaggacaaca gcaagtccca ggtgttcctg    240

aagatgaaca gcctgcagac cgacgacacc gcccggtact actgcgccag agacaagggc    300

tacgacggct actactacgc catggactac tggggccagg gcacctctgt gaccgtcagc    360

tca                                                                  363
```

<210> SEQ ID NO 11
<211> LENGTH: 106
<212> TYPE: PRT
<213> ORGANISM: Mus musculus

<400> SEQUENCE: 11

```
Asp Ile Gln Met Thr Gln Ser Pro Ser Ser Leu Ser Thr Ser Leu Gly
1               5                   10                  15

Gly Lys Val Thr Ile Thr Cys Lys Ala Ser Gln Asp Ile Asn Lys Tyr
            20                  25                  30

Ile Ala Trp Tyr Gln His Lys Pro Gly Lys Gly Pro Arg Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Tyr Leu Leu Thr
                85                  90                  95

Phe Gly Ala Gly Thr Lys Leu Glu Leu Lys
            100                 105
```

<210> SEQ ID NO 12
<211> LENGTH: 318
<212> TYPE: DNA
<213> ORGANISM: Mus musculus

<400> SEQUENCE: 12

```
gacatccaga tgacccagag ccctagcagc ctgagcacaa gcctgggcgg caaagtgacc     60

atcacatgca aggccagcca ggacatcaac aagtatatcg cctggtatca gcacaaaccc    120

ggcaagggcc ccagactgct gattcactac accagcaccc tgcagcccgg catccccagc    180

agattttctg gcagcggctc cggcagagac tacagcttca gcatcagcaa cctggaaccc    240

gaggatatcg ccacctacta ctgcctgcag tacgactacc tgctgacctt cggagccggc    300

accaagctgg aactgaag                                                  318
```

<210> SEQ ID NO 13
<211> LENGTH: 106
<212> TYPE: PRT
<213> ORGANISM: Mus musculus

<400> SEQUENCE: 13

```
Asp Ile Gln Met Thr Gln Thr Pro Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30
```

```
Leu Asn Trp Tyr Gln Gln Lys Pro Asp Gly Thr Val Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Asn Asn Leu Glu Gln
65                  70                  75                  80

Glu Asp Ile Ala Thr Tyr Phe Cys Gln Gln Gly Asp Thr Phe Pro Thr
                85                  90                  95

Phe Gly Gly Gly Thr Lys Leu Glu Ile Lys
            100                 105


<210> SEQ ID NO 14
<211> LENGTH: 318
<212> TYPE: DNA
<213> ORGANISM: Mus musculus

<400> SEQUENCE: 14

gacatccaga tgacccagac acccagcagc ctgagcgcca gcctgggcga tagagtgacc     60

atcagctgca gagccagcca ggacatcagc aactacctga actggtatca gcagaaaccc    120

gacggcaccg tgaagctgct gatctactac accagcagac tgcacagcgg cgtgcccagc    180

agattttctg gcagcggctc cggcaccgac tacagcctga ccatcaacaa cctggaacag    240

gaagatatcg ctacctactt ctgtcagcaa ggcgacacct tccccacctt cggcggaggc    300

accaagctgg aaatcaag                                                  318


<210> SEQ ID NO 15
<211> LENGTH: 107
<212> TYPE: PRT
<213> ORGANISM: Mus musculus

<400> SEQUENCE: 15

Asp Ile Gln Met Thr Gln Ser Pro Ala Ser Leu Ser Ala Ser Val Gly
1               5                   10                  15

Glu Thr Val Thr Ile Thr Cys Arg Ala Ser Glu Asn Ile Tyr Ser Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Glu Gly Val Pro Ser Arg Phe Ser Gly
    50                  55                  60

Ser Gly Ser Gly Thr Gln Phe Ser Leu Lys Ile Asn Ser Leu Gln Pro
65                  70                  75                  80

Glu Asp Phe Gly Ser Tyr Tyr Cys Gln His His Tyr Gly Ile Pro Tyr
                85                  90                  95

Thr Phe Gly Gly Gly Thr Lys Leu Glu Ile Lys
            100                 105


<210> SEQ ID NO 16
<211> LENGTH: 321
<212> TYPE: DNA
<213> ORGANISM: Mus musculus

<400> SEQUENCE: 16

gacatccaga tgacacagtc tcccgccagc ctgagcgcct ctgtgggaga gacagtgacc     60

atcacctgtc gggccagcga gaacatctac agctacctgg cctggtatca gcagaagcag    120

ggcaagagcc cccagctgct ggtgtacgat gccaagacac tggccgaggg cgtgcccagc    180

agattttctg gcagcggctc cggcacccag ttcagcctga agatcaacag cctgcagccc    240
```

gaggacttcg gcagctacta ctgccagcac cactacggca tcccttacac cttcggcgga 300
ggcaccaagc tggaaatcaa g 321

<210> SEQ ID NO 17
<211> LENGTH: 10
<212> TYPE: PRT
<213> ORGANISM: Mus musculus

<400> SEQUENCE: 17

Gly Tyr Thr Phe Thr Asn Asn Trp Leu His
1 5 10

<210> SEQ ID NO 18
<211> LENGTH: 10
<212> TYPE: PRT
<213> ORGANISM: Mus musculus

<400> SEQUENCE: 18

Asp Ile Tyr Pro Ser Asn Gly Arg Thr Asn
1 5 10

<210> SEQ ID NO 19
<211> LENGTH: 7
<212> TYPE: PRT
<213> ORGANISM: Mus musculus

<400> SEQUENCE: 19

Glu Arg Gly Tyr Phe Asp Tyr
1 5

<210> SEQ ID NO 20
<211> LENGTH: 11
<212> TYPE: PRT
<213> ORGANISM: Mus musculus

<400> SEQUENCE: 20

Lys Ala Ser Gln Asp Ile Asn Lys Tyr Ile Ala
1 5 10

<210> SEQ ID NO 21
<211> LENGTH: 7
<212> TYPE: PRT
<213> ORGANISM: Mus musculus

<400> SEQUENCE: 21

Tyr Thr Ser Thr Leu Gln Pro
1 5

<210> SEQ ID NO 22
<211> LENGTH: 8
<212> TYPE: PRT
<213> ORGANISM: Mus musculus

<400> SEQUENCE: 22

Leu Gln Tyr Asp Tyr Leu Leu Thr
1 5

<210> SEQ ID NO 23
<211> LENGTH: 11
<212> TYPE: PRT
<213> ORGANISM: Mus musculus -continued

<400> SEQUENCE: 23

Gly Tyr Ser Ile Thr Ser Asp Tyr Ala Trp Asn
1 5 10

<210> SEQ ID NO 24
<211> LENGTH: 9
<212> TYPE: PRT
<213> ORGANISM: Mus musculus

<400> SEQUENCE: 24

His Ile Ser Tyr Arg Gly Asn Thr Asn
1 5

<210> SEQ ID NO 25
<211> LENGTH: 13
<212> TYPE: PRT
<213> ORGANISM: Mus musculus

<400> SEQUENCE: 25

Trp Asn Tyr Tyr Gly Tyr Val Asp Tyr Ala Met Asp Tyr
1 5 10

<210> SEQ ID NO 26
<211> LENGTH: 11
<212> TYPE: PRT
<213> ORGANISM: Mus musculus

<400> SEQUENCE: 26

Arg Ala Ser Gln Asp Ile Ser Asn Tyr Leu Asn
1 5 10

<210> SEQ ID NO 27
<211> LENGTH: 7
<212> TYPE: PRT
<213> ORGANISM: Mus musculus

<400> SEQUENCE: 27

Tyr Thr Ser Arg Leu His Ser
1 5

<210> SEQ ID NO 28
<211> LENGTH: 8
<212> TYPE: PRT
<213> ORGANISM: Mus musculus

<400> SEQUENCE: 28

Gln Gln Gly Asp Thr Phe Pro Thr
1 5

<210> SEQ ID NO 29
<211> LENGTH: 10
<212> TYPE: PRT
<213> ORGANISM: Mus musculus

<400> SEQUENCE: 29

Gly Phe Ser Leu Thr Gly Tyr Gly Val Asn
1 5 10

<210> SEQ ID NO 30
<211> LENGTH: 9
<212> TYPE: PRT
<213> ORGANISM: Mus musculus

```
<400> SEQUENCE: 30

Met Ile Trp Gly Asp Gly Ser Thr Asp
1               5


<210> SEQ ID NO 31
<211> LENGTH: 13
<212> TYPE: PRT
<213> ORGANISM: Mus musculus

<400> SEQUENCE: 31

Asp Lys Gly Tyr Asp Gly Tyr Tyr Tyr Ala Met Asp Tyr
1               5                   10


<210> SEQ ID NO 32
<211> LENGTH: 11
<212> TYPE: PRT
<213> ORGANISM: Mus musculus

<400> SEQUENCE: 32

Arg Ala Ser Glu Asn Ile Tyr Ser Tyr Leu Ala
1               5                   10


<210> SEQ ID NO 33
<211> LENGTH: 7
<212> TYPE: PRT
<213> ORGANISM: Mus musculus

<400> SEQUENCE: 33

Asp Ala Lys Thr Leu Ala Glu
1               5


<210> SEQ ID NO 34
<211> LENGTH: 9
<212> TYPE: PRT
<213> ORGANISM: Mus musculus

<400> SEQUENCE: 34

Gln His His Tyr Gly Ile Pro Tyr Thr
1               5


<210> SEQ ID NO 35
<211> LENGTH: 465
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(465)
<223> OTHER INFORMATION: Amino acid sequence of heavy chain of chimeric
      anti-human TLR7 antibody AT01 (cAT01)

<400> SEQUENCE: 35

Met Lys His Leu Trp Phe Phe Leu Leu Leu Val Ala Ala Pro Arg Trp
1               5                   10                  15

Val Leu Ser Gln Val Gln Leu Gln Gln Pro Gly Ala Glu Leu Val Lys
            20                  25                  30

Pro Gly Ala Ser Val Asn Leu Ser Cys Lys Ala Ser Gly Tyr Thr Phe
        35                  40                  45

Thr Asn Asn Trp Leu His Trp Val Lys Gln Arg Pro Gly Arg Gly Leu
    50                  55                  60

Glu Trp Ile Gly Asp Ile Tyr Pro Ser Asn Gly Arg Thr Asn Tyr Asn
65                  70                  75                  80
```

-continued

```
Glu Gln Phe Lys Thr Lys Ala Thr Leu Thr Val Asp Lys Ser Ser Ser
                85                  90                  95

Thr Ala Tyr Met Gln Leu Ser Ser Leu Thr Ser Glu Asp Ser Ala Val
            100                 105                 110

Tyr Phe Cys Ala Arg Glu Arg Gly Tyr Phe Asp Tyr Trp Gly Gln Gly
        115                 120                 125

Thr Ala Leu Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465
```

<210> SEQ ID NO 36
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(233)
<223> OTHER INFORMATION: Amino acid sequence of light chain of chimeric anti-human TLR7 antibody AT01 (cAT01)

<400> SEQUENCE: 36

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Thr Ser Leu Gly Gly Lys Val Thr Ile Thr Cys Lys Ala Ser Gln Asp
        35                  40                  45

Ile Asn Lys Tyr Ile Ala Trp Tyr Gln His Lys Pro Gly Lys Gly Pro
    50                  55                  60

Arg Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Ser Phe Ser Ile Ser
                85                  90                  95

Asn Leu Glu Pro Glu Asp Ile Ala Thr Tyr Tyr Cys Leu Gln Tyr Asp
            100                 105                 110

Tyr Leu Leu Thr Phe Gly Ala Gly Thr Lys Leu Glu Leu Lys Arg Ala
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230
```

<210> SEQ ID NO 37
<211> LENGTH: 471
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(471)
<223> OTHER INFORMATION: Amino acid sequence of heavy chain of chimeric anti-human TLR7 antibody NB7 (cNB7)

<400> SEQUENCE: 37

```
Met Lys His Leu Trp Phe Phe Leu Leu Leu Val Ala Ala Pro Arg Trp
1               5                   10                  15

Val Leu Ser Asp Val Gln Leu Gln Glu Ser Gly Pro Gly Leu Val Lys
            20                  25                  30
```

-continued

```
Pro Ser Gln Ser Leu Ser Leu Thr Cys Thr Val Thr Gly Tyr Ser Ile
        35                  40                  45

Thr Ser Asp Tyr Ala Trp Asn Trp Ile Arg Gln Phe Pro Gly Asn Lys
    50                  55                  60

Leu Glu Trp Met Gly His Ile Ser Tyr Arg Gly Asn Thr Asn Tyr Asn
65                  70                  75                  80

Pro Ser Leu Lys Ser Arg Ile Ser Ile Thr Arg Asp Thr Ser Lys Asn
                85                  90                  95

Gln Phe Phe Leu Gln Leu Asn Ser Val Thr Thr Glu Asp Thr Ala Thr
            100                 105                 110

Tyr Tyr Cys Ala Ser Trp Asn Tyr Tyr Gly Tyr Val Asp Tyr Ala Met
        115                 120                 125

Asp Tyr Trp Gly Gln Gly Thr Ser Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Leu Leu Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285

Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445
```

```
Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 38
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(233)
<223> OTHER INFORMATION: Amino acid sequence of light chain of chimeric
      anti-human TLR7 antibody NB7 (cNB7)

<400> SEQUENCE: 38

Met Val Leu Gln Thr Gln Val Phe Ile Ser Leu Leu Leu Trp Ile Ser
1               5                   10                  15

Gly Ala Tyr Gly Asp Ile Gln Met Thr Gln Thr Pro Ser Ser Leu Ser
            20                  25                  30

Ala Ser Leu Gly Asp Arg Val Thr Ile Ser Cys Arg Ala Ser Gln Asp
        35                  40                  45

Ile Ser Asn Tyr Leu Asn Trp Tyr Gln Gln Lys Pro Asp Gly Thr Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Ser Leu Thr Ile Asn
                85                  90                  95

Asn Leu Glu Gln Glu Asp Ile Ala Thr Tyr Phe Cys Gln Gln Gly Asp
            100                 105                 110

Thr Phe Pro Thr Phe Gly Gly Gly Thr Lys Leu Glu Ile Lys Arg Ala
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 39
<211> LENGTH: 470
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(470)
<223> OTHER INFORMATION: Amino acid sequence of heavy chain of chimeric
      anti-human TLR7 antibody FAN2 (cFAN2)
```

-continued

<400> SEQUENCE: 39

```
Met Lys His Leu Trp Phe Phe Leu Leu Leu Val Ala Ala Pro Arg Trp
1               5                   10                  15

Val Leu Ser Gln Val Gln Leu Lys Glu Ser Gly Pro Gly Leu Val Ala
            20                  25                  30

Pro Ser Gln Ser Leu Ser Ile Thr Cys Thr Val Ser Gly Phe Ser Leu
        35                  40                  45

Thr Gly Tyr Gly Val Asn Trp Val Arg Gln Pro Pro Gly Lys Gly Leu
    50                  55                  60

Glu Trp Leu Gly Met Ile Trp Gly Asp Gly Ser Thr Asp Tyr Asn Ser
65                  70                  75                  80

Ala Leu Lys Ser Arg Leu Ser Ile Arg Lys Asp Asn Ser Lys Ser Gln
                85                  90                  95

Val Phe Leu Lys Met Asn Ser Leu Gln Thr Asp Asp Thr Ala Arg Tyr
            100                 105                 110

Tyr Cys Ala Arg Asp Lys Gly Tyr Asp Gly Tyr Tyr Tyr Ala Met Asp
        115                 120                 125

Tyr Trp Gly Gln Gly Thr Ser Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Arg Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Glu Glu Met Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

```
Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470
```

<210> SEQ ID NO 40
<211> LENGTH: 234
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(234)
<223> OTHER INFORMATION: Amino acid sequence of light chain of chimeric anti-human TLR7 antibody FAN2 (cFAN2)

<400> SEQUENCE: 40

```
Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ala Ser Leu Ser
            20                  25                  30

Ala Ser Val Gly Glu Thr Val Thr Ile Thr Cys Arg Ala Ser Glu Asn
        35                  40                  45

Ile Tyr Ser Tyr Leu Ala Trp Tyr Gln Gln Lys Gln Gly Lys Ser Pro
    50                  55                  60

Gln Leu Leu Val Tyr Asp Ala Lys Thr Leu Ala Glu Gly Val Pro Ser
65                  70                  75                  80

Arg Phe Ser Gly Ser Gly Ser Gly Thr Gln Phe Ser Leu Lys Ile Asn
                85                  90                  95

Ser Leu Gln Pro Glu Asp Phe Gly Ser Tyr Tyr Cys Gln His His Tyr
            100                 105                 110

Gly Ile Pro Tyr Thr Phe Gly Gly Gly Thr Lys Leu Glu Ile Lys Arg
        115                 120                 125

Ala Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

<210> SEQ ID NO 41
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(116)
<223> OTHER INFORMATION: Amino acid sequence of heavy chain variable region of huAT01_H1_IgG1LALA

<400> SEQUENCE: 41

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Trp Leu His Trp Val Arg Gln Ala Pro Gly Gln Gly Leu Glu Trp Met
        35                  40                  45

Gly Asp Ile Tyr Pro Ser Asn Gly Arg Thr Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Arg Gly Tyr Phe Asp Tyr Trp Gly Gln Gly Thr Leu Val
            100                 105                 110

Thr Val Ser Ser
        115
```

<210> SEQ ID NO 42
<211> LENGTH: 116
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(116)
<223> OTHER INFORMATION: Amino acid sequence of heavy chain variable region of huAT01_H3_IgG1LALA

<400> SEQUENCE: 42

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Asn
            20                  25                  30

Trp Leu His Trp Val Arg Gln Ala Pro Gly Gln Gly Leu Glu Trp Met
        35                  40                  45

Gly Asp Ile Tyr Pro Ser Asn Gly Arg Thr Asn Tyr Ala Gln Lys Phe
    50                  55                  60

Gln Gly Arg Val Thr Leu Thr Val Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Glu Arg Gly Tyr Phe Asp Tyr Trp Gly Gln Gly Thr Leu Val
            100                 105                 110

Thr Val Ser Ser
        115
```

<210> SEQ ID NO 43
<211> LENGTH: 106
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (1)..(106)
<223> OTHER INFORMATION: Amino acid sequence of light chain variable
      region of huAT01_L1

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Leu Gln Tyr Asp Tyr Leu Leu Thr
                85                  90                  95

Phe Gly Gln Gly Thr Lys Val Glu Ile Lys
            100                 105


<210> SEQ ID NO 44
<211> LENGTH: 106
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(106)
<223> OTHER INFORMATION: Amino acid sequence of light chain variable
      region of huAT01_L2

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Lys Tyr
            20                  25                  30

Ile Ala Trp Tyr Gln Gln Lys Pro Gly Lys Ala Pro Lys Leu Leu Ile
        35                  40                  45

His Tyr Thr Ser Thr Leu Gln Pro Gly Ile Pro Ser Arg Phe Ser Gly
    50                  55                  60

Ser Gly Ser Gly Arg Asp Tyr Thr Leu Thr Ile Ser Ser Leu Gln Pro
65                  70                  75                  80

Glu Asp Phe Ala Thr Tyr Tyr Cys Leu Gln Tyr Asp Tyr Leu Leu Thr
                85                  90                  95

Phe Gly Gln Gly Thr Lys Val Glu Ile Lys
            100                 105


<210> SEQ ID NO 45
<211> LENGTH: 465
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(465)
<223> OTHER INFORMATION: Amino acid sequence of huAT01_H1_IgG1LALA
```

<400> SEQUENCE: 45

```
Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Asn Trp Leu His Trp Val Arg Gln Ala Pro Gly Gln Gly Leu
    50                  55                  60

Glu Trp Met Gly Asp Ile Tyr Pro Ser Asn Gly Arg Thr Asn Tyr Ala
65                  70                  75                  80

Gln Lys Phe Gln Gly Arg Val Thr Ile Thr Ala Asp Lys Ser Thr Ser
                85                  90                  95

Thr Ala Tyr Met Glu Leu Ser Ser Leu Arg Ser Glu Asp Thr Ala Val
            100                 105                 110

Tyr Tyr Cys Ala Arg Glu Arg Gly Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Ala Ala Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415
```

```
Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465


<210> SEQ ID NO 46
<211> LENGTH: 465
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(465)
<223> OTHER INFORMATION: Amino acid sequence of huAT01_H3_IgG1LALA

<400> SEQUENCE: 46

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Asn Trp Leu His Trp Val Arg Gln Ala Pro Gly Gln Gly Leu
    50                  55                  60

Glu Trp Met Gly Asp Ile Tyr Pro Ser Asn Gly Arg Thr Asn Tyr Ala
65                  70                  75                  80

Gln Lys Phe Gln Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Glu Arg Gly Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Gln Thr Tyr Ile Cys Asn Val Asn His Lys Pro
    210                 215                 220

Ser Asn Thr Lys Val Asp Lys Arg Val Glu Pro Lys Ser Cys Asp Lys
225                 230                 235                 240

Thr His Thr Cys Pro Pro Cys Pro Ala Pro Glu Ala Ala Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285
```

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Glu Glu Met Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys
465

<210> SEQ ID NO 47
<211> LENGTH: 462
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(462)
<223> OTHER INFORMATION: Amino acid sequence of huAT01_H3_IgG4Pro

<400> SEQUENCE: 47

Met Lys His Leu Trp Phe Phe Leu Leu Leu Val Ala Ala Pro Arg Trp
1               5                   10                  15

Val Leu Ser Gln Val Gln Leu Val Gln Ser Gly Ala Glu Val Lys Lys
            20                  25                  30

Pro Gly Ala Ser Val Lys Val Ser Cys Lys Ala Ser Gly Tyr Thr Phe
        35                  40                  45

Thr Asn Asn Trp Leu His Trp Val Arg Gln Ala Pro Gly Gln Gly Leu
    50                  55                  60

Glu Trp Met Gly Asp Ile Tyr Pro Ser Asn Gly Arg Thr Asn Tyr Ala
65                  70                  75                  80

Gln Lys Phe Gln Gly Arg Val Thr Leu Thr Val Asp Lys Ser Thr Ser
                85                  90                  95

Thr Ala Tyr Met Glu Leu Ser Ser Leu Arg Ser Glu Asp Thr Ala Val
            100                 105                 110

Tyr Phe Cys Ala Arg Glu Arg Gly Tyr Phe Asp Tyr Trp Gly Gln Gly
        115                 120                 125

Thr Leu Val Thr Val Ser Ser Ala Ser Thr Lys Gly Pro Ser Val Phe
    130                 135                 140

Pro Leu Ala Pro Cys Ser Arg Ser Thr Ser Glu Ser Thr Ala Ala Leu
145                 150                 155                 160

```
Gly Cys Leu Val Lys Asp Tyr Phe Pro Glu Pro Val Thr Val Ser Trp
                165                 170                 175

Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
        195                 200                 205

Ser Ser Leu Gly Thr Lys Thr Tyr Thr Cys Asn Val Asp His Lys Pro
    210                 215                 220

Ser Asn Thr Lys Val Asp Lys Arg Val Glu Ser Lys Tyr Gly Pro Pro
225                 230                 235                 240

Cys Pro Pro Cys Pro Ala Pro Glu Phe Leu Gly Gly Pro Ser Val Phe
                245                 250                 255

Leu Phe Pro Pro Lys Pro Lys Asp Thr Leu Met Ile Ser Arg Thr Pro
            260                 265                 270

Glu Val Thr Cys Val Val Val Asp Val Ser Gln Glu Asp Pro Glu Val
        275                 280                 285

Gln Phe Asn Trp Tyr Val Asp Gly Val Glu Val His Asn Ala Lys Thr
    290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
                325                 330                 335

Lys Val Ser Asn Lys Gly Leu Pro Ser Ser Ile Glu Lys Thr Ile Ser
            340                 345                 350

Lys Ala Lys Gly Gln Pro Arg Glu Pro Gln Val Tyr Thr Leu Pro Pro
        355                 360                 365

Ser Gln Glu Glu Met Thr Lys Asn Gln Val Ser Leu Thr Cys Leu Val
    370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
                405                 410                 415

Gly Ser Phe Phe Leu Tyr Ser Arg Leu Thr Val Asp Lys Ser Arg Trp
            420                 425                 430

Gln Glu Gly Asn Val Phe Ser Cys Ser Val Met His Glu Ala Leu His
        435                 440                 445

Asn His Tyr Thr Gln Lys Ser Leu Ser Leu Ser Leu Gly Lys
    450                 455                 460


<210> SEQ ID NO 48
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(233)
<223> OTHER INFORMATION: Amino acid sequence of huAT01_L1

<400> SEQUENCE: 48

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45
```

```
Ile Asn Lys Tyr Ile Ala Trp Tyr Gln Gln Lys Pro Gly Lys Ala Pro
    50                  55                  60

Lys Leu Leu Ile His Tyr Thr Ser Thr Leu Gln Pro Gly Val Pro Ser
65                  70                  75                  80

Arg Phe Ser Gly Ser Gly Ser Gly Arg Asp Phe Thr Leu Thr Ile Ser
                85                  90                  95

Ser Leu Gln Pro Glu Asp Phe Ala Thr Tyr Tyr Cys Leu Gln Tyr Asp
            100                 105                 110

Tyr Leu Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 49
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(233)
<223> OTHER INFORMATION: Amino acid sequence of huAT01_L2

<400> SEQUENCE: 49

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Lys Ala Ser Gln Asp
        35                  40                  45

Ile Asn Lys Tyr Ile Ala Trp Tyr Gln Gln Lys Pro Gly Lys Ala Pro
    50                  55                  60

Lys Leu Leu Ile His Tyr Thr Ser Thr Leu Gln Pro Gly Ile Pro Ser
65                  70                  75                  80

Arg Phe Ser Gly Ser Gly Ser Gly Arg Asp Tyr Thr Leu Thr Ile Ser
                85                  90                  95

Ser Leu Gln Pro Glu Asp Phe Ala Thr Tyr Tyr Cys Leu Gln Tyr Asp
            100                 105                 110

Tyr Leu Leu Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160
```

```
Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205

Lys Val Tyr Ala Cys Glu Val Thr His Gln Gly Leu Ser Ser Pro Val
    210                 215                 220

Thr Lys Ser Phe Asn Arg Gly Glu Cys
225                 230


<210> SEQ ID NO 50
<211> LENGTH: 122
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(122)
<223> OTHER INFORMATION: Amino acid sequence of heavy chain variable
      region of huNB7_H3_IgG1LALA

<400> SEQUENCE: 50

Asp Val Gln Leu Gln Glu Ser Gly Pro Gly Leu Val Lys Pro Ser Asp
1               5                   10                  15

Thr Leu Ser Leu Thr Cys Thr Val Thr Gly Tyr Ser Ile Thr Ser Asp
            20                  25                  30

Tyr Ala Trp Asn Trp Ile Arg Gln Pro Pro Gly Asn Lys Leu Glu Trp
        35                  40                  45

Ile Gly His Ile Ser Tyr Arg Gly Asn Thr Asn Tyr Asn Pro Ser Leu
    50                  55                  60

Lys Ser Arg Val Thr Ile Ser Arg Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Ser Trp Asn Tyr Tyr Gly Tyr Val Asp Tyr Ala Met Asp Tyr Trp
            100                 105                 110

Gly Gln Gly Thr Thr Val Thr Val Ser Ser
        115                 120


<210> SEQ ID NO 51
<211> LENGTH: 106
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(106)
<223> OTHER INFORMATION: Amino acid sequence of light chain variable
      region of huNB7_L3

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Lys Pro Gly Lys Ala Val Lys Leu Leu Ile
        35                  40                  45
```

-continued

```
Tyr Tyr Thr Ser Arg Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Gly Asp Thr Phe Pro Thr
                85                  90                  95

Phe Gly Gln Gly Thr Lys Val Glu Ile Lys
            100                 105


<210> SEQ ID NO 52
<211> LENGTH: 471
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(471)
<223> OTHER INFORMATION: Amino acid sequence of huNB7_H3_IgG1LALA

<400> SEQUENCE: 52

Met Lys His Leu Trp Phe Phe Leu Leu Leu Val Ala Ala Pro Arg Trp
1               5                   10                  15

Val Leu Ser Asp Val Gln Leu Gln Glu Ser Gly Pro Gly Leu Val Lys
            20                  25                  30

Pro Ser Asp Thr Leu Ser Leu Thr Cys Thr Val Thr Gly Tyr Ser Ile
        35                  40                  45

Thr Ser Asp Tyr Ala Trp Asn Trp Ile Arg Gln Pro Pro Gly Asn Lys
    50                  55                  60

Leu Glu Trp Ile Gly His Ile Ser Tyr Arg Gly Asn Thr Asn Tyr Asn
65                  70                  75                  80

Pro Ser Leu Lys Ser Arg Val Thr Ile Ser Arg Asp Thr Ser Lys Asn
                85                  90                  95

Gln Phe Ser Leu Lys Leu Ser Ser Val Thr Ala Ala Asp Thr Ala Val
            100                 105                 110

Tyr Tyr Cys Ala Ser Trp Asn Tyr Tyr Gly Tyr Val Asp Tyr Ala Met
        115                 120                 125

Asp Tyr Trp Gly Gln Gly Thr Thr Val Thr Val Ser Ser Ala Ser Thr
    130                 135                 140

Lys Gly Pro Ser Val Phe Pro Leu Ala Pro Ser Ser Lys Ser Thr Ser
145                 150                 155                 160

Gly Gly Thr Ala Ala Leu Gly Cys Leu Val Lys Asp Tyr Phe Pro Glu
                165                 170                 175

Pro Val Thr Val Ser Trp Asn Ser Gly Ala Leu Thr Ser Gly Val His
            180                 185                 190

Thr Phe Pro Ala Val Leu Gln Ser Ser Gly Leu Tyr Ser Leu Ser Ser
        195                 200                 205

Val Val Thr Val Pro Ser Ser Ser Leu Gly Thr Gln Thr Tyr Ile Cys
    210                 215                 220

Asn Val Asn His Lys Pro Ser Asn Thr Lys Val Asp Lys Arg Val Glu
225                 230                 235                 240

Pro Lys Ser Cys Asp Lys Thr His Thr Cys Pro Pro Cys Pro Ala Pro
                245                 250                 255

Glu Ala Ala Gly Gly Pro Ser Val Phe Leu Phe Pro Pro Lys Pro Lys
            260                 265                 270

Asp Thr Leu Met Ile Ser Arg Thr Pro Glu Val Thr Cys Val Val Val
        275                 280                 285
```

```
Asp Val Ser His Glu Asp Pro Glu Val Lys Phe Asn Trp Tyr Val Asp
    290                 295                 300

Gly Val Glu Val His Asn Ala Lys Thr Lys Pro Arg Glu Glu Gln Tyr
305                 310                 315                 320

Asn Ser Thr Tyr Arg Val Val Ser Val Leu Thr Val Leu His Gln Asp
                325                 330                 335

Trp Leu Asn Gly Lys Glu Tyr Lys Cys Lys Val Ser Asn Lys Ala Leu
            340                 345                 350

Pro Ala Pro Ile Glu Lys Thr Ile Ser Lys Ala Lys Gly Gln Pro Arg
        355                 360                 365

Glu Pro Gln Val Tyr Thr Leu Pro Pro Ser Arg Glu Glu Met Thr Lys
    370                 375                 380

Asn Gln Val Ser Leu Thr Cys Leu Val Lys Gly Phe Tyr Pro Ser Asp
385                 390                 395                 400

Ile Ala Val Glu Trp Glu Ser Asn Gly Gln Pro Glu Asn Asn Tyr Lys
                405                 410                 415

Thr Thr Pro Pro Val Leu Asp Ser Asp Gly Ser Phe Phe Leu Tyr Ser
            420                 425                 430

Lys Leu Thr Val Asp Lys Ser Arg Trp Gln Gln Gly Asn Val Phe Ser
        435                 440                 445

Cys Ser Val Met His Glu Ala Leu His Asn His Tyr Thr Gln Lys Ser
    450                 455                 460

Leu Ser Leu Ser Pro Gly Lys
465                 470


<210> SEQ ID NO 53
<211> LENGTH: 233
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(233)
<223> OTHER INFORMATION: Amino acid sequence of huNB7_L3

<400> SEQUENCE: 53

Met Val Leu Gln Thr Gln Val Phe Ile Ser Leu Leu Leu Trp Ile Ser
1               5                   10                  15

Gly Ala Tyr Gly Asp Ile Gln Met Thr Gln Ser Pro Ser Ser Leu Ser
            20                  25                  30

Ala Ser Val Gly Asp Arg Val Thr Ile Thr Cys Arg Ala Ser Gln Asp
        35                  40                  45

Ile Ser Asn Tyr Leu Asn Trp Tyr Gln Gln Lys Pro Gly Lys Ala Val
    50                  55                  60

Lys Leu Leu Ile Tyr Tyr Thr Ser Arg Leu His Ser Gly Val Pro Ser
65                  70                  75                  80

Arg Phe Ser Gly Ser Gly Ser Gly Thr Asp Tyr Thr Leu Thr Ile Ser
                85                  90                  95

Ser Leu Gln Pro Glu Asp Phe Ala Thr Tyr Phe Cys Gln Gln Gly Asp
            100                 105                 110

Thr Phe Pro Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160
```

Arg Glu Ala Lys Val Gln Trp Lys Val Asp Asn Ala Leu Gln Ser Gly
165 170 175

Asn Ser Gln Glu Ser Val Thr Glu Gln Asp Ser Lys Asp Ser Thr Tyr
180 185 190

Ser Leu Ser Ser Thr Leu Thr Leu Ser Lys Ala Asp Tyr Glu Lys His
195 200 205

Lys Val Tyr Ala Cys Glu Val Thr His Gln Gly Leu Ser Ser Pro Val
210 215 220

Thr Lys Ser Phe Asn Arg Gly Glu Cys
225 230

<210> SEQ ID NO 54
<211> LENGTH: 468
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(468)
<223> OTHER INFORMATION: Amino acid sequence of huNB7_H3_IgG4Pro

<400> SEQUENCE: 54

Met Lys His Leu Trp Phe Phe Leu Leu Leu Val Ala Ala Pro Arg Trp
1 5 10 15

Val Leu Ser Asp Val Gln Leu Gln Glu Ser Gly Pro Gly Leu Val Lys
20 25 30

Pro Ser Asp Thr Leu Ser Leu Thr Cys Thr Val Thr Gly Tyr Ser Ile
35 40 45

Thr Ser Asp Tyr Ala Trp Asn Trp Ile Arg Gln Pro Pro Gly Asn Lys
50 55 60

Leu Glu Trp Ile Gly His Ile Ser Tyr Arg Gly Asn Thr Asn Tyr Asn
65 70 75 80

Pro Ser Leu Lys Ser Arg Val Thr Ile Ser Arg Asp Thr Ser Lys Asn
85 90 95

Gln Phe Ser Leu Lys Leu Ser Ser Val Thr Ala Ala Asp Thr Ala Val
100 105 110

Tyr Tyr Cys Ala Ser Trp Asn Tyr Tyr Gly Tyr Val Asp Tyr Ala Met
115 120 125

Asp Tyr Trp Gly Gln Gly Thr Thr Val Thr Val Ser Ser Ala Ser Thr
130 135 140

Lys Gly Pro Ser Val Phe Pro Leu Ala Pro Cys Ser Arg Ser Thr Ser
145 150 155 160

Glu Ser Thr Ala Ala Leu Gly Cys Leu Val Lys Asp Tyr Phe Pro Glu
165 170 175

Pro Val Thr Val Ser Trp Asn Ser Gly Ala Leu Thr Ser Gly Val His
180 185 190

Thr Phe Pro Ala Val Leu Gln Ser Ser Gly Leu Tyr Ser Leu Ser Ser
195 200 205

Val Val Thr Val Pro Ser Ser Ser Leu Gly Thr Lys Thr Tyr Thr Cys
210 215 220

Asn Val Asp His Lys Pro Ser Asn Thr Lys Val Asp Lys Arg Val Glu
225 230 235 240

Ser Lys Tyr Gly Pro Pro Cys Pro Pro Cys Pro Ala Pro Glu Phe Leu
245 250 255

Gly Gly Pro Ser Val Phe Leu Phe Pro Pro Lys Pro Lys Asp Thr Leu
260 265 270

-continued

```
Met Ile Ser Arg Thr Pro Glu Val Thr Cys Val Val Val Asp Val Ser
        275                 280                 285

Gln Glu Asp Pro Glu Val Gln Phe Asn Trp Tyr Val Asp Gly Val Glu
    290                 295                 300

Val His Asn Ala Lys Thr Lys Pro Arg Glu Glu Gln Phe Asn Ser Thr
305                 310                 315                 320

Tyr Arg Val Val Ser Val Leu Thr Val Leu His Gln Asp Trp Leu Asn
                325                 330                 335

Gly Lys Glu Tyr Lys Cys Lys Val Ser Asn Lys Gly Leu Pro Ser Ser
            340                 345                 350

Ile Glu Lys Thr Ile Ser Lys Ala Lys Gly Gln Pro Arg Glu Pro Gln
        355                 360                 365

Val Tyr Thr Leu Pro Pro Ser Gln Glu Glu Met Thr Lys Asn Gln Val
    370                 375                 380

Ser Leu Thr Cys Leu Val Lys Gly Phe Tyr Pro Ser Asp Ile Ala Val
385                 390                 395                 400

Glu Trp Glu Ser Asn Gly Gln Pro Glu Asn Asn Tyr Lys Thr Thr Pro
                405                 410                 415

Pro Val Leu Asp Ser Asp Gly Ser Phe Phe Leu Tyr Ser Arg Leu Thr
            420                 425                 430

Val Asp Lys Ser Arg Trp Gln Glu Gly Asn Val Phe Ser Cys Ser Val
        435                 440                 445

Met His Glu Ala Leu His Asn His Tyr Thr Gln Lys Ser Leu Ser Leu
    450                 455                 460

Ser Leu Gly Lys
465


<210> SEQ ID NO 55
<211> LENGTH: 1794
<212> TYPE: DNA
<213> ORGANISM: Homo sapiens

<400> SEQUENCE: 55

atggaggcgg agccgccgct ctacccgatg gcgggggctg cggggccgca gggcgacgag      60

gacctgctcg gggtcccgga cgggcccgag gccccgctgg acgagctggt gggcgcgtac     120

cccaactaca acgaggagga ggaggagcgc cgctactacc gccgcaagcg cctgggcgtg     180

ctcaagaacg tgctggctgc cagcgccggg ggcatgctca cctacggcgt ctacctgggc     240

ctcctgcaga tgcagctgat cctgcactac gacgagacct accgcgaggt gaagtatggc     300

aacatggggc tgcccgacat cgacagcaaa atgctgatgg gcatcaacgt gactcccatc     360

gccgccctgc tctacacacc tgtgctcatc aggtttttg gaacgaagtg gatgatgttc     420

ctcgctgtgg gcatctacgc cctctttgtc tccaccaact actgggagcg ctactacacg     480

cttgtgccct cggctgtggc cctgggcatg gccatcgtgc ctctttgggc ttccatgggc     540

aactacatca ccaggatggc gcagaagtac catgagtact cccactacaa ggagcaggat     600

gggcagggga tgaagcagcg gcctccgcgg ggctcccacg cgccctatct cctggtcttc     660

caagccatct tctacagctt cttccatctg agcttcgcct gcgcccagct gcccatgatt     720

tatttcctga accactacct gtatgacctg aaccacacgc tgtacaatgt gcagagctgc     780

ggcaccaaca gccacgggat cctcagcggc ttcaacaaga cggttctgcg gacgctcccg     840

cggagcggaa acctcattgt ggtggagagc gtgctcatgg cagtggcctt cctggccatg     900

ctgctggtgc tgggtttgtg cggagccgct taccggccca cggaggagat cgatctgcgc     960
```

agcgtgggct ggggcaacat cttccagctg cccttcaagc acgtgcgtga ctaccgcctg 1020
cgccacctcg tgcctttctt tatctacagc ggcttcgagg tgctctttgc ctgcactggt 1080
atcgccttgg gctatggcgt gtgctcggtg gggctggagc ggctggctta cctcctcgtg 1140
gcttacagcc tgggcgcctc agccgcctca ctcctgggcc tgctgggcct gtggctgcca 1200
cgcccggtgc ccctggtggc cggagcaggg gtgcacctgc tgctcacctt catcctcttt 1260
ttctgggccc ctgtgcctcg ggtcctgcaa cacagctgga tcctctatgt ggcagctgcc 1320
ctttggggtg tgggcagtgc cctgaacaag actggactca gcacactcct gggaatcttg 1380
tacgaagaca aggagagaca ggacttcatc ttcaccatct accactggtg gcaggctgtg 1440
gccatcttca ccgtgtacct gggctcgagc ctgcacatga aggctaagct ggcggtgctg 1500
ctggtgacgc tggtggcggc cgcggtctcc tacctgcgga tggagcagaa gctgcgccgg 1560
ggcgtggccc cgcgccagcc ccgcatcccg cggccccagc acaaggtgcg cggttaccgc 1620
tacttggagg aggacaactc ggacgagagc gacgcggagg gcgagcatgg ggacggcgcg 1680
gaggaggagg cgccgcccgc agggcccagg cctggccccg agcccgctgg actcggccgc 1740
cggccctgcc cgtacgaaca ggcgcagggg ggagacgggc cggaggagca gtga 1794

<210> SEQ ID NO 56
<211> LENGTH: 3153
<212> TYPE: DNA
<213> ORGANISM: Mus musculus

<400> SEQUENCE: 56
atggtgtttt cgatgtggac acggaagaga caaattttga tctttttaaa tatgctctta 60
gtttctagag tctttgggtt tcgatggttt cctaaaactc taccttgtga agttaaagta 120
aatatcccag aggcccatgt gatcgtggac tgcacagaca agcatttgac agaaatccct 180
gagggcattc ccactaacac caccaatctt acccttacca tcaaccacat accaagcatc 240
tctccagatt ccttccgtag gctgaaccat ctggaagaaa tcgatttaag atgcaattgt 300
gtacctgttc tactggggtc caaagccaat gtgtgtacca agaggctgca gattagacct 360
ggaagcttta gtggactctc tgacttaaaa gccctttacc tggatggaaa ccaacttctg 420
gagataccac aggatctgcc atccagctta catcttctga gccttgaggc taacaacatc 480
ttctccatca cgaaggagaa tctaacagaa ctggtcaaca ttgaaacact ctacctgggt 540
caaaactgtt attatcgaaa tccttgcaat gtttcctatt ctattgaaaa agatgctttc 600
ctagttatga gaaatttgaa ggttctctca ctaaaagata acaatgtcac agctgtcccc 660
accactttgc cacctaattt actagagctc tatcttttata acaatatcat taagaaaatc 720
caagaaaatg attttaataa cctcaatgag ttgcaagttc ttgacctaag tggaaattgc 780
cctcgatgtt ataatgtccc atatccgtgt acaccgtgtg aaaataattc cccccttacag 840 atccatgaca atgctttcaa ttcattgaca gaattaaaag ttttacgttt acacagtaat 900
tctcttcagc atgtgccccc aacatggttt aaaaacatga gaaacctcca ggaactagac 960
ctctcccaaa actacttggc cagagaaatt gaggaggcca aatttttgca ttttcttccc 1020
aaccttgttg agttggattt ttctttcaat tatgagctgc aggtctacca tgcatctata 1080
actttaccac attcactctc ttcattggaa aacttgaaaa ttctgcgtgt caaggggtat 1140
gtctttaaag agctgaaaaa ctccagtctt tctgtattgc acaagcttcc caggctggaa 1200
gttcttgacc ttggcactaa cttcataaaa attgctgacc tcaacatatt caaacatttt 1260
gaaaacctca aactcataga cctttcagtg aataagatat ctccttcaga agagtcaaga 1320

-continued

```
gaagttggct tttgtcctaa tgctcaaact tctgtagacc gtcatgggcc ccaggtcctt   1380

gaggccttac actatttccg atacgatgaa tatgcacgga gctgcaggtt caaaaacaaa   1440

gagccacctt ctttcttgcc tttgaatgca gactgccaca tatatgggca gaccttagac   1500

ttaagtagaa ataacatatt ttttattaaa ccttctgatt ttcagcatct ttcattcctc   1560

aaatgcctca acttatcagg aaacaccatt ggccaaactc ttaatggcag tgaactctgg   1620

ccgttgagag agttgcggta cttagacttc tccaacaacc ggcttgattt actctactca   1680

acagcctttg aagagctcca gagtcttgaa gttctggatc taagtagtaa cagccactat   1740

tttcaagcag aaggaattac tcacatgcta aactttacca agaaattacg gcttctggac   1800

aaactcatga tgaatgataa tgacatctct acttcggcca gcaggaccat ggaaagtgac   1860

tctcttcgaa ttctggagtt cagaggcaac catttagatg ttctatggag agccggtgat   1920

aacagatact tggacttctt caagaatttg ttcaatttag aggtattaga tatctccaga   1980

aattccctga attccttgcc tcctgaggtt tttgagggta tgccgccaaa tctaaagaat   2040

ctctccttgg ccaaaaatgg gctcaaatct ttcttttggg acagactcca gttactgaag   2100

catttggaaa ttttggacct cagccataac cagctgacaa aagtacctga gagattggcc   2160

aactgttcca aaagtctcac aacactgatt cttaagcata atcaaatcag gcaattgaca   2220

aaatattttc tagaagatgc tttgcaattg cgctatctag acatcagttc aaataaaatc   2280

caggtcattc agaagactag cttcccagaa aatgtcctca acaatctgga gatgttggtt   2340

ttacatcaca atcgctttct ttgcaactgt gatgctgtgt ggtttgtctg gtgggttaac   2400

catacagatg ttactattcc atacctggcc actgatgtga cttgtgtagg tccaggagca   2460

cacaaaggtc aaagtgtcat atcccttgat ctgtatacgt gtgagttaga tctcacaaac   2520

ctgattctgt tctcagtttc catatcatca gtcctctttc ttatggtagt tatgacaaca   2580

agtcacctct ttttctggga tatgtggtac atttattatt tttggaaagc aaagataaag   2640

gggtatcagc atctgcaatc catggagtct tgttatgatg cttttattgt gtatgacact   2700

aaaaactcag ctgtgacaga atgggttttg caggagctgg tggcaaaatt ggaagatcca   2760

agagaaaaac acttcaattt gtgtctagaa gaaagagact ggctaccagg acagccagtt   2820

ctagaaaacc tttcccagag catacagctc agcaaaaaga cagtgtttgt gatgacacag   2880

aaatatgcta agactgagag ttttaagatg gcattttatt tgtctcatca gaggctcctg   2940

gatgaaaaag tggatgtgat tatcttgata ttcttggaaa agcctcttca gaagtctaag   3000

tttcttcagc tcaggaagag actctgcagg agctctgtcc ttgagtggcc tgcaaatcca   3060

caggctcacc catacttctg gcagtgcctg aaaaatgccc tgaccacaga caatcatgtg   3120

gcttatagtc aaatgttcaa ggaaacagtc tag                                3153
```

<210> SEQ ID NO 57
<211> LENGTH: 3153
<212> TYPE: DNA
<213> ORGANISM: Rattus norvegicus

<400> SEQUENCE: 57

```
atggtatttc caatgtggac attgaagaga caaagtttta tctttttaaa tatgatctta     60

gtttctagag tccttgggtt tcgatggtat cctaaaactc taccttgtga tgtctctctc    120

gatagcacaa acacccatgt gattgtggat tgcacagaca agcatttgac agaaatacct    180

gagggtattc ccactaatac caccaacctt acccttacca tcaaccacat accaagcatc    240

tctccagact ccttccatag gctgaagcat ctggaggagc ttgatttaag atgcaactgt    300
```

-continued

```
gtacctattc tactggggtc caaagccaat gtgtgcacca agaggctaca gattagacct    360

ggaagcttta gtggactctc tgacttaaaa tccctttacc tggatggaaa tcaacttcta    420

gagataccac aggatcttcc atcaagctta cagcttctga gccttgaggc taacaatatc    480

ttctccatca caaaggagaa tctatcagaa ctagtcaaca ttgaatcact ctacctgggc    540

caaaactgtt attatcgaaa tccttgcaat gtttcctatt ctattgaaaa agatgctttc    600

ctagttatga aaaatttaaa ggttctctca ctaaaagata acaatgtcac agctgtcccc    660

accattttgc cacctaattt gctagaactc tatctttata acaacatcat taagagaatc    720

caagaacatg attttaataa gctcagccag ttgcaagttc ttgacctaag tggaaactgc    780

cctcgatgtt ataatgtccc atatccatgt acaccatgtg aaaataattc tcccttacag    840

atccatgaca atgcttttga ttcattaaca gaattaaaag ttttacgtct acacagtaac    900

tctcttcagc atgtgcctgc agaatggttt aaaaacatga gcaacctcca ggaactagac    960

ctctcccaaa actacttagc cagagaaatt gaagaagcca atttttgaa ttctctcccc   1020

aaccttgtcc agttggatct gtctttcaat tatgagctgc aggtctacca tgcatctatt   1080

actttaccac actcactctc ttcattgaca aagttgaaaa atctgtatat caagggatat   1140

gtctttaaag agctgaaaga ctccagcctt tctgtattgc acaacctttc caatctagaa   1200

gttcttgacc ttggcactaa cttcataaaa attgctgacc tcaacatatt ccaacagttt   1260

gaaaacctca aattcataga cctttcagtg aataagatat ccccctcaga agagtcaaga   1320

gaagttggtt tatgtcctaa tgcccaaact tctgtagact ggcacggacc ccaggtcctt   1380

gaggccttac actatttccg atatgatgaa tatgcacgga gctgcaggtt caaaaacaaa   1440

gagccgccta ctttttgcc tttgaatgca gactgccaca catatgggaa gaccttagac   1500

ctaagtagaa ataacatatt ttttattaaa ccctctgatt ttaagcatct ttcattcctg   1560

aaatgcctca atttgtcagg aaacgccatt ggccaaactc ttaatggcag tgaactccag   1620

cccttgagag agctgcggta cttagacttc tccaacaacc ggcttgattt actctactca   1680

acagcctttg aagagctcca gaatctggaa attctggatc taagtagtaa cagccactat   1740

tttcaagcag aaggaattac tcacatgcta aactttacca agaaattacg gcatctagag   1800

aaactcatga tgaatgacaa tgacatctct acttcagcca gcaggaccat ggaaagtgaa   1860

tctcttcgtg ttctggaatt cagaggcaac catttagatg ttctatggag agatggtgat   1920

aacagatact tggacttctt caagaatctg ctcaacttag aggaattaga tatctccaga   1980

aattccctga attccgtgcc tcctggagtt tttgagggta tgccaccgaa tctaacgact   2040

ctctccttag ccaaaaatgg actcagatct ttctcttggg gtagacttca gttactaaag   2100

catttgaaaa atttggacct cagccacaac cagctgacaa ctgtccctgc gagattggcc   2160

aactgttcca aaagtctcac aaaactgatt cttaatcata atcaaatcag gcagttgaca   2220

aaatatttttc tagaagatgc tttgcaattg cgctatctag acatcagttc aaataagatc  2280

caggtcattc agaagactag cttcccagaa aacgtcctca acaatctgaa catgttgctt   2340

ttacatcaca atcgctttct ttgcaactgt gatgctgtgt ggtttgtctg gtgggttaat   2400

catacagatg ttactattcc atacctggcc actgatgtga cttgtgcagg tccaggcgca   2460

cacaaaggtc aaagtgtcat atctctggat ctatatacat gtgaattaga tctcacaaac   2520

ctgattctgt tctcagtttc catatcatca gtcctctttc ttatgatagt tatgacaaca   2580

agtcacctct tttctggga tatgtggtac atttattatt tctggaaagc caagataaag    2640

ggttatcaac atctgcaatc aatggagtct tgttatgatg cttttattgt gtatgacact   2700
```

```
aaaaactcag ctgtgacaga atgggttttg caggagctgg tggttaaatt ggaagaccca   2760

agagaaaaac actttaattt gtgtctagaa gaaagagact ggctaccagg gcagccagtt   2820

ctagaaaacc tttcccagag catacagctc agcagaaaga cagtgtttgt gatgacacag   2880

aaatatgcga agactgagag ttttaagatg gcgttttatt tgtcccatca gaggcttatg   2940

gatgaaaagg tggatgtgat tatcttgata ttcttggaaa agcctcttca gaagtctaag   3000

tttcttcagc tccggaagag gctctgcagc agttctgtcc ttgagtggcc tacaaatcca   3060

caagctcacc catatttctg gcagtgcctg aaaaatgccc tgactacaga caatcatgtg   3120

gcttatagtc aaatgttcaa ggaaacagtc tag                                 3153
```

<210> SEQ ID NO 58
<211> LENGTH: 3150
<212> TYPE: DNA
<213> ORGANISM: Macaca mulatta

<400> SEQUENCE: 58

```
atgatgttcc ctgtgtggac cctgaagcgg cagatcctga ttctgttcaa tattatcctg     60

atttctaaac tgctgggggc aaggtggttc cccaagactc tgccttgcga cgtgaccctg    120

gatgtcagca agaaccacgt gatcgtcgac tgtacagata aacatctgac tgagattcca    180

ggcggcatcc ccaccaacac cacaaatctg accctgacaa tcaatcacat tcctgacatc    240

tctccagcca gttttcaccg gctggtgcat ctggtcgaga ttgatttccg atgcaactgt    300

gtgcctatcc ggctgggaag caagtccaat atgtgccctc ggagactgca gatcaagcca    360

agatctttta gtggcctgac ctacctgaag agcctgtatc tggacggaaa ccagctgctg    420

gagatcccac agggactgcc accttccctg cagctgctgt ctctggaagc caacaatatt    480

ttctccatca ggaaggagaa cctgacagaa ctggctaata tcgagattct gtacctgggc    540

cagaactgct actatcgcaa tccctgttac gtgtcatata gcatcgaaaa agacgccttt    600

ctgaacctga ctaagctgaa agtcctgtct ctgaaggata acaatgtgac taccgtcccc    660

accgtgctgc ctagtactct gaccgagctg tacctgtata acaatatgat tgcagagatc    720

caggaagacg atttcaacaa tctgaaccag ctgcagattc tggacctgag tggaaactgc    780

cccaggtgtt acaatgctcc ctttccttgc acaccttgta agaacaattc tccactgcag    840

atccccgtca atgcattcga tgccctgact gagctgaaag tgctgcggct gcactccaac    900

tctctgcagc atgtcccacc cagatggttt aagaatatca acaatctgca ggagctggac    960

ctgagccaga acttcctggc caaggaaatt ggcgatgcta aattcctgca ctttctgcca   1020

aacctgatcc agctggacct gagcttcaat tttgagctgc aggtgtaccg ggcatctatg   1080

aacctgagtc aggcctttag ctccctgaaa agcctgaaga ttctgcggat cagaggctat   1140

gtgtttaaag agctgaagtc attcaatctg agcccccctgc ataacctgca gaatctggaa   1200

gtgctggatc tgggaaccaa cttcatcaaa attgccaatc tgagcatgtt caaacagttt   1260

aagagactga aagtgattga cctgtccgtc aacaagatca gtccctcagg cgattctagt   1320

gaagtggggt tttgcagcaa tgctcgaaca tcagtcgaga gctacgaacc tcaggtgctg   1380

gaacagctgt actatttcag atacgacaaa tatgccagat catgcaggtt taagaacaaa   1440

gaggcttcct tcacatctgt gaatgaaagc tgttacaagt atgggcagac tctggacctg   1500

agtaagaact caattttctt tatcaaatca agcgatttcc agcacctgtc ctttctgaag   1560

tgtctgaacc tgagtgggaa tctgatctca cagactctga atggatctga gtttcagcct   1620

ctggctgaac tgagatacct ggacttctca aacaataggc tggatctgct gcatagcacc   1680
```

gcattcgagg aactgaggaa actggaggtg ctggacattt cctctaacag ccactatttt 1740
cagtccgaag gaatcacaca tatgctgaac ttcactaaga atctgaaagt gctgcagaag 1800
ctgatgatga acgacaatga catcagcagc agcacatccc gcactatgga gagcgaatcc 1860
ctgcgcaccc tggagtttcg aggcaaccac ctggatgtgc tgtggcggga cggggataac 1920
agatacctgc agctgttcaa gaatctgctg aaactggagg aactggacat ttccaaaaac 1980
tctctgagtt ttctgccctc tggggtgttc gatggaatgc ctccaaacct gaagaatctg 2040
tctctggcca agaatggcct gaaaagtttt atctgggaga agctgaggta tctgaaaaac 2100
ctggaaacac tggacctgag tcacaatcag ctgacaactg tgcctgagag gctgtcaaac 2160
tgctcacgca gcctgaagaa tctgattctg aaaaacaatc agatcaggtc tctgactaaa 2220
tacttcctgc aggacgcctt tcagctgcgc tatctggatc tgtcctctaa taagattcag 2280
atgatccaga aaaccagctt ccctgagaac gtgctgaaca atctgaagat gctgctgctg 2340
caccataatc gctttctgtg cacatgtgac gccgtctggt tcgtgtggtg ggtcaaccac 2400
accgaggtga caattccata cctggcaact gatgtgacct gcgtcggacc aggagcacat 2460
aagggacaga gcgtgatctc cctggacctg tatacctgtg aactggatct gacaaatctg 2520
attctgtttt ccctgtctat cagtgtctca ctgttcctga tggtcatgat gaccgcaagc 2580
cacctgtact tttgggatgt gtggtacatc taccatttct gcaaggccaa aattaagggc 2640
tatcagcggc tgatctcccc tgactgctgt tacgatgctt ttatcgtgta tgacactaag 2700
gaccccgcag tgaccgagtg ggtcctggct gaactggtcg caaagctgga ggacccacgc 2760
gaaaaacact tcaacctgtg tctggaggaa cgagattggc tgccagggca gcccgtgctg 2820
gagaatctga gccagtccat ccagctgtcc aagaaaaccg tgttcgtcat gacagacaag 2880
tacgctaaga ccgaaaactt caagatcgca ttctatctgt ctcatcagag actgatggac 2940
gagaaagtgg atgtcatcat tctgatcttc ctggaaaagc catttcagaa aagcaagttc 3000
ctgcagctgc gaaagcggct gtgcggcagt tcagtgctgg agtggcctac aaacccacag 3060
gcccacccct acttttggca gtgtctgaaa aacgccctgg ctaccgataa tcatgtggct 3120
tatagccagg tcttcaagga aacagtgtag 3150

<210> SEQ ID NO 59
<211> LENGTH: 449
<212> TYPE: DNA
<213> ORGANISM: Homo sapiens

<400> SEQUENCE: 59
gcctccggac tctagagcca ccatggtgct gcagacccag gtgttcatct ccctgctgct 60
gtggatctcc ggcgcgtacg gcgatatcgt gatgattaaa cgtacggtgg ccgccccctc 120
cgtgttcatc ttcccccct ccgacgagca gctgaagtcc ggcaccgcct ccgtggtgtg 180
cctgctgaat aacttctacc ccagagaggc caaggtgcag tggaaggtgg acaacgccct 240
gcagtccggg aactcccagg agagcgtgac cgagcaggac agcaaggaca gcacctacag 300
cctgagcagc accctgaccc tgagcaaagc cgactacgag aagcacaagg tgtacgcctg 360
cgaggtgacc caccagggcc tgagctcccc cgtcaccaag agcttcaaca gggggagtg 420 ttaggggccc gtttaaacgg gggaggcta 449

<210> SEQ ID NO 60
<211> LENGTH: 1132
<212> TYPE: DNA
<213> ORGANISM: Homo sapiens

<400> SEQUENCE: 60

```
gcctccggac tctagagcca ccatgaaaca cctgtggttc ttcctcctgc tggtggcagc     60
tcccagatgg gtgctgagcc aggtgcaatt gtgcaggcgg ttagctcagc ctccaccaag    120
ggcccaagcg tcttcccccct ggcaccctcc tccaagagca cctctggcgg cacagccgcc    180
ctgggctgcc tggtcaagga ctacttcccc gaacccgtga ccgtgagctg gaactcaggc    240
gccctgacca gcggcgtgca caccttcccc gctgtcctgc agtcctcagg actctactcc    300
ctcagcagcg tggtgaccgt gccctccagc agcttgggca cccagaccta catctgcaac    360
gtgaatcaca agcccagcaa caccaaggtg gacaagagag ttgagcccaa atcttgtgac    420
aaaactcaca catgcccacc ctgcccagca cctgaactcc tggggggacc ctcagtcttc    480
ctcttccccc caaaacccaa ggacaccctc atgatctccc ggacccctga ggtcacatgc    540
gtggtggtgg acgtgagcca cgaagaccct gaggtcaagt tcaactggta cgtggacggc    600
gtggaggtgc ataatgccaa gacaaagccc cgggaggagc agtacaacag cacgtaccgg    660
gtggtcagcg tcctcaccgt cctgcaccag gactggctga atggcaagga gtacaagtgc    720
aaggtctcca acaaagccct cccagccccc atcgagaaaa ccatctccaa agccaaaggc    780
cagccccggg aaccacaggt gtacaccctg cccccatccc gggaggagat gaccaagaac    840
caggtcagcc tgacctgcct ggtcaaaggc ttctatccca gcgacatcgc cgtggagtgg    900
gagagcaatg gccagcccga gaacaactac aagaccaccc ctcccgtgct ggactccgac    960
ggctccttct tcctctacag caagctcacc gtggacaaga gcaggtggca gcagggcaac   1020
gtcttctcat gctccgtgat gcatgaggct ctgcacaacc actacaccca gaagagcctc   1080
tccctgtctc ccggcaaatg agatatcggg cccgtttaaa cgggggaggc ta           1132
```

<210> SEQ ID NO 61
<211> LENGTH: 1395
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1395)
<223> OTHER INFORMATION: Nucleotid sequence encoding heavy chain of cAT01 antibody

<400> SEQUENCE: 61

```
atgaaacacc tgtggttctt cctcctgctg gtggcagctc ccagatgggt gctgagccag     60
gtgcagctgc agcagcctgg cgccgaactc gtgaaacctg gcgcctccgt gaacctgagc    120
tgcaaggcca gcggctacac cttcaccaac aactggctgc actgggtcaa gcagaggccc    180
ggcagaggcc tggaatggat cggcgacatc taccccagca acggccggac caactacaac    240
gagcagttca agaccaaggc caccctgacc gtggacaaga gcagcagcac cgcctacatg    300
cagctgtcca gcctgaccag cgaggacagc gccgtgtact tctgcgccag agagcggggc    360
tacttcgact attggggcca gggaaccgct ctgaccgtca gctcagcctc caccaagggc    420
ccaagcgtct tccccctggc accctcctcc aagagcacct ctggcggcac agccgccctg    480
ggctgcctgg tcaaggacta cttccccgaa cccgtgaccg tgagctggaa ctcaggcgcc    540
ctgaccagcg gcgtgcacac cttccccgct gtcctgcagt cctcaggact ctactccctc    600
agcagcgtgg tgaccgtgcc ctccagcagc ttgggcaccc agacctacat ctgcaacgtg    660
aatcacaagc ccagcaacac caaggtggac aagagagttg agcccaaatc ttgtgacaaa    720
```

```
actcacacat gcccaccctg cccagcacct gaactcctgg ggggaccctc agtcttcctc    780

ttcccccaa aacccaagga caccctcatg atctcccgga cccctgaggt cacatgcgtg    840

gtggtggacg tgagccacga agaccctgag gtcaagttca actggtacgt ggacggcgtg    900

gaggtgcata atgccaagac aaagccccgg gaggagcagt acaacagcac gtaccgggtg    960

gtcagcgtcc tcaccgtcct gcaccaggac tggctgaatg gcaaggagta caagtgcaag   1020

gtctccaaca aagccctccc agcccccatc gagaaaacca tctccaaagc caaaggccag   1080

ccccgggaac cacaggtgta caccctgccc ccatcccggg aggagatgac caagaaccag   1140

gtcagcctga cctgcctggt caaaggcttc tatcccagcg acatcgccgt ggagtgggag   1200

agcaatggcc agcccgagaa caactacaag accacccctc ccgtgctgga ctccgacggc   1260

tccttcttcc tctacagcaa gctcaccgtg gacaagagca ggtggcagca gggcaacgtc   1320

ttctcatgct ccgtgatgca tgaggctctg cacaaccact acacccagaa gagcctctcc   1380

ctgtctcccg gcaaa                                                    1395
```

```
<210> SEQ ID NO 62
<211> LENGTH: 749
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(749)
<223> OTHER INFORMATION: Nucleotid sequence of DNA fragment containing a
      nucleotide sequence encoding light chain of cAT01 antibody

<400> SEQUENCE: 62

ccagcctccg gactctagag ccaccatggt gctgcagacc caggtgttca tcagcctgct     60

gctgtggatc agcggcgcct acggcgacat ccagatgacc cagagcccta gcagcctgag    120

cacaagcctg ggcggcaaag tgaccatcac atgcaaggcc agccaggaca tcaacaagta    180

tatcgcctgg tatcagcaca aacccggcaa gggccccaga ctgctgattc actacaccag    240

caccctgcag cccggcatcc ccagcagatt ttctggcagc ggctccggca gagactacag    300

cttcagcatc agcaacctgg aacccgagga tatcgccacc tactactgcc tgcagtacga    360

ctacctgctg accttcggag ccggcaccaa gctggaactg aagagagccg tggccgctcc    420

ctccgtgttc atcttcccac ctagcgacga gcagctgaag tccggcacag cctctgtcgt    480

gtgcctgctg aacaacttct acccccgcga ggccaaggtg cagtggaagg tggacaatgc    540

cctgcagagc ggcaacagcc aggaaagcgt gaccgagcag gacagcaagg actccaccta    600

cagcctgtcc tccaccctga ccctgagcaa ggccgactac gagaagcaca aggtgtacgc    660

ctgcgaagtg acccaccagg gcctgagcag ccctgtgacc aagagcttca accggggcga    720

gtgctgagtt taaacggggg aggctaact                                      749
```

```
<210> SEQ ID NO 63
<211> LENGTH: 1413
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1413)
<223> OTHER INFORMATION: Nucleotid sequence encoding heavy chain of cNB7
      antibody
```

<400> SEQUENCE: 63

```
atgaaacacc tgtggttctt cctcctgctg gtggcagctc ccagatgggt gctgagcgac     60
gtgcagctgc aggaatctgg ccctggcctc gtgaagccta gccagagcct gagcctgaca    120
tgcaccgtga ccggctacag catcaccagc gactacgcct ggaactggat ccggcagttc    180
cccggcaaca agctggaatg gatgggccac atcagctacc ggggcaacac caactacaac    240
cccagcctga agtcccggat ctccatcacc cgggacacca gcaagaacca gttctttctg    300
cagctgaaca gcgtgaccac cgaggacacc gccacctact actgcgccag ctggaactac    360
tacggctacg tggactatgc catggactac tggggccagg gcacctccgt gaccgtcagc    420
tcagcctcca ccaagggccc aagcgtcttc cccctggcac cctcctccaa gagcacctct    480
ggcggcacag ccgccctggg ctgcctggtc aaggactact tccccgaacc cgtgaccgtg    540
agctggaact caggcgccct gaccagcggc gtgcacacct tccccgctgt cctgcagtcc    600
tcaggactct actccctcag cagcgtggtg accgtgccct ccagcagctt gggcacccag    660
acctacatct gcaacgtgaa tcacaagccc agcaacacca aggtggacaa gagagttgag    720
cccaaatctt gtgacaaaac tcacacatgc ccaccctgcc cagcacctga actcctgggg    780
ggaccctcag tcttcctctt ccccccaaaa cccaaggaca ccctcatgat ctcccggacc    840
cctgaggtca catgcgtggt ggtggacgtg agccacgaag accctgaggt caagttcaac    900
tggtacgtgg acggcgtgga ggtgcataat gccaagacaa agccccggga ggagcagtac    960
aacagcacgt accgggtggt cagcgtcctc accgtcctgc accaggactg gctgaatggc   1020
aaggagtaca agtgcaaggt ctccaacaaa gccctcccag cccccatcga gaaaaccatc   1080
tccaaagcca aaggccagcc ccgggaacca caggtgtaca ccctgccccc atcccgggag   1140
gagatgacca agaaccaggt cagcctgacc tgcctggtca aaggcttcta tcccagcgac   1200
atcgccgtgg agtgggagag caatggccag cccgagaaca actacaagac cacccctccc   1260
gtgctggact ccgacggctc cttcttcctc tacagcaagc tcaccgtgga caagagcagg   1320
tggcagcagg gcaacgtctt ctcatgctcc gtgatgcatg aggctctgca caaccactac   1380
acccagaaga gcctctccct gtctcccggc aaa                                1413
```

<210> SEQ ID NO 64
<211> LENGTH: 749
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(749)
<223> OTHER INFORMATION: Nucleotid sequence of DNA fragment containing a nucleotide sequence encoding light chain of cNB7 antibody

<400> SEQUENCE: 64

```
ccagcctccg gactctagag ccaccatggt gctgcagacc caggtgttca tcagcctgct     60
gctgtggatc agcggcgcct acggcgacat ccagatgacc cagacaccca gcagcctgag    120
cgccagcctg ggcgatagag tgaccatcag ctgcagagcc agccaggaca tcagcaacta    180
cctgaactgg tatcagcaga aacccgacgg caccgtgaag ctgctgatct actacaccag    240
cagactgcac agcggcgtgc ccagcagatt ttctggcagc ggctccggca ccgactacag    300
cctgaccatc aacaacctgg aacaggaaga tatcgctacc tacttctgtc agcaaggcga    360
caccttcccc accttcggcg gaggcaccaa gctggaaatc aagagagccg tggccgctcc    420
```

```
ctccgtgttc atcttcccac ctagcgacga gcagctgaag tctggcacag ccagcgtcgt    480

gtgcctgctg aacaacttct acccccgcga ggccaaggtg cagtggaagg tggacaatgc    540

cctgcagagc ggcaacagcc aggaaagcgt gaccgagcag gacagcaagg actccaccta    600

ctccctgagc agcaccctga ccctgagcaa ggccgactac gagaagcaca aggtgtacgc    660

ctgcgaagtg acccaccagg gcctgtctag ccccgtgacc aagagcttca accggggcga    720

gtgttgagtt taaacggggg aggctaact                                      749


<210> SEQ ID NO 65
<211> LENGTH: 1410
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1410)
<223> OTHER INFORMATION: Nucleotid sequence encoding heavy chain of
      cFAN2 antibody

<400> SEQUENCE: 65

atgaaacacc tgtggttctt cctcctgctg gtggcagctc ccagatgggt gctgagccag     60

gtgcagctga aagagtctgg ccctggactg gtggccccta gccagagcct gagcatcacc    120

tgtaccgtgt ccggcttcag cctgaccggc tacggcgtga actgggtgcg ccagcctcct    180

ggcaaaggcc tggaatggct gggcatgatc tggggcgacg gcagcaccga ctacaacagc    240

gccctgaagt cccggctgag catccggaag gacaacagca agtcccaggt gttcctgaag    300

atgaacagcc tgcagaccga cgacaccgcc cggtactact gcgccagaga caagggctac    360

gacggctact actacgccat ggactactgg ggccagggca cctctgtgac cgtcagctca    420

gcctccacca agggcccaag cgtcttcccc ctggcaccct cctccaagag cacctctggc    480

ggcacagccg ccctgggctg cctggtcaag gactacttcc ccgaacccgt gaccgtgagc    540

tggaactcag gcgccctgac cagcggcgtg cacaccttcc ccgctgtcct gcagtcctca    600

ggactctact ccctcagcag cgtggtgacc gtgccctcca gcagcttggg cacccagacc    660

tacatctgca acgtgaatca caagcccagc aacaccaagg tggacaagag agttgagccc    720

aaatcttgtg acaaaactca cacatgccca ccctgcccag cacctgaact cctgggggga    780

ccctcagtct tcctcttccc cccaaaaccc aaggacaccc tcatgatctc ccggacccct    840

gaggtcacat gcgtggtggt ggacgtgagc cacgaagacc ctgaggtcaa gttcaactgg    900

tacgtggacg gcgtggaggt gcataatgcc aagacaaagc cccgggagga gcagtacaac    960

agcacgtacc gggtggtcag cgtcctcacc gtcctgcacc aggactggct gaatggcaag   1020

gagtacaagt gcaaggtctc caacaaagcc ctcccagccc ccatcgagaa aaccatctcc   1080

aaagccaaag gccagccccg ggaaccacag gtgtacaccc tgcccccatc ccgggaggag   1140

atgaccaaga accaggtcag cctgacctgc ctggtcaaag gcttctatcc cagcgacatc   1200

gccgtggagt gggagagcaa tggccagccc gagaacaact acaagaccac ccctcccgtg   1260

ctggactccg acggctcctt cttcctctac agcaagctca ccgtggacaa gagcaggtgg   1320

cagcagggca acgtcttctc atgctccgtg atgcatgagg ctctgcacaa ccactacacc   1380

cagaagagcc tctccctgtc tcccggcaaa                                    1410
```

<210> SEQ ID NO 66
<211> LENGTH: 752
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(752)
<223> OTHER INFORMATION: Nucleotid sequence of DNA fragment containing a nucleotide sequence encoding light chain of cFAN2 antibody

<400> SEQUENCE: 66
ccagcctccg gactctagag ccaccatggt gctgcagacc caggtgttca tcagcctgct 60
gctgtggatc agcggcgcct acggcgacat ccagatgaca cagtctcccg ccagcctgag 120
cgcctctgtg ggagagacag tgaccatcac ctgtcgggcc agcgagaaca tctacagcta 180
cctggcctgg tatcagcaga agcagggcaa gagcccccag ctgctggtgt acgatgccaa 240
gacactggcc gagggcgtgc ccagcagatt ttctggcagc ggctccggca cccagttcag 300
cctgaagatc aacagcctgc agcccgagga cttcggcagc tactactgcc agcaccacta 360
cggcatccct tacaccttcg gcggaggcac caagctggaa atcaagagag ccgtggccgc 420
tccctccgtg ttcatcttcc cacctagcga cgagcagctg aagtccggca cagctagcgt 480
cgtgtgcctg ctgaacaact tctacccccg cgaggccaag gtgcagtgga aggtggacaa 540
tgccctgcag agcggcaaca gccaggaaag cgtgaccgag caggacagca aggactccac 600
ctacagcctg tccagcaccc tgaccctgag caaggccgac tacgagaagc acaaggtgta 660
cgcctgcgaa gtgacccacc agggcctgag cagcccagtg accaagagct tcaaccgggg 720
cgagtgctga gtttaaacgg gggaggctaa ct 752

<210> SEQ ID NO 67
<211> LENGTH: 1395
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1395)
<223> OTHER INFORMATION: Nucleotid sequence encoding huAT01_H1_IgG1LALA

<400> SEQUENCE: 67
atgaaacacc tgtggttctt cctcctgctg gtggcagctc ccagatgggt gctgagccag 60
gtgcagctgg tgcagtctgg cgccgaagtg aagaaaccag gcgccagcgt gaaggtgtcc 120
tgcaaggcca gcggctacac ctttaccaac aactggctgc actgggtgcg ccaggctcca 180
ggacagggac tggaatggat gggcgacatc taccccagca acggccggac caactacgcc 240
cagaaattcc agggcagagt gaccatcacc gccgacaaga gcaccagcac cgcctacatg 300
gaactgagca gcctgcggag cgaggacacc gccgtgtact actgcgccag agagcggggc 360
tacttcgact attggggcca gggcacactc gtgaccgtca gctcagcctc caccaagggc 420
ccaagcgtct tccccctggc accctcctcc aagagcacct ctggcggcac agccgccctg 480
ggctgcctgg tcaaggacta cttccccgaa cccgtgaccg tgagctggaa ctcaggcgcc 540
ctgaccagcg gcgtgcacac cttccccgct gtcctgcagt cctcaggact ctactccctc 600
agcagcgtgg tgaccgtgcc ctccagcagc ttgggcaccc agacctacat ctgcaacgtg 660
aatcacaagc ccagcaacac caaggtggac aagagagttg agcccaaatc ttgtgacaaa 720
actcacacat gcccaccctg cccagcacct gaagccgcgg ggggaccctc agtcttcctc 780

-continued ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccccgg gaggagcagt acaacagcac gtaccgggtg 960
gtcagcgtcc tcaccgtcct gcaccaggac tggctgaatg gcaaggagta caagtgcaag 1020
gtctccaaca aagccctccc agcccccatc gagaaaacca tctccaaagc caaaggccag 1080
ccccgggaac cacaggtgta caccctgccc ccatcccggg aggagatgac caagaaccag 1140
gtcagcctga cctgcctggt caaaggcttc tatcccagcg acatcgccgt ggagtgggag 1200
agcaatggcc agcccgagaa caactacaag accacccctc ccgtgctgga ctccgacggc 1260
tccttcttcc tctacagcaa gctcaccgtg gacaagagca ggtggcagca gggcaacgtc 1320
ttctcatgct ccgtgatgca tgaggctctg cacaaccact acacccagaa gagcctctcc 1380
ctgtctcccg gcaaa 1395

<210> SEQ ID NO 68
<211> LENGTH: 1395
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1395)
<223> OTHER INFORMATION: Nucleotid sequence encoding huAT01_H3_IgG1LALA

<400> SEQUENCE: 68
atgaaacacc tgtggttctt cctcctgctg gtggcagctc ccagatgggt gctgagccag 60
gtgcagctgg tgcagtctgg cgccgaagtg aagaaaccag gcgccagcgt gaaggtgtcc 120
tgcaaggcca gcggctacac ctttaccaac aactggctgc actgggtgcg ccaggctcca 180
ggacagggac tggaatggat gggcgacatc taccccagca acggccggac caactacgcc 240
cagaaattcc agggcagagt gaccctgacc gtggacaaga gcaccagcac cgcctacatg 300
gaactgagca gcctgcggag cgaggatacc gccgtgtact tctgtgccag agagcggggc 360
tacttcgact actggggcca gggaacactc gtgaccgtca gctcagcctc caccaagggc 420
ccaagcgtct tcccctggc accctcctcc aagagcacct ctggcggcac agccgccctg 480
ggctgcctgg tcaaggacta cttccccgaa cccgtgaccg tgagctggaa ctcaggcgcc 540
ctgaccagcg gcgtgcacac cttccccgct gtcctgcagt cctcaggact ctactccctc 600
agcagcgtgg tgaccgtgcc ctccagcagc ttgggcaccc agacctacat ctgcaacgtg 660
aatcacaagc ccagcaacac caaggtggac aagagagttg agcccaaatc ttgtgacaaa 720
actcacacat gcccaccctg cccagcacct gaagccgcgg ggggaccctc agtcttcctc 780
ttccccccaa aacccaagga caccctcatg atctcccgga cccctgaggt cacatgcgtg 840
gtggtggacg tgagccacga agaccctgag gtcaagttca actggtacgt ggacggcgtg 900
gaggtgcata atgccaagac aaagccccgg gaggagcagt acaacagcac gtaccgggtg 960
gtcagcgtcc tcaccgtcct gcaccaggac tggctgaatg gcaaggagta caagtgcaag 1020
gtctccaaca aagccctccc agcccccatc gagaaaacca tctccaaagc caaaggccag 1080
ccccgggaac cacaggtgta caccctgccc ccatcccggg aggagatgac caagaaccag 1140
gtcagcctga cctgcctggt caaaggcttc tatcccagcg acatcgccgt ggagtgggag 1200
agcaatggcc agcccgagaa caactacaag accacccctc ccgtgctgga ctccgacggc 1260
tccttcttcc tctacagcaa gctcaccgtg gacaagagca ggtggcagca gggcaacgtc 1320

-continued

```
ttctcatgct ccgtgatgca tgaggctctg cacaaccact acacccagaa gagcctctcc   1380

ctgtctcccg gcaaa                                                    1395


<210> SEQ ID NO 69
<211> LENGTH: 1386
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1386)
<223> OTHER INFORMATION: Nucleotid sequence encoding huAT01_H3_IgG4Pro

<400> SEQUENCE: 69

atgaaacacc tgtggttctt cctcctgctg gtggcagctc ccagatgggt gctgagccag     60

gtgcagctgg tgcagtctgg cgccgaagtg aagaaaccag gcgccagcgt gaaggtgtcc    120

tgcaaggcca gcggctacac ctttaccaac aactggctgc actgggtgcg ccaggctcca    180

ggacagggac tggaatggat gggcgacatc taccccagca acggccggac caactacgcc    240

cagaaattcc agggcagagt gaccctgacc gtggacaaga gcaccagcac cgcctacatg    300

gaactgagca gcctgcggag cgaggatacc gccgtgtact tctgtgccag agagcggggc    360

tacttcgact actggggcca gggaacactc gtgaccgtca gctcagcctc caccaagggc    420

cctagcgtgt tccctctggc cccttgtagc agaagcacca gcgagtctac agccgccctg    480

ggctgcctcg tgaaggacta ctttcccgag cccgtgaccg tgtcctggaa ctctggcgct    540

ctgacaagcg gcgtgcacac ctttccagcc gtgctgcaga gcagcggcct gtactctctg    600

tccagcgtcg tgactgtgcc cagcagctct ctgggcacca agacctacac ctgtaacgtg    660

gaccacaagc ccagcaacac caaggtggac aagcgggtgg aatctaagta cggccctccc    720

tgccctcctt gcccagcccc tgaatttctg ggcggaccct ccgtgttcct gttcccccca    780

aagcccaagg acaccctgat gatcagccgg acccccgaag tgacctgcgt ggtggtggat    840

gtgtcccagg aagatcccga ggtgcagttc aattggtacg tggacggcgt ggaagtgcac    900

aacgccaaga ccaagcctag agaggaacag ttcaacagca cctaccgggt ggtgtccgtg    960

ctgacagtgc tgcaccagga ctggctgaac ggcaaagagt acaagtgcaa ggtgtccaac   1020

aagggcctgc ccagctccat cgagaaaacc atcagcaagg ccaagggcca gccccgcgaa   1080

ccccaggtgt acacactgcc tccaagccag gaagagatga ccaagaatca ggtgtccctg   1140

acctgtctcg tgaaaggctt ctacccctcc gatatcgccg tggaatggga gagcaacggc   1200

cagcccgaga acaactacaa gaccaccccc cctgtgctgg actccgatgg ctcattcttc   1260

ctgtacagca gactgaccgt ggacaagagc cggtggcagg aaggcaacgt gttcagctgc   1320

tccgtgatgc acgaggccct gcacaaccac tacacccaga agtccctgtc tctgagcctg   1380

ggcaaa                                                              1386


<210> SEQ ID NO 70
<211> LENGTH: 699
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(699)
<223> OTHER INFORMATION: Nucleotid sequence encoding huAT01_L1
```

<400> SEQUENCE: 70
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacatgca aggccagcca ggacatcaac aagtatatcg cctggtatca gcagaagccc 180
ggcaaggccc ccaagctgct gatccactac accagcacac tgcagcctgg cgtgcccagc 240
agattttccg gctctggcag cggcagagac ttcaccctga ccatcagcag cctgcagccc 300
gaggacttcg ccacctacta ctgcctgcag tacgactacc tgctgacctt cggccagggc 360
accaaggtgg aaatcaagcg tacggtggcc gccccctccg tgttcatctt ccccccctcc 420
gacgagcagc tgaagtccgg caccgcctcc gtggtgtgcc tgctgaataa cttctacccc 480
agagaggcca aggtgcagtg gaaggtggac aacgccctgc agtccgggaa ctcccaggag 540
agcgtgaccg agcaggacag caaggacagc acctacagcc tgagcagcac cctgaccctg 600
agcaaagccg actacgagaa gcacaaggtg tacgcctgcg aggtgaccca ccagggcctg 660
agctcccccg tcaccaagag cttcaacagg ggggagtgt 699

<210> SEQ ID NO 71
<211> LENGTH: 699
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(699)
<223> OTHER INFORMATION: Nucleotid sequence encoding huAT01_L2

<400> SEQUENCE: 71
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacatgca aggccagcca ggacatcaac aagtatatcg cctggtatca gcagaagccc 180
ggcaaggccc ccaagctgct gatccactac accagcacac tgcagcccgg catccccagc 240
agattttccg gctctggcag cggcagagac tacaccctga ccatcagcag cctgcagcca 300
gaggacttcg ccacctacta ctgcctgcag tacgactacc tgctgacctt cggccagggc 360
accaaggtgg aaatcaagcg tacggtggcc gccccctccg tgttcatctt ccccccctcc 420
gacgagcagc tgaagtccgg caccgcctcc gtggtgtgcc tgctgaataa cttctacccc 480
agagaggcca aggtgcagtg gaaggtggac aacgccctgc agtccgggaa ctcccaggag 540
agcgtgaccg agcaggacag caaggacagc acctacagcc tgagcagcac cctgaccctg 600
agcaaagccg actacgagaa gcacaaggtg tacgcctgcg aggtgaccca ccagggcctg 660
agctcccccg tcaccaagag cttcaacagg ggggagtgt 699

<210> SEQ ID NO 72
<211> LENGTH: 1413
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1413)
<223> OTHER INFORMATION: Nucleotid sequence encoding huNB7_H3_IgG1LALA

<400> SEQUENCE: 72
atgaaacacc tgtggttctt cctcctgctg gtggcagctc ccagatgggt gctgagcgac 60
gtgcagctgc aggaatctgg ccctggcctc gtgaagccca gcgataccct gagcctgacc 120
tgtaccgtga ccggctacag catcaccagc gactacgcct ggaactggat cagacagccc 180
cctggcaaca agctggaatg gatcggccac atcagctacc ggggcaacac caactacaac 240
cccagcctga agtccagagt gaccatcagc cgggacacca gcaagaacca gttctccctg 300
aagctgagca gcgtgacagc cgccgatacc gccgtgtact actgcgccag ctggaactac 360
tacggctacg tggactatgc catggactac tggggccagg gcaccacagt gaccgtcagc 420
tcagcctcca ccaagggccc aagcgtcttc cccctggcac cctcctccaa gagcacctct 480
ggcggcacag ccgccctggg ctgcctggtc aaggactact tccccgaacc cgtgaccgtg 540
agctggaact caggcgccct gaccagcggc gtgcacacct tccccgctgt cctgcagtcc 600
tcaggactct actccctcag cagcgtggtg accgtgccct ccagcagctt gggcacccag 660
acctacatct gcaacgtgaa tcacaagccc agcaacacca aggtggacaa gagagttgag 720
cccaaatctt gtgacaaaac tcacacatgc ccaccctgcc cagcacctga agccgcgggg 780
ggaccctcag tcttcctctt ccccccaaaa cccaaggaca ccctcatgat ctcccggacc 840
cctgaggtca catgcgtggt ggtggacgtg agccacgaag accctgaggt caagttcaac 900
tggtacgtgg acggcgtgga ggtgcataat gccaagacaa agccccggga ggagcagtac 960
aacagcacgt accgggtggt cagcgtcctc accgtcctgc accaggactg gctgaatggc 1020
aaggagtaca agtgcaaggt ctccaacaaa gccctcccag cccccatcga gaaaaccatc 1080
tccaaagcca aaggccagcc ccgggaacca caggtgtaca ccctgccccc atcccgggag 1140
gagatgacca agaaccaggt cagcctgacc tgcctggtca aaggcttcta tcccagcgac 1200
atcgccgtgg agtgggagag caatggccag cccgagaaca actacaagac cacccctccc 1260
gtgctggact ccgacggctc cttcttcctc tacagcaagc tcaccgtgga caagagcagg 1320
tggcagcagg gcaacgtctt ctcatgctcc gtgatgcatg aggctctgca caaccactac 1380
acccagaaga gcctctccct gtctcccggc aaa 1413

<210> SEQ ID NO 73
<211> LENGTH: 1404
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1404)
<223> OTHER INFORMATION: Nucleotid sequence encoding huNB7_H3_IgG4Pro

<400> SEQUENCE: 73
atgaaacacc tgtggttctt cctcctgctg gtggcagctc ccagatgggt gctgagcgac 60
gtgcagctgc aggaatctgg ccctggcctc gtgaagccca gcgataccct gagcctgacc 120
tgtaccgtga ccggctacag catcaccagc gactacgcct ggaactggat cagacagccc 180
cctggcaaca agctggaatg gatcggccac atcagctacc ggggcaacac caactacaac 240
cccagcctga agtccagagt gaccatcagc cgggacacca gcaagaacca gttctccctg 300
aagctgagca gcgtgacagc cgccgatacc gccgtgtact actgcgccag ctggaactac 360
tacggctacg tggactatgc catggactac tggggccagg gcaccacagt gaccgtcagc 420
tcagcctcca ccaagggccc tagcgtgttc cctctggccc cttgtagcag aagcaccagc 480
gagtctacag ccgccctggg ctgcctcgtg aaggactact ttcccgagcc cgtgaccgtg 540
tcctggaact ctggcgctct gacaagcggc gtgcacacct ttccagccgt gctgcagagc 600
agcggcctgt actctctgtc cagcgtcgtg actgtgccca gcagctctct gggcaccaag 660
acctacacct gtaacgtgga ccacaagccc agcaacacca aggtggacaa gcgggtggaa 720
tctaagtacg gccctccctg ccctccttgc ccagcccctg aatttctggg cggaccctcc 780
gtgttcctgt tcccccccaaa gcccaaggac accctgatga tcagccggac ccccgaagtg 840
acctgcgtgg tggtggatgt gtcccaggaa gatcccgagg tgcagttcaa ttggtacgtg 900
gacggcgtgg aagtgcacaa cgccaagacc aagcctagag aggaacagtt caacagcacc 960
taccgggtgg tgtccgtgct gacagtgctg caccaggact ggctgaacgg caaagagtac 1020
aagtgcaagg tgtccaacaa gggcctgccc agctccatcg agaaaaccat cagcaaggcc 1080
aagggccagc cccgcgaacc ccaggtgtac acactgcctc caagccagga agagatgacc 1140
aagaatcagg tgtccctgac ctgtctcgtg aaaggcttct acccctccga tatcgccgtg 1200
gaatgggaga gcaacggcca gcccgagaac aactacaaga ccaccccccc tgtgctggac 1260
tccgatggct cattcttcct gtacagcaga ctgaccgtgg acaagagccg gtggcaggaa 1320
ggcaacgtgt tcagctgctc cgtgatgcac gaggccctgc acaaccacta cacccagaag 1380
tccctgtctc tgagcctggg caaa 1404

<210> SEQ ID NO 74
<211> LENGTH: 699
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(699)
<223> OTHER INFORMATION: Nucleotid sequence encoding huNB7_L3

<400> SEQUENCE: 74
atggtgctgc agacccaggt gttcatctcc ctgctgctgt ggatctccgg cgcgtacggc 60
gacatccaga tgacccagag ccctagcagc ctgagcgcca gcgtgggcga cagagtgacc 120
atcacctgta gagccagcca ggacatcagc aactacctga actggtatca gcagaaaccc 180
ggcaaggccg tgaagctgct gatctactac accagcagac tgcacagcgg cgtgcccagc 240
agattttctg gcagcggctc cggcaccgac tacaccctga caatcagcag cctgcagccc 300
gaggacttcg ctacctactt ctgtcagcaa ggcgacacct tccccacctt cggccagggc 360
accaaggtgg aaatcaagcg tacggtggcc gccccctccg tgttcatctt cccccccctcc 420 gacgagcagc tgaagtccgg caccgcctcc gtggtgtgcc tgctgaataa cttctacccc 480
agagaggcca aggtgcagtg gaaggtggac aacgccctgc agtccgggaa ctcccaggag 540
agcgtgaccg agcaggacag caaggacagc acctacagcc tgagcagcac cctgaccctg 600
agcaaagccg actacgagaa gcacaaggtg tacgcctgcg aggtgaccca ccagggcctg 660
agctcccccg tcaccaagag cttcaacagg ggggagtgt 699

<210> SEQ ID NO 75
<211> LENGTH: 1137
<212> TYPE: DNA
<213> ORGANISM: Homo sapiens

<400> SEQUENCE: 75

```
ccagcctccg gactctagag ccaccatgaa acacctgtgg ttcttcctcc tgctggtggc     60
agctcccaga tgggtgctga gccaggtgca attgtgcagg cggttagctc agcctccacc    120
aagggcccaa gcgtcttccc cctggcaccc tcctccaaga gcacctctgg cggcacagcc    180
gccctgggct gcctggtcaa ggactacttc cccgaacccg tgaccgtgag ctggaactca    240
ggcgccctga ccagcggcgt gcacaccttc cccgctgtcc tgcagtcctc aggactctac    300
tccctcagca gcgtggtgac cgtgccctcc agcagcttgg gcacccagac ctacatctgc    360
aacgtgaatc acaagcccag caacaccaag gtggacaaga gagttgagcc caaatcttgt    420
gacaaaactc acacatgccc accctgccca gcacctgaag ccgcgggggg accctcagtc    480
ttcctcttcc ccccaaaacc caaggacacc ctcatgatct cccggacccc tgaggtcaca    540
tgcgtggtgg tggacgtgag ccacgaagac cctgaggtca agttcaactg gtacgtggac    600
ggcgtggagg tgcataatgc caagacaaag ccccgggagg agcagtacaa cagcacgtac    660
cgggtggtca gcgtcctcac cgtcctgcac caggactggc tgaatggcaa ggagtacaag    720
tgcaaggtct ccaacaaagc cctcccagcc cccatcgaga aaaccatctc caaagccaaa    780
ggccagcccc gggaaccaca ggtgtacacc ctgcccccat cccgggagga gatgaccaag    840
aaccaggtca gcctgacctg cctggtcaaa ggcttctatc ccagcgacat cgccgtggag    900
tgggagagca atggccagcc cgagaacaac tacaagacca cccctcccgt gctggactcc    960
gacggctcct tcttcctcta cagcaagctc accgtggaca agagcaggtg gcagcagggc   1020
aacgtcttct catgctccgt gatgcatgag gctctgcaca accactacac ccagaagagc   1080
ctctccctgt ctcccggcaa atgagatatc gggcccgttt aaacggggga ggctaac      1137
```

<210> SEQ ID NO 76
<211> LENGTH: 1117
<212> TYPE: DNA
<213> ORGANISM: Homo sapiens

<400> SEQUENCE: 76

```
ccagcctccg gactctagag ccaccatgaa acacctgtgg ttcttcctcc tgctggtggc     60
agctcccaga tgggtgctga gccaggtgca attgtgcagg cggttagctc agcctccacc    120
aagggcccta gcgtgttccc tctggcccct tgtagcagaa gcaccagcga gtctacagcc    180
gccctgggct gcctcgtgaa ggactacttt cccgagcccg tgaccgtgtc ctggaactct    240
ggcgctctga caagcggcgt gcacaccttt ccagccgtgc tgcagagcag cggcctgtac    300
tctctgtcca gcgtcgtgac tgtgcccagc agctctctgg gcaccaagac ctacacctgt    360
aacgtggacc acaagcccag caacaccaag gtggacaagc gggtggaatc taagtacggc    420
cctccctgcc ctccttgccc agcccctgaa tttctgggcg gaccctccgt gttcctgttc    480
cccccaaagc ccaaggacac cctgatgatc agccggaccc ccgaagtgac ctgcgtggtg    540
gtggatgtgt cccaggaaga tcccgaggtg cagttcaatt ggtacgtgga cggcgtggaa    600
gtgcacaacg ccaagaccaa gcctagagag gaacagttca acagcaccta ccgggtggtg    660
tccgtgctga cagtgctgca ccaggactgg ctgaacggca aagagtacaa gtgcaaggtg    720
tccaacaagg gcctgcccag ctccatcgag aaaaccatca gcaaggccaa gggccagccc    780
cgcgaacccc aggtgtacac actgcctcca agccaggaag agatgaccaa gaatcaggtg    840
tccctgacct gtctcgtgaa aggcttctac ccctccgata tcgccgtgga atgggagagc    900
aacggccagc ccgagaacaa ctacaagacc acccccccctg tgctggactc cgatggctca    960
```

```
ttcttcctgt acagcagact gaccgtggac aagagccggt ggcaggaagg caacgtgttc   1020

agctgctccg tgatgcacga ggccctgcac aaccactaca cccagaagtc cctgtctctg   1080

agcctgggca aatgagttta aacgggggag gctaact                            1117


<210> SEQ ID NO 77
<211> LENGTH: 348
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(348)
<223> OTHER INFORMATION: Nucleotid sequence encoding heavy chain
      variable region of huAT01_H1

<400> SEQUENCE: 77

caggtgcagc tggtgcagtc tggcgccgaa gtgaagaaac caggcgccag cgtgaaggtg     60

tcctgcaagg ccagcggcta cacctttacc aacaactggc tgcactgggt gcgccaggct    120

ccaggacagg gactggaatg gatgggcgac atctacccca gcaacggccg gaccaactac    180

gcccagaaat tccagggcag agtgaccatc accgccgaca agagcaccag caccgcctac    240

atggaactga gcagcctgcg gagcgaggac accgccgtgt actactgcgc cagagagcgg    300

ggctacttcg actattgggg ccagggcaca ctcgtgaccg tcagctca                 348


<210> SEQ ID NO 78
<211> LENGTH: 348
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(348)
<223> OTHER INFORMATION: Nucleotid sequence encoding heavy chain
      variable region of huAT01_H3

<400> SEQUENCE: 78

caggtgcagc tggtgcagtc tggcgccgaa gtgaagaaac caggcgccag cgtgaaggtg     60

tcctgcaagg ccagcggcta cacctttacc aacaactggc tgcactgggt gcgccaggct    120

ccaggacagg gactggaatg gatgggcgac atctacccca gcaacggccg gaccaactac    180

gcccagaaat tccagggcag agtgaccctg accgtggaca agagcaccag caccgcctac    240

atggaactga gcagcctgcg gagcgaggat accgccgtgt acttctgtgc cagagagcgg    300

ggctacttcg actactgggg ccagggaaca ctcgtgaccg tcagctca                 348


<210> SEQ ID NO 79
<211> LENGTH: 318
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(318)
<223> OTHER INFORMATION: Nucleotid sequence encoding light chain
      variable region of huAT01_L1

<400> SEQUENCE: 79

gacatccaga tgacccagag ccctagcagc ctgagcgcca gcgtgggcga cagagtgacc     60

atcacatgca aggccagcca ggacatcaac aagtatatcg cctggtatca gcagaagccc    120
```

-continued

```
ggcaaggccc ccaagctgct gatccactac accagcacac tgcagcctgg cgtgcccagc    180

agattttccg gctctggcag cggcagagac ttcaccctga ccatcagcag cctgcagccc    240

gaggacttcg ccacctacta ctgcctgcag tacgactacc tgctgacctt cggccagggc    300

accaaggtgg aaatcaag                                                  318
```

<210> SEQ ID NO 80
<211> LENGTH: 318
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(318)
<223> OTHER INFORMATION: Nucleotid sequence encoding light chain variable region of huAT01_L2

<400> SEQUENCE: 80

```
gacatccaga tgacccagag ccctagcagc ctgagcgcca gcgtgggcga cagagtgacc     60

atcacatgca aggccagcca ggacatcaac aagtatatcg cctggtatca gcagaagccc    120

ggcaaggccc ccaagctgct gatccactac accagcacac tgcagcccgg catccccagc    180

agattttccg gctctggcag cggcagagac tacaccctga ccatcagcag cctgcagcca    240

gaggacttcg ccacctacta ctgcctgcag tacgactacc tgctgacctt cggccagggc    300

accaaggtgg aaatcaag                                                  318
```

<210> SEQ ID NO 81
<211> LENGTH: 366
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(366)
<223> OTHER INFORMATION: Nucleotid sequence encoding heavy chain variable region of huNB7_H3

<400> SEQUENCE: 81

```
gacgtgcagc tgcaggaatc tggccctggc ctcgtgaagc ccagcgatac cctgagcctg     60

acctgtaccg tgaccggcta cagcatcacc agcgactacg cctggaactg gatcagacag    120

ccccctggca acaagctgga atggatcggc cacatcagct accggggcaa caccaactac    180

aaccccagcc tgaagtccag agtgaccatc agccgggaca ccagcaagaa ccagttctcc    240

ctgaagctga gcagcgtgac agccgccgat accgccgtgt actactgcgc cagctggaac    300

tactacggct acgtggacta tgccatggac tactggggcc agggcaccac agtgaccgtc    360

agctca                                                               366
```

<210> SEQ ID NO 82
<211> LENGTH: 318
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(318)
<223> OTHER INFORMATION: Nucleotid sequence encoding light chain variable region of huNB7_L3

-continued

<400> SEQUENCE: 82

```
gacatccaga tgacccagag ccctagcagc ctgagcgcca gcgtgggcga cagagtgacc     60

atcacctgta gagccagcca ggacatcagc aactacctga actggtatca gcagaaaccc    120

ggcaaggccg tgaagctgct gatctactac accagcagac tgcacagcgg cgtgcccagc    180

agattttctg gcagcggctc cggcaccgac tacaccctga caatcagcag cctgcagccc    240

gaggacttcg ctacctactt ctgtcagcaa ggcgacacct tccccacctt cggccagggc    300

accaaggtgg aaatcaag                                                  318
```

<210> SEQ ID NO 83
<211> LENGTH: 1050
<212> TYPE: PRT
<213> ORGANISM: Mus musculus

<400> SEQUENCE: 83

```
Met Val Phe Ser Met Trp Thr Arg Lys Arg Gln Ile Leu Ile Phe Leu
1               5                   10                  15

Asn Met Leu Leu Val Ser Arg Val Phe Gly Phe Arg Trp Phe Pro Lys
            20                  25                  30

Thr Leu Pro Cys Glu Val Lys Val Asn Ile Pro Glu Ala His Val Ile
        35                  40                  45

Val Asp Cys Thr Asp Lys His Leu Thr Glu Ile Pro Glu Gly Ile Pro
    50                  55                  60

Thr Asn Thr Thr Asn Leu Thr Leu Thr Ile Asn His Ile Pro Ser Ile
65                  70                  75                  80

Ser Pro Asp Ser Phe Arg Arg Leu Asn His Leu Glu Glu Ile Asp Leu
                85                  90                  95

Arg Cys Asn Cys Val Pro Val Leu Leu Gly Ser Lys Ala Asn Val Cys
            100                 105                 110

Thr Lys Arg Leu Gln Ile Arg Pro Gly Ser Phe Ser Gly Leu Ser Asp
        115                 120                 125

Leu Lys Ala Leu Tyr Leu Asp Gly Asn Gln Leu Leu Glu Ile Pro Gln
    130                 135                 140

Asp Leu Pro Ser Ser Leu His Leu Leu Ser Leu Glu Ala Asn Asn Ile
145                 150                 155                 160

Phe Ser Ile Thr Lys Glu Asn Leu Thr Glu Leu Val Asn Ile Glu Thr
                165                 170                 175

Leu Tyr Leu Gly Gln Asn Cys Tyr Tyr Arg Asn Pro Cys Asn Val Ser
            180                 185                 190

Tyr Ser Ile Glu Lys Asp Ala Phe Leu Val Met Arg Asn Leu Lys Val
        195                 200                 205

Leu Ser Leu Lys Asp Asn Asn Val Thr Ala Val Pro Thr Thr Leu Pro
    210                 215                 220

Pro Asn Leu Leu Glu Leu Tyr Leu Tyr Asn Asn Ile Ile Lys Lys Ile
225                 230                 235                 240

Gln Glu Asn Asp Phe Asn Asn Leu Asn Glu Leu Gln Val Leu Asp Leu
                245                 250                 255

Ser Gly Asn Cys Pro Arg Cys Tyr Asn Val Pro Tyr Pro Cys Thr Pro
            260                 265                 270

Cys Glu Asn Asn Ser Pro Leu Gln Ile His Asp Asn Ala Phe Asn Ser
        275                 280                 285

Leu Thr Glu Leu Lys Val Leu Arg Leu His Ser Asn Ser Leu Gln His
    290                 295                 300
```

-continued

```
Val Pro Pro Thr Trp Phe Lys Asn Met Arg Asn Leu Gln Glu Leu Asp
305                 310                 315                 320

Leu Ser Gln Asn Tyr Leu Ala Arg Glu Ile Glu Glu Ala Lys Phe Leu
                325                 330                 335

His Phe Leu Pro Asn Leu Val Glu Leu Asp Phe Ser Phe Asn Tyr Glu
            340                 345                 350

Leu Gln Val Tyr His Ala Ser Ile Thr Leu Pro His Ser Leu Ser Ser
        355                 360                 365

Leu Glu Asn Leu Lys Ile Leu Arg Val Lys Gly Tyr Val Phe Lys Glu
    370                 375                 380

Leu Lys Asn Ser Ser Leu Ser Val Leu His Lys Leu Pro Arg Leu Glu
385                 390                 395                 400

Val Leu Asp Leu Gly Thr Asn Phe Ile Lys Ile Ala Asp Leu Asn Ile
                405                 410                 415

Phe Lys His Phe Glu Asn Leu Lys Leu Ile Asp Leu Ser Val Asn Lys
            420                 425                 430

Ile Ser Pro Ser Glu Glu Ser Arg Glu Val Gly Phe Cys Pro Asn Ala
        435                 440                 445

Gln Thr Ser Val Asp Arg His Gly Pro Gln Val Leu Glu Ala Leu His
    450                 455                 460

Tyr Phe Arg Tyr Asp Glu Tyr Ala Arg Ser Cys Arg Phe Lys Asn Lys
465                 470                 475                 480

Glu Pro Pro Ser Phe Leu Pro Leu Asn Ala Asp Cys His Ile Tyr Gly
                485                 490                 495

Gln Thr Leu Asp Leu Ser Arg Asn Asn Ile Phe Phe Ile Lys Pro Ser
            500                 505                 510

Asp Phe Gln His Leu Ser Phe Leu Lys Cys Leu Asn Leu Ser Gly Asn
        515                 520                 525

Thr Ile Gly Gln Thr Leu Asn Gly Ser Glu Leu Trp Pro Leu Arg Glu
    530                 535                 540

Leu Arg Tyr Leu Asp Phe Ser Asn Asn Arg Leu Asp Leu Leu Tyr Ser
545                 550                 555                 560

Thr Ala Phe Glu Glu Leu Gln Ser Leu Glu Val Leu Asp Leu Ser Ser
                565                 570                 575

Asn Ser His Tyr Phe Gln Ala Glu Gly Ile Thr His Met Leu Asn Phe
            580                 585                 590

Thr Lys Lys Leu Arg Leu Leu Asp Lys Leu Met Met Asn Asp Asn Asp
        595                 600                 605

Ile Ser Thr Ser Ala Ser Arg Thr Met Glu Ser Asp Ser Leu Arg Ile
    610                 615                 620

Leu Glu Phe Arg Gly Asn His Leu Asp Val Leu Trp Arg Ala Gly Asp
625                 630                 635                 640

Asn Arg Tyr Leu Asp Phe Phe Lys Asn Leu Phe Asn Leu Glu Val Leu
                645                 650                 655

Asp Ile Ser Arg Asn Ser Leu Asn Ser Leu Pro Pro Glu Val Phe Glu
            660                 665                 670

Gly Met Pro Pro Asn Leu Lys Asn Leu Ser Leu Ala Lys Asn Gly Leu
        675                 680                 685

Lys Ser Phe Phe Trp Asp Arg Leu Gln Leu Leu Lys His Leu Glu Ile
    690                 695                 700

Leu Asp Leu Ser His Asn Gln Leu Thr Lys Val Pro Glu Arg Leu Ala
705                 710                 715                 720
```

-continued

```
Asn Cys Ser Lys Ser Leu Thr Thr Leu Ile Leu Lys His Asn Gln Ile
                725                 730                 735

Arg Gln Leu Thr Lys Tyr Phe Leu Glu Asp Ala Leu Gln Leu Arg Tyr
            740                 745                 750

Leu Asp Ile Ser Ser Asn Lys Ile Gln Val Ile Gln Lys Thr Ser Phe
        755                 760                 765

Pro Glu Asn Val Leu Asn Asn Leu Glu Met Leu Val Leu His His Asn
    770                 775                 780

Arg Phe Leu Cys Asn Cys Asp Ala Val Trp Phe Val Trp Trp Val Asn
785                 790                 795                 800

His Thr Asp Val Thr Ile Pro Tyr Leu Ala Thr Asp Val Thr Cys Val
                805                 810                 815

Gly Pro Gly Ala His Lys Gly Gln Ser Val Ile Ser Leu Asp Leu Tyr
            820                 825                 830

Thr Cys Glu Leu Asp Leu Thr Asn Leu Ile Leu Phe Ser Val Ser Ile
        835                 840                 845

Ser Ser Val Leu Phe Leu Met Val Val Met Thr Thr Ser His Leu Phe
    850                 855                 860

Phe Trp Asp Met Trp Tyr Ile Tyr Tyr Phe Trp Lys Ala Lys Ile Lys
865                 870                 875                 880

Gly Tyr Gln His Leu Gln Ser Met Glu Ser Cys Tyr Asp Ala Phe Ile
                885                 890                 895

Val Tyr Asp Thr Lys Asn Ser Ala Val Thr Glu Trp Val Leu Gln Glu
            900                 905                 910

Leu Val Ala Lys Leu Glu Asp Pro Arg Glu Lys His Phe Asn Leu Cys
        915                 920                 925

Leu Glu Glu Arg Asp Trp Leu Pro Gly Gln Pro Val Leu Glu Asn Leu
    930                 935                 940

Ser Gln Ser Ile Gln Leu Ser Lys Lys Thr Val Phe Val Met Thr Gln
945                 950                 955                 960

Lys Tyr Ala Lys Thr Glu Ser Phe Lys Met Ala Phe Tyr Leu Ser His
                965                 970                 975

Gln Arg Leu Leu Asp Glu Lys Val Asp Val Ile Ile Leu Ile Phe Leu
            980                 985                 990

Glu Lys Pro Leu Gln Lys Ser Lys  Phe Leu Gln Leu Arg  Lys Arg Leu
        995                 1000                1005

Cys Arg  Ser Ser Val Leu Glu  Trp Pro Ala Asn Pro  Gln Ala His
    1010                1015                1020

Pro Tyr  Phe Trp Gln Cys Leu  Lys Asn Ala Leu Thr  Thr Asp Asn
    1025                1030                1035

His Val  Ala Tyr Ser Gln Met  Phe Lys Glu Thr Val
    1040                1045                1050
```

<210> SEQ ID NO 84
<211> LENGTH: 1050
<212> TYPE: PRT
<213> ORGANISM: Rattus norvegicus

<400> SEQUENCE: 84

```
Met Val Phe Pro Met Trp Thr Leu Lys Arg Gln Ser Phe Ile Phe Leu
1               5                   10                  15

Asn Met Ile Leu Val Ser Arg Val Leu Gly Phe Arg Trp Tyr Pro Lys
            20                  25                  30

Thr Leu Pro Cys Asp Val Ser Leu Asp Ser Thr Asn Thr His Val Ile
        35                  40                  45
```

-continued

```
Val Asp Cys Thr Asp Lys His Leu Thr Glu Ile Pro Glu Gly Ile Pro
    50                  55                  60

Thr Asn Thr Thr Asn Leu Thr Leu Thr Ile Asn His Ile Pro Ser Ile
65                  70                  75                  80

Ser Pro Asp Ser Phe His Arg Leu Lys His Leu Glu Glu Leu Asp Leu
                85                  90                  95

Arg Cys Asn Cys Val Pro Ile Leu Leu Gly Ser Lys Ala Asn Val Cys
            100                 105                 110

Thr Lys Arg Leu Gln Ile Arg Pro Gly Ser Phe Ser Gly Leu Ser Asp
        115                 120                 125

Leu Lys Ser Leu Tyr Leu Asp Gly Asn Gln Leu Leu Glu Ile Pro Gln
    130                 135                 140

Asp Leu Pro Ser Ser Leu Gln Leu Leu Ser Leu Glu Ala Asn Asn Ile
145                 150                 155                 160

Phe Ser Ile Thr Lys Glu Asn Leu Ser Glu Leu Val Asn Ile Glu Ser
                165                 170                 175

Leu Tyr Leu Gly Gln Asn Cys Tyr Tyr Arg Asn Pro Cys Asn Val Ser
            180                 185                 190

Tyr Ser Ile Glu Lys Asp Ala Phe Leu Val Met Lys Asn Leu Lys Val
        195                 200                 205

Leu Ser Leu Lys Asp Asn Asn Val Thr Ala Val Pro Thr Ile Leu Pro
    210                 215                 220

Pro Asn Leu Leu Glu Leu Tyr Leu Tyr Asn Asn Ile Ile Lys Arg Ile
225                 230                 235                 240

Gln Glu His Asp Phe Asn Lys Leu Ser Gln Leu Gln Val Leu Asp Leu
                245                 250                 255

Ser Gly Asn Cys Pro Arg Cys Tyr Asn Val Pro Tyr Pro Cys Thr Pro
            260                 265                 270

Cys Glu Asn Asn Ser Pro Leu Gln Ile His Asp Asn Ala Phe Asp Ser
        275                 280                 285

Leu Thr Glu Leu Lys Val Leu Arg Leu His Ser Asn Ser Leu Gln His
    290                 295                 300

Val Pro Ala Glu Trp Phe Lys Asn Met Ser Asn Leu Gln Glu Leu Asp
305                 310                 315                 320

Leu Ser Gln Asn Tyr Leu Ala Arg Glu Ile Glu Glu Ala Lys Phe Leu
                325                 330                 335

Asn Ser Leu Pro Asn Leu Val Gln Leu Asp Leu Ser Phe Asn Tyr Glu
            340                 345                 350

Leu Gln Val Tyr His Ala Ser Ile Thr Leu Pro His Ser Leu Ser Ser
        355                 360                 365

Leu Thr Lys Leu Lys Asn Leu Tyr Ile Lys Gly Tyr Val Phe Lys Glu
    370                 375                 380

Leu Lys Asp Ser Ser Leu Ser Val Leu His Asn Leu Ser Asn Leu Glu
385                 390                 395                 400

Val Leu Asp Leu Gly Thr Asn Phe Ile Lys Ile Ala Asp Leu Asn Ile
                405                 410                 415

Phe Gln Gln Phe Glu Asn Leu Lys Phe Ile Asp Leu Ser Val Asn Lys
            420                 425                 430

Ile Ser Pro Ser Glu Glu Ser Arg Glu Val Gly Leu Cys Pro Asn Ala
        435                 440                 445

Gln Thr Ser Val Asp Trp His Gly Pro Gln Val Leu Glu Ala Leu His
    450                 455                 460
```

-continued

```
Tyr Phe Arg Tyr Asp Glu Tyr Ala Arg Ser Cys Arg Phe Lys Asn Lys
465                 470                 475                 480

Glu Pro Pro Thr Phe Leu Pro Leu Asn Ala Asp Cys His Thr Tyr Gly
                485                 490                 495

Lys Thr Leu Asp Leu Ser Arg Asn Asn Ile Phe Phe Ile Lys Pro Ser
            500                 505                 510

Asp Phe Lys His Leu Ser Phe Leu Lys Cys Leu Asn Leu Ser Gly Asn
        515                 520                 525

Ala Ile Gly Gln Thr Leu Asn Gly Ser Glu Leu Gln Pro Leu Arg Glu
    530                 535                 540

Leu Arg Tyr Leu Asp Phe Ser Asn Asn Arg Leu Asp Leu Leu Tyr Ser
545                 550                 555                 560

Thr Ala Phe Glu Glu Leu Gln Asn Leu Glu Ile Leu Asp Leu Ser Ser
                565                 570                 575

Asn Ser His Tyr Phe Gln Ala Glu Gly Ile Thr His Met Leu Asn Phe
            580                 585                 590

Thr Lys Lys Leu Arg His Leu Glu Lys Leu Met Met Asn Asp Asn Asp
        595                 600                 605

Ile Ser Thr Ser Ala Ser Arg Thr Met Glu Ser Glu Ser Leu Arg Val
    610                 615                 620

Leu Glu Phe Arg Gly Asn His Leu Asp Val Leu Trp Arg Asp Gly Asp
625                 630                 635                 640

Asn Arg Tyr Leu Asp Phe Phe Lys Asn Leu Leu Asn Leu Glu Glu Leu
                645                 650                 655

Asp Ile Ser Arg Asn Ser Leu Asn Ser Val Pro Pro Gly Val Phe Glu
            660                 665                 670

Gly Met Pro Pro Asn Leu Thr Thr Leu Ser Leu Ala Lys Asn Gly Leu
        675                 680                 685

Arg Ser Phe Ser Trp Gly Arg Leu Gln Leu Leu Lys His Leu Lys Asn
    690                 695                 700

Leu Asp Leu Ser His Asn Gln Leu Thr Thr Val Pro Ala Arg Leu Ala
705                 710                 715                 720

Asn Cys Ser Lys Ser Leu Thr Lys Leu Ile Leu Asn His Asn Gln Ile
                725                 730                 735

Arg Gln Leu Thr Lys Tyr Phe Leu Glu Asp Ala Leu Gln Leu Arg Tyr
            740                 745                 750

Leu Asp Ile Ser Ser Asn Lys Ile Gln Val Ile Gln Lys Thr Ser Phe
        755                 760                 765

Pro Glu Asn Val Leu Asn Asn Leu Asn Met Leu Leu Leu His His Asn
    770                 775                 780

Arg Phe Leu Cys Asn Cys Asp Ala Val Trp Phe Val Trp Trp Val Asn
785                 790                 795                 800

His Thr Asp Val Thr Ile Pro Tyr Leu Ala Thr Asp Val Thr Cys Ala
                805                 810                 815

Gly Pro Gly Ala His Lys Gly Gln Ser Val Ile Ser Leu Asp Leu Tyr
            820                 825                 830

Thr Cys Glu Leu Asp Leu Thr Asn Leu Ile Leu Phe Ser Val Ser Ile
        835                 840                 845

Ser Ser Val Leu Phe Leu Met Ile Val Met Thr Thr Ser His Leu Phe
    850                 855                 860

Phe Trp Asp Met Trp Tyr Ile Tyr Tyr Phe Trp Lys Ala Lys Ile Lys
865                 870                 875                 880
```

Gly Tyr Gln His Leu Gln Ser Met Glu Ser Cys Tyr Asp Ala Phe Ile
885 890 895

Val Tyr Asp Thr Lys Asn Ser Ala Val Thr Glu Trp Val Leu Gln Glu
900 905 910

Leu Val Val Lys Leu Glu Asp Pro Arg Glu Lys His Phe Asn Leu Cys
915 920 925

Leu Glu Glu Arg Asp Trp Leu Pro Gly Gln Pro Val Leu Glu Asn Leu
930 935 940

Ser Gln Ser Ile Gln Leu Ser Arg Lys Thr Val Phe Val Met Thr Gln
945 950 955 960

Lys Tyr Ala Lys Thr Glu Ser Phe Lys Met Ala Phe Tyr Leu Ser His
965 970 975

Gln Arg Leu Met Asp Glu Lys Val Asp Val Ile Ile Leu Ile Phe Leu
980 985 990

Glu Lys Pro Leu Gln Lys Ser Lys Phe Leu Gln Leu Arg Lys Arg Leu
995 1000 1005

Cys Ser Ser Ser Val Leu Glu Trp Pro Thr Asn Pro Gln Ala His
1010 1015 1020

Pro Tyr Phe Trp Gln Cys Leu Lys Asn Ala Leu Thr Thr Asp Asn
1025 1030 1035

His Val Ala Tyr Ser Gln Met Phe Lys Glu Thr Val
1040 1045 1050

<210> SEQ ID NO 85
<211> LENGTH: 1049
<212> TYPE: PRT
<213> ORGANISM: Macaca mulatta

<400> SEQUENCE: 85

Met Met Phe Pro Val Trp Thr Leu Lys Arg Gln Ile Leu Ile Leu Phe
1 5 10 15

Asn Ile Ile Leu Ile Ser Lys Leu Leu Gly Ala Arg Trp Phe Pro Lys
20 25 30

Thr Leu Pro Cys Asp Val Thr Leu Asp Val Ser Lys Asn His Val Ile
35 40 45

Val Asp Cys Thr Asp Lys His Leu Thr Glu Ile Pro Gly Gly Ile Pro
50 55 60

Thr Asn Thr Thr Asn Leu Thr Leu Thr Ile Asn His Ile Pro Asp Ile
65 70 75 80

Ser Pro Ala Ser Phe His Arg Leu Val His Leu Val Glu Ile Asp Phe
85 90 95

Arg Cys Asn Cys Val Pro Ile Arg Leu Gly Ser Lys Ser Asn Met Cys
100 105 110

Pro Arg Arg Leu Gln Ile Lys Pro Arg Ser Phe Ser Gly Leu Thr Tyr
115 120 125

Leu Lys Ser Leu Tyr Leu Asp Gly Asn Gln Leu Leu Glu Ile Pro Gln
130 135 140

Gly Leu Pro Pro Ser Leu Gln Leu Leu Ser Leu Glu Ala Asn Asn Ile
145 150 155 160

Phe Ser Ile Arg Lys Glu Asn Leu Thr Glu Leu Ala Asn Ile Glu Ile
165 170 175

Leu Tyr Leu Gly Gln Asn Cys Tyr Tyr Arg Asn Pro Cys Tyr Val Ser
180 185 190

Tyr Ser Ile Glu Lys Asp Ala Phe Leu Asn Leu Thr Lys Leu Lys Val
195 200 205

-continued

```
Leu Ser Leu Lys Asp Asn Asn Val Thr Thr Val Pro Thr Val Leu Pro
    210                 215                 220

Ser Thr Leu Thr Glu Leu Tyr Leu Tyr Asn Asn Met Ile Ala Glu Ile
225                 230                 235                 240

Gln Glu Asp Asp Phe Asn Asn Leu Asn Gln Leu Gln Ile Leu Asp Leu
                245                 250                 255

Ser Gly Asn Cys Pro Arg Cys Tyr Asn Ala Pro Phe Pro Cys Thr Pro
            260                 265                 270

Cys Lys Asn Asn Ser Pro Leu Gln Ile Pro Val Asn Ala Phe Asp Ala
        275                 280                 285

Leu Thr Glu Leu Lys Val Leu Arg Leu His Ser Asn Ser Leu Gln His
    290                 295                 300

Val Pro Pro Arg Trp Phe Lys Asn Ile Asn Asn Leu Gln Glu Leu Asp
305                 310                 315                 320

Leu Ser Gln Asn Phe Leu Ala Lys Glu Ile Gly Asp Ala Lys Phe Leu
                325                 330                 335

His Phe Leu Pro Asn Leu Ile Gln Leu Asp Leu Ser Phe Asn Phe Glu
            340                 345                 350

Leu Gln Val Tyr Arg Ala Ser Met Asn Leu Ser Gln Ala Phe Ser Ser
        355                 360                 365

Leu Lys Ser Leu Lys Ile Leu Arg Ile Arg Gly Tyr Val Phe Lys Glu
    370                 375                 380

Leu Lys Ser Phe Asn Leu Ser Pro Leu His Asn Leu Gln Asn Leu Glu
385                 390                 395                 400

Val Leu Asp Leu Gly Thr Asn Phe Ile Lys Ile Ala Asn Leu Ser Met
                405                 410                 415

Phe Lys Gln Phe Lys Arg Leu Lys Val Ile Asp Leu Ser Val Asn Lys
            420                 425                 430

Ile Ser Pro Ser Gly Asp Ser Ser Glu Val Gly Phe Cys Ser Asn Ala
        435                 440                 445

Arg Thr Ser Val Glu Ser Tyr Glu Pro Gln Val Leu Glu Gln Leu Tyr
    450                 455                 460

Tyr Phe Arg Tyr Asp Lys Tyr Ala Arg Ser Cys Arg Phe Lys Asn Lys
465                 470                 475                 480

Glu Ala Ser Phe Thr Ser Val Asn Glu Ser Cys Tyr Lys Tyr Gly Gln
                485                 490                 495

Thr Leu Asp Leu Ser Lys Asn Ser Ile Phe Phe Ile Lys Ser Ser Asp
            500                 505                 510

Phe Gln His Leu Ser Phe Leu Lys Cys Leu Asn Leu Ser Gly Asn Leu
        515                 520                 525

Ile Ser Gln Thr Leu Asn Gly Ser Glu Phe Gln Pro Leu Ala Glu Leu
    530                 535                 540

Arg Tyr Leu Asp Phe Ser Asn Asn Arg Leu Asp Leu Leu His Ser Thr
545                 550                 555                 560

Ala Phe Glu Glu Leu Arg Lys Leu Glu Val Leu Asp Ile Ser Ser Asn
                565                 570                 575

Ser His Tyr Phe Gln Ser Glu Gly Ile Thr His Met Leu Asn Phe Thr
            580                 585                 590

Lys Asn Leu Lys Val Leu Gln Lys Leu Met Met Asn Asp Asn Asp Ile
        595                 600                 605

Ser Ser Ser Thr Ser Arg Thr Met Glu Ser Glu Ser Leu Arg Thr Leu
    610                 615                 620
```

-continued

```
Glu Phe Arg Gly Asn His Leu Asp Val Leu Trp Arg Asp Gly Asp Asn
625                 630                 635                 640

Arg Tyr Leu Gln Leu Phe Lys Asn Leu Leu Lys Leu Glu Glu Leu Asp
                645                 650                 655

Ile Ser Lys Asn Ser Leu Ser Phe Leu Pro Ser Gly Val Phe Asp Gly
            660                 665                 670

Met Pro Pro Asn Leu Lys Asn Leu Ser Leu Ala Lys Asn Gly Leu Lys
        675                 680                 685

Ser Phe Ile Trp Glu Lys Leu Arg Tyr Leu Lys Asn Leu Glu Thr Leu
    690                 695                 700

Asp Leu Ser His Asn Gln Leu Thr Thr Val Pro Glu Arg Leu Ser Asn
705                 710                 715                 720

Cys Ser Arg Ser Leu Lys Asn Leu Ile Leu Lys Asn Asn Gln Ile Arg
                725                 730                 735

Ser Leu Thr Lys Tyr Phe Leu Gln Asp Ala Phe Gln Leu Arg Tyr Leu
            740                 745                 750

Asp Leu Ser Ser Asn Lys Ile Gln Met Ile Gln Lys Thr Ser Phe Pro
        755                 760                 765

Glu Asn Val Leu Asn Asn Leu Lys Met Leu Leu Leu His His Asn Arg
    770                 775                 780

Phe Leu Cys Thr Cys Asp Ala Val Trp Phe Val Trp Trp Val Asn His
785                 790                 795                 800

Thr Glu Val Thr Ile Pro Tyr Leu Ala Thr Asp Val Thr Cys Val Gly
                805                 810                 815

Pro Gly Ala His Lys Gly Gln Ser Val Ile Ser Leu Asp Leu Tyr Thr
            820                 825                 830

Cys Glu Leu Asp Leu Thr Asn Leu Ile Leu Phe Ser Leu Ser Ile Ser
        835                 840                 845

Val Ser Leu Phe Leu Met Val Met Met Thr Ala Ser His Leu Tyr Phe
    850                 855                 860

Trp Asp Val Trp Tyr Ile Tyr His Phe Cys Lys Ala Lys Ile Lys Gly
865                 870                 875                 880

Tyr Gln Arg Leu Ile Ser Pro Asp Cys Cys Tyr Asp Ala Phe Ile Val
                885                 890                 895

Tyr Asp Thr Lys Asp Pro Ala Val Thr Glu Trp Val Leu Ala Glu Leu
            900                 905                 910

Val Ala Lys Leu Glu Asp Pro Arg Glu Lys His Phe Asn Leu Cys Leu
        915                 920                 925

Glu Glu Arg Asp Trp Leu Pro Gly Gln Pro Val Leu Glu Asn Leu Ser
    930                 935                 940

Gln Ser Ile Gln Leu Ser Lys Lys Thr Val Phe Val Met Thr Asp Lys
945                 950                 955                 960

Tyr Ala Lys Thr Glu Asn Phe Lys Ile Ala Phe Tyr Leu Ser His Gln
                965                 970                 975

Arg Leu Met Asp Glu Lys Val Asp Val Ile Ile Leu Ile Phe Leu Glu
            980                 985                 990

Lys Pro Phe Gln Lys Ser Lys Phe  Leu Gln Leu Arg Lys  Arg Leu Cys
        995                 1000                1005

Gly Ser  Ser Val Leu Glu Trp  Pro Thr Asn Pro Gln  Ala His Pro
    1010                1015                1020
```

```
Tyr Phe  Trp Gln Cys Leu Lys  Asn Ala Leu Ala Thr  Asp Asn His
    1025                 1030                 1035

Val Ala  Tyr Ser Gln Val Phe  Lys Glu Thr Val
    1040                 1045


<210> SEQ ID NO 86
<211> LENGTH: 1797
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1797)
<223> OTHER INFORMATION: Nucleotid sequence of human Unc93B1 D34A
      mutant-HAx2 gene

<400> SEQUENCE: 86

atggaggtgg agcctccgct ctaccctgtg gccggggccg cgggtcctca aggggatgaa     60

gaccggcacg gagttcctga tgggccagag gctcccttgg ccgaactcgt gggtgcgtac    120

cccaactaca atgaggagga ggaagagcgc cgctactacc gccgcaagcg cctcggagtg    180

gtcaagaacg tgctggcggc cagcacgggt gtcaccctta cttacggcgt ctacctgggc    240

ctcctgcaga tgcaactgat cctgcactat gatgagacct acagagaggt gaagtatggc    300

aacatggggc tgccggacat cgatagcaag atgctgatgg gtatcaacgt gacgcctatc    360

gctgccctgc tctacacacc tgtgctcatc aggtttttg gtaccaagtg gatgatgttc    420

ttggctgtgg gcatctatgc cctctttgtc tctaccaact actgggaacg ctactacacg    480

ctggtgccct ctgctgtggc tctgggcatg gccattgtgc ctctgtgggc ctccatgggc    540

aactatatca ccaggatgtc ccagaagtac tatgaatact cccactacaa ggagcaagat    600

gagcagggac ctcagcagcg cccaccacga ggttcccacg caccctatct cctggttttc    660

caggccatct tctatagctt cttccacttg agcttcgcgt gtgcccagct gcccatgatt    720

tacttcctca acaactacct gtatgacctg aaccacacac tgatcaacgt gcagagctgc    780

ggtactaaga gccaaggcat tctgaatggc ttcaacaaga cggtccttcg gacgctgccg    840

cgcagcaaaa accttattgt tgtagagagc gtgctcatgg cggtggcctt cttggccatg    900

ctgatggtgc tgggcctgtg tggagccgct taccggccca cggaagagat cgacctgcgc    960

agcgtgggct ggggcaacat cttccagctg cccttcaaac acgtgcgtga ctttcgctta   1020

cgccatctgg tgcccttctt tatctacagt ggctttgagg tgctctttgc ctgcactggt   1080

tttgccctgg gctacggcgt gtgctccatg ggctggagc gactggcata cctgctcata   1140

gcttacagcc tgggtgcctc agcctcctcg gttctggggc tgctgggact gtggctgcct   1200

cgctctgtcc cgctcgtggc tggggcagga ctgcacctac tgctcaccct tagcctcttt   1260

ttctgggctc ctgctcctcg ggtcctccag cacagttgga tcttttactt cgtggctgcc   1320

ctctggggtg tgggcagcgc cctcaacaag accggactta gcacactcct gggcatccta   1380

tatgaagaca aagagaggca ggacttcatc ttcaccatct atcactggtg gcaggccgtg   1440

gccatctttg ttgtgtacct gggctccagc ttgcccatga aggccaagct ggcagtgttg   1500

ctggtgaccc tggtagcagc agcagcctca tacctgtgga tggagcagaa gttgcagcaa   1560

ggattggtcc cgcggcagcc gcgcattccg aagccacagc acaaagtccg cggctaccgc   1620

tacctggagg aggacaactc ggatgagagt gacatggagg gcgagcaggg tcagggggac   1680
```

-continued

```
tgcgcagagg acgaagcacc acaggcaggg cccctgggtg cagagccagc tggcccctgc   1740

cgcaagccct gtccctatga acaggctctg ggtggcgatg ggcctgagga gcagtga      1797


<210> SEQ ID NO 87
<211> LENGTH: 23
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(23)
<223> OTHER INFORMATION: guide RNA targeting the sequence on exon 5 of
      the mouse TLR7 gene

<400> SEQUENCE: 87

gaacaguugg ccaaucucuc agg                                         23
```

ANTI-HUMAN TLR7 ANTIBODY

CROSS REFERENCE TO RELATED APPLICATIONS

The present application is a continuation of U.S. patent application Ser. No. 17/069,760, filed Oct. 13, 2020, which is a continuation-in-part application of International Application No. PCT/JP2019/021466, filed May 30, 2019, which claims priority to Japanese Patent Application No. 2018-104676, filed May 31, 2018, each expressly incorporated herein by reference in its entirety.

INCORPORATION BY REFERENCE

The instant application contains a Sequence Listing which is submitted in ASCII format via EFS-Web and is hereby incorporated by reference in its entirety. The ASCII copy, was created on Jun. 29, 2021, is named 4141-P2USCIP_Seq_List_FINAL_20210629_ST25, and is 172,032 bytes in size.

TECHNICAL FIELD

The present invention relates to anti-human Toll-like receptor (TLR) 7 antibodies for treating disorders and diseases.

BACKGROUND ART

In humans, 10 types of TLRs, which are pattern recognition molecules, are known to be present and form one family. Among them, TLR7 (variant 1) is a single transmembrane protein consisting of 1049 amino acids, and the possibility of it playing an important role in the pathogenesis of various inflammatory diseases and autoimmune diseases, by detecting single-stranded RNAs and playing a role in the biological defense reaction through production of type I interferons and cytokines and the like, has been suggested (Non Patent Literature 1). Further, TLR7 (variant 2), which is a single transmembrane protein consisting of 1049 amino acids, is also known to have the same function as TLR7 (variant 1) above (Non Patent Literature 2). In particular, there are many reports suggesting the involvement of TLR7 in diseases such as psoriasis and systemic lupus erythematosus, and it is expected that it is possible to treat such diseases by inhibiting the functions of TLR7 (Non Patent Literature 3).

While TLR7 deficiency acts to reduce symptoms in disease models, drugs capable of specifically inhibiting TLR7 are considered promising in treating inflammatory diseases or the like, based on reports suggesting that TLR9 deficiency is involved in disease progression (Non Patent Literature 4).

Until now, research and development of nucleic acids, low-molecular weight compounds, and the like for inhibiting human TLR7 have been attempted, but it is difficult to inhibit human TLR7 specifically using nucleic acids or low-molecular weight compounds. Further, a mouse anti-mouse TLR7 antibody is known as a TLR7 antibody (Patent Literature 1), but research and development of new human TLR7-specific inhibitors have been required.

CITATION LIST

Patent Literature

Patent Literature 1: International publication No. WO 2014/174704

Non Patent Literature

Non Patent Literature 1: Takeuchi O, Akira S. Cell. 2010 Mar. 19; 140 (6): 805-2

Non Patent Literature 2: Chuang T H, Ulevitch R J, Eur Cytokine Netw. 2000 September; 11 (3): 372-8

Non Patent Literature 3: Lyn-Cook B D, Xie C, Oates J, Treadwell E, Word B, Hammons G, Wiley K. Mol Immunol. 2014 September; 61 (1): 38-43.

Non Patent Literature 4: Christensen S R, Shupe J, Nickerson K, Kashgarian M, Flavell R A, Shlomchik M J Immunity. 2006 September; 25 (3): 417-28.

SUMMARY OF INVENTION

Technical Problem

It is an object of the present invention to provide an agent for treating and/or preventing immune inflammation-related diseases, allergic diseases, infections, and cancers.

Solution to Problem

In order to solve the aforementioned problems, the inventors have searched for a substance having the effect of treating and/or preventing immune inflammation-related diseases, allergic diseases, infections, and cancers, and acquired a mouse anti-human TLR7 antibody. They have accomplished the present invention by humanizing the mouse anti-human TLR7 antibody obtained and further modifying CDRs, frameworks, and variable regions of the humanized antibody.

That is, the present invention includes the following aspects.

(1) An antibody or an antigen-binding fragment of the antibody having the properties of:

(a) specifically binding to human TLR7 or monkey TLR7 and not binding to mouse TLR7 or rat TLR7; and (b) inhibiting a function of human TLR7 or monkey TLR7.

(2) The antibody or the antigen-binding fragment of the antibody according to (1) above, wherein the human TLR7 is a molecule consisting of the amino acid sequence set forth in SEQ ID NO: 2 or SEQ ID NO: 4, the monkey TLR7 is a molecule consisting of the amino acid sequence set forth in SEQ ID NO: 85, the mouse TLR7 is a molecule consisting of the amino acid sequence set forth in SEQ ID NO: 83, or the rat TLR7 is a molecule consisting of the amino acid sequence set forth in SEQ ID NO: 84.

(3) The antibody or the antigen-binding fragment of the antibody according to (1) or (2) above, having a competitive inhibitory activity for binding to human TLR7 with:

an antibody comprising a heavy chain with a heavy-chain variable region consisting of the amino acid sequence set forth in SEQ ID NO: 5 and a light chain with a light-chain variable region consisting of the amino acid sequence set forth in SEQ ID NO: 11;

an antibody comprising a heavy chain with a heavy-chain variable region consisting of the amino acid sequence set forth in SEQ ID NO: 7 and a light chain with a light-chain variable region consisting of the amino acid sequence set forth in SEQ ID NO: 13; or an antibody comprising a heavy chain with a heavy-chain variable region consisting of the amino acid sequence set forth in SEQ ID NO: 9 and a light chain with a light-chain variable region consisting of the amino acid sequence set forth in SEQ ID NO: 15.

(4) The antibody or the antigen-binding fragment of the antibody according to any one of (1) to (3) above, comprising:

(a) CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain;

(b) CDRH1 consisting of the amino acid sequence set forth in SEQ ID NO: 23, CDRH2 consisting of the amino acid sequence set forth in SEQ ID NO: 24 and CDRH3 consisting of the amino acid sequence set forth in SEQ ID NO: 25, as complementarity determining regions in the heavy chain, and CDRL1 consisting of the amino acid sequence set forth in SEQ ID NO: 26, CDRL2 consisting of the amino acid sequence set forth in SEQ ID NO: 27 and CDRL3 consisting of the amino acid sequence set forth in SEQ ID NO: 28, as complementarity determining regions in the light chain; or (c) CDRH1 consisting of the amino acid sequence set forth in SEQ ID NO: 29, CDRH2 consisting of the amino acid sequence set forth in SEQ ID NO: 30 and CDRH3 consisting of the amino acid sequence set forth in SEQ ID NO: 31, as complementarity determining regions in the heavy chain, and CDRL1 consisting of the amino acid sequence set forth in SEQ ID NO: 32, CDRL2 consisting of the amino acid sequence set forth in SEQ ID NO: 33 and CDRL3 consisting of the amino acid sequence set forth in SEQ ID NO: 34, as complementarity determining regions in the light chain.

(5) The antibody or the antigen-binding fragment of the antibody according to (4) above, comprising:

CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

(6) The antibody or the antigen-binding fragment of the antibody according to any one of (1) to (5) above, comprising:

(a) a heavy-chain variable region consisting of the amino acid sequence set forth in SEQ ID NO: 5 and a light-chain variable region consisting of the amino acid sequence set forth in SEQ ID NO: 11;

(b) a heavy-chain variable region consisting of the amino acid sequence set forth in SEQ ID NO: 7 and a light-chain variable region consisting of the amino acid sequence set forth in SEQ ID NO: 13; or (c) a heavy-chain variable region consisting of the amino acid sequence set forth in SEQ ID NO: 9 and a light-chain variable region consisting of the amino acid sequence set forth in SEQ ID NO: 15.

(7) The antibody or the antigen-binding fragment of the antibody according to any one of (1) to (6) above, wherein a constant region is a human-derived constant region.

(8) The antibody or the antigen-binding fragment of the antibody according to (7) above, comprising:

(a) a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36;

(b) a heavy chain consisting of an amino acid sequence at positions 20 to 471 in the amino acid sequence set forth in SEQ ID NO: 37 and a light chain consisting of an amino acid sequence at positions 21 to 233 in the amino acid sequence set forth in SEQ ID NO: 38, or (c) a heavy chain consisting of an amino acid sequence at positions 20 to 470 in the amino acid sequence set forth in SEQ ID NO: 39 and a light chain consisting of an amino acid sequence at positions 21 to 234 in the amino acid sequence set forth in SEQ ID NO: 40.

(9) The antibody or the antigen-binding fragment of the antibody according to any one of (1) to (8) above, being humanized.

(10) The antibody or the antigen-binding fragment of the antibody according to (9) above, comprising:

(I) a heavy-chain variable region consisting of an amino acid sequence selected from the group consisting of:

(a) the amino acid sequence set forth in SEQ ID NO: 41;
(b) the amino acid sequence set forth in SEQ ID NO: 42;
(c) an amino acid sequence having a homology of at least 95% or more to the sequence (a) or (b); and
(d) an amino acid sequence derived from the sequence (a) or (b) by deletion, substitution or addition of 1 to 10 amino acids; and a light-chain variable region consisting of an amino acid sequence selected from the group consisting of:

(e) the amino acid sequence set forth in SEQ ID NO: 43;
(f) the amino acid sequence set forth in SEQ ID NO: 44;
(g) an amino acid sequence having a homology of at least 95% or more to the sequence (e) or (f); and
(h) an amino acid sequence derived from the sequence (e) or (f) by deletion, substitution or addition of 1 to 10 amino acids; or (II) a heavy-chain variable region consisting of an amino acid sequence selected from the group consisting of:

(a) the amino acid sequence set forth in SEQ ID NO: 50;
(b) an amino acid sequence having a homology of at least 95% or more to the sequence (a); and
(c) an amino acid sequence derived from the sequence (a) by deletion, substitution or addition of 1 to 10 amino acids; and a light-chain variable region consisting of an amino acid sequence selected from the group consisting of:

(d) the amino acid sequence set forth in SEQ ID NO: 51;
(e) an amino acid sequence having a homology of at least 95% or more to the sequence (d); and
(f) an amino acid sequence derived from the sequence (d) by deletion, substitution or addition of 1 to 10 amino acids.

(11) The antibody or the antigen-binding fragment of the antibody according to (10) above, comprising:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43;

(d) a heavy-chain variable region consisting of the amino acid sequence set forth in SEQ ID NO: 42 and a light-chain variable region consisting of the amino acid sequence set forth in SEQ ID NO: 44; or (e) a heavy-chain variable region consisting of the amino acid sequence set forth in SEQ ID NO: 50 and a light-chain variable region consisting of the amino acid sequence set forth in SEQ ID NO: 51.

(12) The antibody or the antigen-binding fragment of the antibody according to (11) above, comprising a heavy-chain variable region consisting of the amino acid sequence set forth in SEQ ID NO: 42 and a light-chain variable region consisting of the amino acid sequence set forth in SEQ ID NO: 44.

(13) The antibody or the antigen-binding fragment of the antibody according to (11) above, comprising:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48;

(f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49;

(g) a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53; or (h) a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(14) The antibody or the antigen-binding fragment of the antibody according to (13) above, comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(15) An antibody or an antigen-binding fragment of the antibody having the properties of:

(a) specifically binding to human TLR7, (b) inhibiting a function of human TLR7, and (c) comprising:

(1) CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain;

(2) CDRH1 consisting of the amino acid sequence set forth in SEQ ID NO: 23, CDRH2 consisting of the amino acid sequence set forth in SEQ ID NO: 24 and CDRH3 consisting of the amino acid sequence set forth in SEQ ID NO: 25, as complementarity determining regions in the heavy chain, and CDRL1 consisting of the amino acid sequence set forth in SEQ ID NO: 26, CDRL2 consisting of the amino acid sequence set forth in SEQ ID NO: 27 and CDRL3 consisting of the amino acid sequence set forth in SEQ ID NO: 28, as complementarity determining regions in the light chain; or (3) CDRH1 consisting of the amino acid sequence set forth in SEQ ID NO: 29, CDRH2 consisting of the amino acid sequence set forth in SEQ ID NO: 30 and CDRH3 consisting of the amino acid sequence set forth in SEQ ID NO: 31, as complementarity determining regions in the heavy chain, and CDRL1 consisting of the amino acid sequence set forth in SEQ ID NO: 32, CDRL2 consisting of the amino acid sequence set forth in SEQ ID NO: 33 and CDRL3 consisting of the amino acid sequence set forth in SEQ ID NO: 34, as complementarity determining regions in the light chain.

(16) The antibody or the antigen-binding fragment of the antibody according to (15) above, comprising:

CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

(17) The antibody or the antigen-binding fragment of the antibody according to (15) or (16) above, comprising:

(a) a heavy-chain variable region consisting of the amino acid sequence set forth in SEQ ID NO: 5 and a light-chain variable region consisting of the amino acid sequence set forth in SEQ ID NO: 11;

(b) a heavy-chain variable region consisting of the amino acid sequence set forth in SEQ ID NO: 7 and a light-chain variable region consisting of the amino acid sequence set forth in SEQ ID NO: 13; or (c) a heavy-chain variable region consisting of the amino acid sequence set forth in SEQ ID NO: 9 and a light-chain variable region consisting of the amino acid sequence set forth in SEQ ID NO: 15.

(18) The antibody or the antigen-binding fragment of the antibody according to any one of (15) to (17) above, wherein a constant region is a human-derived constant region.

(19) The antibody or the antigen-binding fragment of the antibody according to (18) above, comprising:

(a) a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36;

(b) a heavy chain consisting of an amino acid sequence at positions 20 to 471 in the amino acid sequence set forth in SEQ ID NO: 37 and a light chain consisting of an amino acid sequence at positions 21 to 233 in the amino acid sequence set forth in SEQ ID NO: 38, or (c) a heavy chain consisting of an amino acid sequence at positions 20 to 470 in the amino acid sequence set forth in SEQ ID NO: 39 and a light chain consisting of an amino acid sequence at positions 21 to 234 in the amino acid sequence set forth in SEQ ID NO: 40.

(20) The antibody or the antigen-binding fragment of the antibody according to any one of (15) to (19) above, being humanized.

(21) The antibody or the antigen-binding fragment of the antibody according to (20) above, comprising:

(I) a heavy-chain variable region consisting of an amino acid sequence selected from the group consisting of:

(a) the amino acid sequence set forth in SEQ ID NO: 41;
(b) the amino acid sequence set forth in SEQ ID NO: 42;
(c) an amino acid sequence having a homology of at least 95% or more to the sequence (a) or (b); and
(d) an amino acid sequence derived from the sequence (a) or (b) by deletion, substitution or addition of 1 to 10 amino acids; and a light-chain variable region consisting of an amino acid sequence selected from the group consisting of:

(e) the amino acid sequence set forth in SEQ ID NO: 43;
(f) the amino acid sequence set forth in SEQ ID NO: 44;
(g) an amino acid sequence having a homology of at least 95% or more to the sequence (e) or (f); and
(h) an amino acid sequence derived from the sequence (e) or (f) by deletion, substitution or addition of 1 to 10 amino acids; or (II) a heavy-chain variable region consisting of an amino acid sequence selected from the group consisting of:

(a) the amino acid sequence set forth in SEQ ID NO: 50;
(b) an amino acid sequence having a homology of at least 95% or more to the sequence (a); and
(c) an amino acid sequence derived from the sequence (a) by deletion, substitution or addition of 1 to 10 amino acids; and a light-chain variable region consisting of an amino acid sequence selected from the group consisting of:

(d) the amino acid sequence set forth in SEQ ID NO: 51;
(e) an amino acid sequence having a homology of at least 95% or more to the sequence (d); and
(f) an amino acid sequence derived from the sequence (d) by deletion, substitution or addition of 1 to 10 amino acids.

(22) The antibody or the antigen-binding fragment of the antibody according to (21) above, comprising:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43;

(d) a heavy-chain variable region consisting of the amino acid sequence set forth in SEQ ID NO: 42 and a light-chain variable region consisting of the amino acid sequence set forth in SEQ ID NO: 44; or (e) a heavy-chain variable region consisting of the amino acid sequence set forth in SEQ ID NO: 50 and a light-chain variable region consisting of the amino acid sequence set forth in SEQ ID NO: 51.

(23) The antibody or the antigen-binding fragment of the antibody according to (22) above, comprising a heavy-chain variable region consisting of the amino acid sequence set forth in SEQ ID NO: 42 and a light-chain variable region consisting of the amino acid sequence set forth in SEQ ID NO: 44.

(24) The antibody or the antigen-binding fragment of the antibody according to (22) above, comprising:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48;

(f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49;

(g) a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53; or (h) a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(25) The antibody or the antigen-binding fragment of the antibody according to (24) above, comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(26) An antibody or an antigen-binding fragment of the antibody comprising a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48.

(27) An antibody or an antigen-binding fragment of the antibody comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48.

(28) An antibody or an antigen-binding fragment of the antibody comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

(29) An antibody or an antigen-binding fragment of the antibody comprising a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

(30) An antibody or an antigen-binding fragment of the antibody comprising a heavy chain consisting of an amino acid sequence at positions 20 to 471 in the amino acid sequence set forth in SEQ ID NO: 52 and a light chain consisting of an amino acid sequence at positions 21 to 233 in the amino acid sequence set forth in SEQ ID NO: 53.

(31) An antibody or an antigen-binding fragment of the antibody comprising a heavy chain consisting of an amino acid sequence at positions 20 to 468 in the amino acid sequence set forth in SEQ ID NO: 54 and a light chain consisting of an amino acid sequence at positions 21 to 233 in the amino acid sequence set forth in SEQ ID NO: 53.

(32) The antibody or the antigen-binding fragment of the antibody according to any one of (26) to (31) above, having the properties of:

(a) specifically binding to human TLR7; and (b) inhibiting a function of human TLR7.

(33) The antigen-binding fragment of the antibody according to any one of (1) to (32) above, wherein the antigen-binding fragment is selected from the group consisting of Fab, $F(ab)_2$, Fab' and Fv.

(34) A polynucleotide comprising a polynucleotide sequence encoding the antibody or the antigen-binding fragment of the antibody according to any one of (1) to (33) above.

(35) The polynucleotide according to (34) above, comprising:

(1) a polynucleotide sequence encoding CDRH1 consisting of the amino acid sequence set forth in SEQ ID NO: 17, a polynucleotide sequence encoding CDRH2 consisting of the amino acid sequence set forth in SEQ ID NO: 18 and a polynucleotide sequence encoding CDRH3 consisting of the amino acid sequence set forth in SEQ ID NO: 19, and a polynucleotide sequence encoding CDRL1 consisting of the amino acid sequence set forth in SEQ ID NO: 20, a polynucleotide sequence encoding CDRL2 consisting of the amino acid sequence set forth in SEQ ID NO: 21 and a polynucleotide sequence encoding CDRL3 consisting of the amino acid sequence set forth in SEQ ID NO: 22;

(2) a polynucleotide sequence encoding CDRH1 consisting of the amino acid sequence set forth in SEQ ID NO: 23, a polynucleotide sequence encoding CDRH2 consisting of the amino acid sequence set forth in SEQ ID NO: 24 and a polynucleotide sequence encoding CDRH3 consisting of the amino acid sequence set forth in SEQ ID NO: 25, and a polynucleotide sequence encoding CDRL1 consisting of the amino acid sequence set forth in SEQ ID NO: 26, a polynucleotide sequence encoding CDRL2 consisting of the amino acid sequence set forth in SEQ ID NO: 27 and a polynucleotide sequence encoding CDRL3 consisting of the amino acid sequence set forth in SEQ ID NO: 28; or (3) a polynucleotide sequence encoding CDRH1 consisting of the amino acid sequence set forth in SEQ ID NO: 29, a polynucleotide sequence encoding CDRH2 consisting of the amino acid sequence set forth in SEQ ID NO: 30 and a polynucleotide sequence encoding CDRH3 consisting of the amino acid sequence set forth in SEQ ID NO: 31, and a polynucleotide sequence encoding CDRL1 consisting of the amino acid sequence set forth in SEQ ID NO: 32, a polynucleotide sequence encoding CDRL2 consisting of the amino acid sequence set forth in SEQ ID NO: 33 and a polynucleotide sequence encoding CDRL3 consisting of the amino acid sequence set forth in SEQ ID NO: 34.

(36) The polynucleotide according to (35) above, comprising:

(I) a polynucleotide sequence selected from the group consisting of:

(a) a polynucleotide sequence encoding the heavy-chain variable region set forth in SEQ ID NO: 77;

(b) a polynucleotide sequence encoding the heavy-chain variable region set forth in SEQ ID NO: 78; and (c) a polynucleotide sequence of a polynucleotide which hybridizes with a polynucleotide consisting of a polynucleotide sequence complementary to the polynucleotide sequence (a) or (b) under stringent conditions; and a polynucleotide sequence selected from the group consisting of:

(d) a polynucleotide sequence encoding the light-chain variable region set forth in SEQ ID NO: 79;

(e) a polynucleotide sequence encoding the light-chain variable region set forth in SEQ ID NO: 80; and (f) a polynucleotide sequence of a polynucleotide which hybridizes with a polynucleotide consisting of a polynucleotide sequence complementary to the polynucleotide sequence (d) or (e) under stringent conditions; or (II) a polynucleotide sequence selected from the group consisting of:

(a) a polynucleotide sequence encoding the heavy-chain variable region set forth in SEQ ID NO: 81; and (b) a polynucleotide sequence of a polynucleotide which hybridizes with a polynucleotide consisting of a polynucleotide sequence complementary to the polynucleotide sequence (a) under stringent conditions; and a polynucleotide sequence selected from the group consisting of:

(c) a polynucleotide sequence encoding the light-chain variable region set forth in SEQ ID NO: 82; and (d) a polynucleotide sequence of a polynucleotide which hybridizes with a polynucleotide consisting of a polynucleotide sequence complementary to the polynucleotide sequence (c) under stringent conditions.

(37) The polynucleotide according to (36) above, comprising:

(a) a polynucleotide sequence encoding the heavy-chain variable region set forth in SEQ ID NO: 77 and a polynucleotide sequence encoding the light-chain variable region set forth in SEQ ID NO: 79;

(b) a polynucleotide sequence encoding the heavy-chain variable region set forth in SEQ ID NO: 77 and a polynucleotide sequence encoding the light-chain variable region set forth in SEQ ID NO: 80;

(c) a polynucleotide sequence encoding the heavy-chain variable region set forth in SEQ ID NO: 78 and a polynucleotide sequence encoding the light-chain variable region set forth in SEQ ID NO: 79;

(d) a polynucleotide sequence encoding the heavy-chain variable region set forth in SEQ ID NO: 78 and a polynucleotide sequence encoding the light-chain variable region set forth in SEQ ID NO: 80; or (e) a polynucleotide sequence encoding the heavy-chain variable region set forth in SEQ ID NO: 81 and a polynucleotide sequence encoding the light-chain variable region set forth in SEQ ID NO: 82.

(38) An expression vector comprising the polynucleotide according to any one of (34) to (37) above.

(39) A host cell transformed with the expression vector according to (38) above.

(40) The host cell according to (39) above, wherein the host cell is a eukaryotic cell.

(41) A method for producing an antibody or an antigen-binding fragment of the antibody, comprising the steps of:

culturing the host cell according to (39) or (40) above; and collecting the antibody or the fragment of interest from the culture obtained in the above step.

(42) An antibody or an antigen-binding fragment of the antibody obtained by the production method according to (41).

(43) The antibody according to any one of (1) to (32) above, comprising one or more modifications selected from the group consisting of glycosylation to N-linkage, glycosylation to O-linkage, N-terminal processing, C-terminal processing, deamidation, isomerization of aspartic acid, oxidation of methionine, addition of a methionine residue to N-terminal, amidation of a proline residue, and deletion of one or two amino acids at the carboxyl terminus of the heavy chain.

(44) The antibody according to (43) above, comprising: two heavy chains consisting of one kind of or a combination of any two kinds of heavy chains selected from the group consisting of the full length and deletion variants with one or two amino acids deleted at the carboxyl terminus.

(45) The antibody according to (44) above, wherein one amino acid is deleted at the carboxyl terminus in each of the two heavy chains.

(46) The antibody according to any one of (43) to (45) above, wherein a proline residue at the carboxyl terminus of the heavy chain is further amidated.

(47) A pharmaceutical composition for treating and/or preventing a disease, comprising: at least one of the antibodies or the antigen-binding fragments of the antibodies according to (1) to (33) and (42) to (46) above, or the expression vector according to (38) as an active ingredient.

(48) The pharmaceutical composition according to (47) above, for treating a disease caused by a function of human TLR7.

(49) The pharmaceutical composition according to (48) above, wherein the disease caused by a function of human TLR7 is an immune inflammation-related disease, an allergic disease, an infection or a cancer.

(50) The pharmaceutical composition according to (49) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(51) The pharmaceutical composition according to (49) or (50) above, wherein the immune inflammation-related disease is systemic lupus erythematosus.

(52) The pharmaceutical composition according to any one of (47) to (51) above, to be used in combination with an immunosuppressant, an anti-inflammatory drug, an antiallergic agent, an anti-infective agent, or an anticancer agent.

(53) A method for treating a disease caused by a function of human TLR7, comprising: administering at least one of the antibodies or the antigen-binding fragments of the antibodies according to (1) to (33) and (42) to (46) above to an individual.

(54) A method for treating a disease caused by a function of human TLR7, comprising administering at least one of the antibodies or the antigen-binding fragments of the antibodies according to (1) to (33) and (42) to (46) above together with an immunosuppressant, an anti-inflammatory drug, an antiallergic agent, an anti-infective agent or an anticancer agent, simultaneously, separately or sequentially to an individual.

(55) The treatment method according to (53) or (54) above, wherein the disease caused by a function of human TLR7 is an immune inflammation-related disease, an allergic disease, an infection or a cancer.

(56) The treatment method according to (55) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(57) The treatment method according to (55) or (56) above, wherein the immune inflammation-related disease is systemic lupus erythematosus.

(58) The antibody or the antigen-binding fragment of the antibody according to any one of (1) to (33) and (42) to (46) above, or the expression vector according to (38) above, to be used for treating or preventing a disease caused by a function of human TLR7.

(59) The antibody, the antigen-binding fragment of the antibody, or the expression vector according to (58) above, wherein the disease caused by a function of human TLR7 is an immune inflammation-related disease, an allergic disease, an infection or a cancer.

(60) The antibody, the antigen-binding fragment of the antibody, or the expression vector according to (59) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(61) The antibody, the antigen-binding fragment of the antibody, or the expression vector according to (59) or (60) above, wherein the immune inflammation-related disease is systemic lupus erythematosus.

(62) The antibody, the antigen-binding fragment of the antibody, or the expression vector according to any one of (58) to (61) above, to be used in combination with an immunosuppressant, an anti-inflammatory drug, an antiallergic agent, an anti-infective agent or an anticancer agent.

(63) Use of the antibody or the antigen-binding fragment of the antibody according to any one of (1) to (33) and (42) to

(46) above, or the expression vector according to (38) above, for producing a therapeutic agent or a preventive agent for a disease caused by a function of human TLR7.

(64) The use according to (63) above, wherein the disease caused by a function of human TLR7 is an immune inflammation-related disease, an allergic disease, an infection or a cancer.

(65) The use according to (64) above, wherein the immune inflammation-related disease is systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease or muscular dystrophy.

(66) The use according to (64) or (65) above, wherein the immune inflammation-related disease is systemic lupus erythematosus.

(67) The use according to any one of (63) to (66) above, wherein the therapeutic agent or the preventive agent is used in combination with an immunosuppressant, an anti-inflammatory drug, an antiallergic agent, an anti-infective agent or an anticancer agent.

Advantageous Effects of Invention

According to the present invention, an agent having a mechanism of action of inhibiting a function of TLR7 for treating and/or preventing immune inflammation-related diseases, allergic diseases, infections, and cancers can be obtained.

BRIEF DESCRIPTION OF DRAWINGS

FIG. 1 shows the amino acid sequence (SEQ ID NO: 2) of human TLR7 (variant 1).

FIG. 2 shows the amino acid sequence (SEQ ID NO: 4) of human TLR7 (variant 2).

FIG. 3 shows the amino acid sequence (SEQ ID NO: 83) of mouse TLR7.

FIG. 4 shows the amino acid sequence (SEQ ID NO: 84) of rat TLR7.

FIG. 5 shows the amino acid sequence (SEQ ID NO: 85) of monkey TLR7.

FIG. 7 shows the amino acid sequence (SEQ ID NO: 35) of the heavy chain of the cAT01 antibody, which includes the signal sequence thereof, and the amino acid sequence (SEQ ID NO: 36) of the light chain of the cAT01 antibody, which includes the signal sequence thereof. In the heavy-chain amino acid sequence, the amino acid sequence at positions 1 to 19 is the signal sequence, the amino acid sequence at positions 20 to 135 is the heavy-chain variable region, and the amino acid sequence at positions 136 to 465 is the heavy-chain constant region. In the light-chain amino acid sequence, the amino acid sequence at positions 1 to 20 is the signal sequence, the amino acid sequence at positions 21 to 126 is the light-chain variable region, and the amino acid sequence at positions 127 to 233 is the light-chain constant region.

FIG. 8 shows the amino acid sequence (SEQ ID NO: 37) of the heavy chain of the cNB7 antibody, which includes the signal sequence thereof, and the amino acid sequence (SEQ ID NO: 38) of the light chain of the cNB7 antibody, which includes the signal sequence thereof. In the heavy-chain amino acid sequence, the amino acid sequence at positions 1 to 19 is the signal sequence, the amino acid sequence at positions 20 to 141 is the heavy-chain variable region, and the amino acid sequence at positions 142 to 471 is the heavy-chain constant region. In the light-chain amino acid sequence, the amino acid sequence at positions 1 to 20 is the signal sequence, the amino acid sequence at positions 21 to 126 is the light-chain variable region, and the amino acid sequence at positions 127 to 233 is the light-chain constant region.

FIG. 9 shows the amino acid sequence (SEQ ID NO: 39) of the heavy chain of the cFAN2 antibody, which includes the signal sequence thereof, and the amino acid sequence (SEQ ID NO: 40) of the light chain of the cFAN2 antibody, which includes the signal sequence thereof. In the heavy-chain amino acid sequence, the amino acid sequence at positions 1 to 19 is the signal sequence, the amino acid sequence at positions 20 to 140 is the heavy-chain variable region, and the amino acid sequence at positions 141 to 470 is the heavy-chain constant region. In the light-chain amino acid sequence, the amino acid sequence at positions 1 to 20 is the signal sequence, the amino acid sequence at positions 21 to 127 is the light-chain variable region, and the amino acid sequence at positions 128 to 234 is the light-chain constant region.

FIG. 11 shows the amino acid sequence (SEQ ID NO: 45) of the heavy chain of huAT01_H1_IgG1LALA, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 12 shows the amino acid sequence (SEQ ID NO: 46) of the heavy chain of huAT01_H3_IgG1LALA, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 13 shows the amino acid sequence (SEQ ID NO: 47) of the heavy chain of huAT01_H3_IgG4Pro, which includes the signal sequence thereof, and which is a humanized heavy chain. In the sequence, the amino acid sequence at positions 1 to 19 is the signal sequence, the amino acid sequence at positions 20 to 135 is the variable region, and the amino acid sequence at positions 136 to 462 is the constant region. Further, the amino acid sequence at positions 45 to 54 is CDRH1, the amino acid sequence at positions 69 to 78 is CDRH2, and the amino acid sequence at positions 118 to 124 is CDRH3.

FIG. 14 shows the comparison of the amino acid sequence (SEQ ID NO: 5) of the variable region of cAT01_H, which is the heavy chain of chimeric antibody cAT01 (which will be hereinafter referred to as cAT01_H), the amino acid sequence (SEQ ID NO: 41) of the variable region of humanized antibody heavy chain huAT01_H1_IgG1LALA (which will be hereinafter referred to as huAT01_H1), and the amino acid sequence (SEQ ID NO: 42) of the variable region of humanized antibody heavy chain huAT01_H3_IgG1LALA (which will be hereinafter referred to as huAT01_H3). In the sequences of huAT01_H1 and huAT01_H3, the symbol "•" represents the same amino acid residue as that of cAT01_H, and a substituted amino acid residue is shown in the site where the amino acid residue is described.

FIG. 15 shows the amino acid sequence (SEQ ID NO: 48) of the light chain of huAT01_L1, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 16 shows the amino acid sequence (SEQ ID NO: 49) of the light chain of huAT01_L2, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 17 shows the comparison of the amino acid sequence (SEQ ID NO: 11) of the variable region of cAT01_L, which is the light chain of chimeric antibody cAT01 (which will be hereinafter referred to as cAT01_L), the amino acid sequence (SEQ ID NO: 43) of the variable region of humanized antibody light chain huAT01_L1 (which will be hereinafter referred to as huAT01_L1), and the amino acid sequence (SEQ ID NO: 44) of the variable region of humanized antibody light chain huAT01_L2 (which will be hereinafter referred to as huAT01_L2). In the sequences of huAT01_L1 and huAT01_L2, the symbol "•" represents the same amino acid residue as that of cAT01_L, and a substituted amino acid residue is shown in the site where the amino acid residue is described.

FIG. 18 shows the amino acid sequence (SEQ ID NO: 52) of the heavy chain of huNB7_H3_IgG1LALA, which includes the signal sequence thereof and which is a humanized heavy chain. In the sequence, the amino acid sequence at positions 1 to 19 is the signal sequence, the amino acid sequence at positions 20 to 141 is the variable region, and the amino acid sequence at positions 142 to 471 is the constant region. Further, the amino acid sequence at positions 45 to 55 is CDRH1, the amino acid sequence at positions 70 to 78 is CDRH2, and the amino acid sequence at positions 118 to 130 is CDRH3.

FIG. 19 shows the amino acid sequence (SEQ ID NO: 54) of the heavy chain of huNB7_H3_IgG4Pro, which includes the signal sequence thereof and which is a humanized heavy chain. In the sequence, the amino acid sequence at positions 1 to 19 is the signal sequence, the amino acid sequence at positions 20 to 141 is the variable region, and the amino acid sequence at positions 142 to 468 is the constant region. Further, the amino acid sequence at positions 45 to 55 is CDRH1, the amino acid sequence at positions 70 to 78 is CDRH2, and the amino acid sequence at positions 118 to 130 is CDRH3.

FIG. 20 shows the comparison of the amino acid sequence (SEQ ID NO: 7) of the variable region of cNB7_H, which is the heavy chain of chimeric antibody cNB7 (which will be hereinafter referred to as cNB7_H) and the amino acid sequence (SEQ ID NO: 50) of the variable region of humanized antibody heavy chain huNB7_H3_IgG1LALA (which will be hereinafter referred to as huNB7_H3). In huNB7_H3, the symbol "•" represents the same amino acid residue as that of cNB7_H, and a substituted amino acid residue is shown in the site where the amino acid residue is described.

FIG. 21 shows the amino acid sequence (SEQ ID NO: 53) of the light chain of huNB7_L3, which includes the signal sequence thereof and which is a humanized light chain. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

FIG. 22 shows the comparison of the amino acid sequence (SEQ ID NO: 13) of the variable region of cNB7_L, which is the light chain of chimeric antibody cNB7 (which will be hereinafter referred to as cNB7_L) and the amino acid sequence (SEQ ID NO: 51) of the variable region of humanized antibody light chain huNB7_L3 (which will be hereinafter referred to as huNB7_L3). In huNB7_L3, the symbol "•" represents the same amino acid residue as that of cNB7_L, and a substituted amino acid residue is shown in the site where the amino acid residue is described.

FIG. 24-1 shows the amino acid sequence (SEQ ID NO: 17) of CDRH1 of AT01 antibody, the amino acid sequence (SEQ ID NO: 18) of CDRH2 thereof, the amino acid sequence (SEQ ID NO: 19) of CDRH3 thereof, the amino acid sequence (SEQ ID NO: 20) of CDRL1 thereof, the amino acid sequence (SEQ ID NO: 21) of CDRL2 thereof, and the amino acid sequence (SEQ ID NO: 22) of CDRL3 thereof. FIG. 24-2 shows the amino acid sequence (SEQ ID NO: 23) of CDRH1 of NB7 antibody, the amino acid sequence (SEQ ID NO: 24) of CDRH2 thereof, the amino acid sequence (SEQ ID NO: 25) of CDRH3 thereof, the amino acid sequence (SEQ ID NO: 26) of CDRL1 thereof, the amino acid sequence (SEQ ID NO: 27) of CDRL2 thereof, and the amino acid sequence (SEQ ID NO: 28) of CDRL3 thereof. FIG. 24-3 shows the amino acid sequence (SEQ ID NO: 29) of CDRH1 of FAN2 antibody, the amino acid sequence (SEQ ID NO: 30) of CDRH2 thereof, the amino acid sequence (SEQ ID NO: 31) of CDRH3 thereof, the amino acid sequence (SEQ ID NO: 32) of CDRL1 thereof, the amino acid sequence (SEQ ID NO: 33) of CDRL2 thereof, and the amino acid sequence (SEQ ID NO: 34) of CDRL3 thereof.

DESCRIPTION OF EMBODIMENTS

Figure 6:
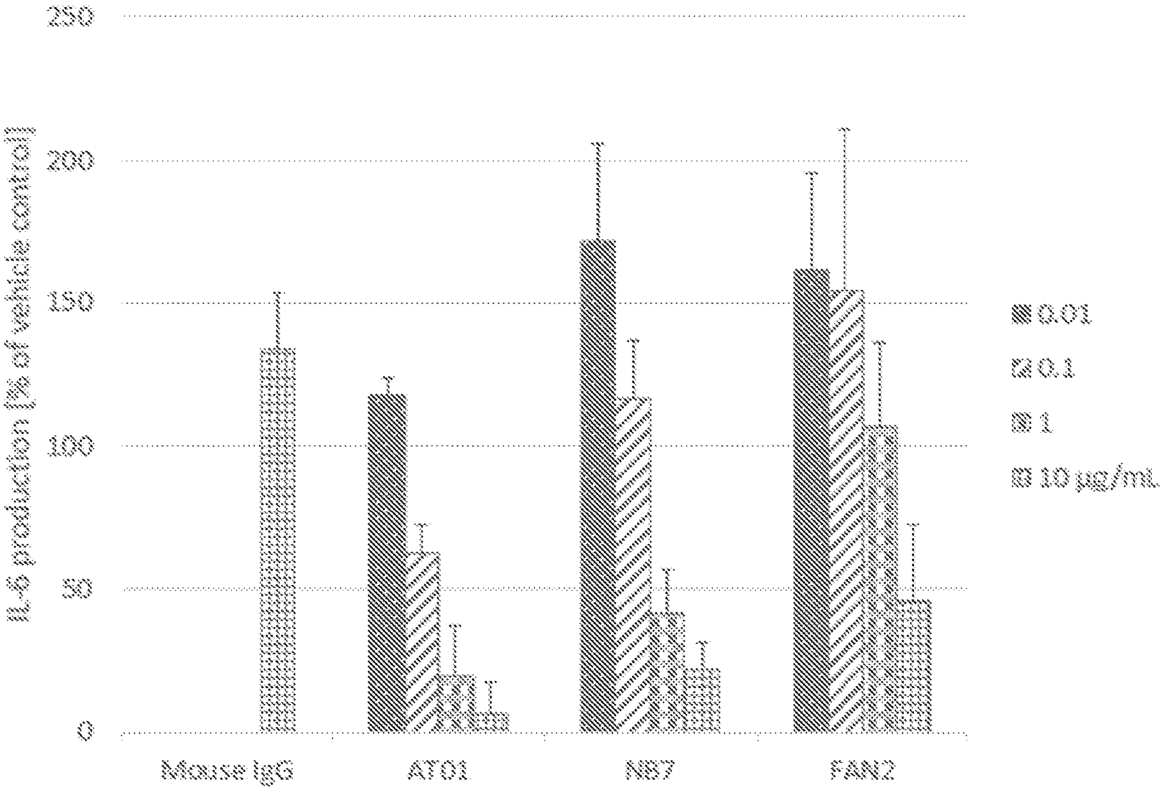
FIG. 6 is a graph showing that the AT01 antibody, the NB7 antibody, and the FAN2 antibody suppress the production of IL-6 from human peripheral blood mononuclear cells (which will be hereinafter referred to as PBMCs) treated with CL-264 in a concentration dependent manner.

In this description, the term "gene" includes not only DNA but also mRNA, cDNA, and cRNA.

In this description, the term "polynucleotide" is used in the same meaning as "nucleic acid" and also includes DNA, RNA, probes, oligonucleotides, and primers.

In this description, the terms "polypeptide" and "protein" are used without distinction.

In this description, the term "RNA fraction" means a fraction containing RNA.

In this description, the term "cells" includes cells in animal individuals and cultured cells.

In this description, the term "TLR7" is used to have the same meaning as TLR7 protein.

In this description, the term "antigen-binding fragment of an antibody" means a partial fragment of an antibody having binding activity to an antigen and includes Fab, $F(ab')_2$, Fv, scFv, diabodies, linear antibodies, multispecific antibodies formed from antibody fragments, and the like. Further, an antigen-binding fragment of an antibody also includes Fab' which is a monovalent fragment in a variable region of an antibody obtained by treating $F(ab')_2$ under reducing conditions. However, there is no limitation to these molecules as long as the fragment has an ability to bind to an antigen. Further, the antigen-binding fragment includes not only those obtained by treating a full-length molecule of an antibody protein with a suitable enzyme but also a protein produced in a suitable host cell using a genetically engineered antibody gene.

Complementarity determining regions (CDR: Complementarity Determining Regions) are known to be present at three points in each of the heavy and light chains of an antibody molecule. The complementarity determining regions, which are also called hypervariable regions, are present in the variable regions of the heavy and light chains of an antibody at sites where the variability of the primary structure is particularly high. In the primary structure of the polypeptide chain in each of the heavy and light chains, the complementarity determining regions are separately present at three points. Concerning the complementarity determining regions of an antibody, the complementarity determining regions of the heavy chain are expressed as CDRH1, CDRH2, and CDRH3 from the amino-terminal side of the heavy-chain amino acid sequence, and the complementarity determining regions of the light chain are expressed as CDRL1, CDRL2, and CDRL3 from the amino-terminal side of the light-chain amino acid sequence, in this description. These sites are adjacent to each other on the three-dimensional structure and determine the specificity for the antigen to be bound. Further, the amino chain sequence of each CDR is described according to the AbM definition (Martin, A. C. R., Cheetham, J. C. and Rees, A. R. (1989) Proc. Natl Acad. Sci. USA, 86, 9268-9272).

In the present invention, the phrase "hybridizing under stringent conditions" means hybridizing at 68° C. in a commercially available hybridization solution, ExpressHyb Hybridization Solution (Clontech Laboratories, Inc.) or hybridizing under conditions which allow hybridization at 68° C. in the presence of 0.7 to 1.0-M NaCl using a filter to which DNA is immobilized and subsequent identification by washing at 68° C. using an SSC solution of 0.1 to 2-fold concentration (SSC of 1-fold concentration composed of 150-mM NaCl and 15-mM sodium citrate) or conditions equivalent thereto.

1. TLR7

Human TLR7 used in the present invention can be directly purified from human B cells or dendritic cells or prepared by adjusting the cell membrane fractions of the aforementioned cells for use. Further, human TLR7 can be obtained by in-vitro synthesis or production in host cells by genetic engineering. In genetic engineering, human TLR7 is expressed specifically by being integrated into a vector capable of expressing human TLR7 cDNA, followed by synthesis in a solution containing enzymes, substrates, and energy substances that are necessary for transcription and translation, or human TLR7 is expressed by transformation of host cells of other prokaryotes or eukaryotes, so that such a protein can be obtained.

Likewise, monkey TLR7, mouse TLR7, and rat TLR7 can be directly purified from TLR7-expressing cells of monkeys, mice, and rats, respectively, and used, or prepared by adjusting the cell membrane fractions of the aforementioned cells for use. Further, monkey TLR7, mouse TLR7, and rat TLR7 can be obtained by in-vitro synthesis or production in host cells by genetic engineering.

The polynucleotide sequences encoding the amino acid sequences of human TLR7 (variant 1) and human TLR7 (variant 2) are set forth in SEQ ID NO: 1 and SEQ ID NO: 3, respectively in the Sequence Listing, and the amino acid sequences of human TLR7 (variant 1) and human TLR7 (variant 2) are set forth in SEQ ID NO: 2 and SEQ ID NO: 4, respectively in the Sequence Listing.

The cDNA of human TLR7 can be obtained, for example, by the so-called PCR method, with polymerase chain reaction (which will be hereinafter referred to as "PCR") (Saiki, R. K., et al., Science, (1988) 239, 487-49) using a cDNA library from an organ expressing the mRNA of human TLR7 as a template and a primer which specifically amplifies the cDNA of human TLR7.

The cDNA of human TLR7 also includes a polynucleotide which hybridizes with a polynucleotide consisting of a nucleotide sequence complementary to the nucleotide sequence encoding human TLR7 under stringent conditions and encodes a protein having a biological activity equivalent to human TLR7. Further, the cDNA of human TLR7 also includes a splicing variant transcribed from the human TLR7 gene locus or a polynucleotide which hybridizes with the splicing variant under stringent conditions and encodes a protein having a biological activity equivalent to human TLR7.

Further, human TLR7 also includes a protein which consists of the amino acid sequence of human TLR7 or the amino acid sequence excluding the signal sequence with one, two, three, four, or five amino acids substituted, deleted, or added and has a biological activity equivalent to human TLR7. Further, human TLR7 also includes a protein which consists of the amino acid sequence encoded by the splicing variant transcribed from the human TLR7 gene locus or the amino acid sequence with one, two, three, four, or five amino acids substituted, deleted, or added and has a biological activity equivalent to human TLR7.

The polynucleotide sequence encoding the amino acid sequence of monkey TLR7 is set forth in SEQ ID NO: 58 in the Sequence Listing, and the amino acid sequence of monkey TLR7 is set forth in SEQ ID NO: 85 in the Sequence Listing.

The cDNA of monkey TLR7 can be obtained, for example, by the PCR method using a cDNA library from an organ expressing the mRNA of monkey TLR7 as a template and a primer which specifically amplifies the cDNA of monkey TLR7.

The cDNA of monkey TLR7 also includes a polynucleotide which hybridizes with a polynucleotide consisting of a nucleotide sequence complementary to the nucleotide sequence encoding monkey TLR7 under stringent conditions and encodes a protein having a biological activity equivalent to monkey TLR7. Further, the cDNA of monkey TLR7 also includes a splicing variant transcribed from the monkey TLR7 gene locus or a polynucleotide which hybridizes with the splicing variant under stringent conditions and encodes a protein having a biological activity equivalent to monkey TLR7.

Further, monkey TLR7 also includes a protein which consists of the amino acid sequence of monkey TLR7 or the amino acid sequence excluding the signal sequence with one, two, three, four, or five amino acids substituted, deleted, or added and has a biological activity equivalent to monkey TLR7. Further, monkey TLR7 also includes a protein which consists of the amino acid sequence encoded by the splicing variant transcribed from the monkey TLR7 gene locus or the amino acid sequence with one, two, three, four, or five amino acids substituted, deleted, or added and has a biological activity equivalent to monkey TLR7.

The polynucleotide sequence encoding the amino acid sequence of monkey TLR7 is set forth in SEQ ID NO: 58 in the Sequence Listing, and the amino acid sequence of monkey TLR7 is set forth in SEQ ID NO: 85 in the Sequence Listing.

The cDNA of monkey TLR7 can be obtained, for example, by the PCR method using a cDNA library from an organ expressing the mRNA of monkey TLR7 as a template and a primer which specifically amplifies the cDNA of monkey TLR7.

The polynucleotide sequence encoding the amino acid sequence of mouse TLR7 is set forth in SEQ ID NO: 56 in the Sequence Listing, and the amino acid sequence of mouse TLR7 is set forth in SEQ ID NO: 83 in the Sequence Listing.

The cDNA of mouse TLR7 can be obtained, for example, by the PCR method using a cDNA library from an organ expressing the mRNA of mouse TLR7 as a template and a primer which specifically amplifies the cDNA of mouse TLR7.

The polynucleotide sequence encoding the amino acid sequence of rat TLR7 is set forth in SEQ ID NO: 57 in the Sequence Listing, and the amino acid sequence of rat TLR7 is set forth in SEQ ID NO: 84 in the Sequence Listing.

The cDNA of rat TLR7 can be obtained, for example, by the PCR method using a cDNA library from an organ expressing the mRNA of rat TLR7 as a template and a primer which specifically amplifies the cDNA of rat TLR7.

2. Anti-TLR7 Antibody and Production Thereof

The present invention provides an antibody or an antigen-binding fragment of the antibody having the properties of:
(a) specifically binding to human TLR7 or monkey TLR7 and not binding to mouse TLR7 or rat TLR7; and
(b) inhibiting a function of the human TLR7 or the monkey TLR7.

The antibody or the antigen-binding fragment of the antibody of the present invention binds specifically to human TLR7 or monkey TLR7 and inhibits the functions thereof.

The binding activity of the antibody or the antigen-binding fragment of the antibody to TLR7 is evaluated by flow cytometry analysis according to a conventional method.

In this description, inhibiting a function of TLR7 means suppressing the production of IL-6 and/or type I interferon by TLR7-expressing cells. The activity of inhibiting a function of TLR7 is evaluated by incubating TLR7-expressing cells (for example, PBMCs) in vitro in the presence of the antibody or the antigen-binding fragment of the antibody and measuring the concentration of IL-6 or type I interferon in the culture supernatant.

In one embodiment of the present invention, the human TLR7 is a molecule consisting of the amino acid sequence set forth in SEQ ID NO: 2 or SEQ ID NO: 4, the monkey TLR7 is a molecule consisting of the amino acid sequence set forth in SEQ ID NO: 85, the mouse TLR7 is a molecule consisting of the amino acid sequence set forth in SEQ ID NO: 83, or the rat TLR7 is a molecule consisting of the amino acid sequence set forth in SEQ ID NO: 84. For example, the human TLR7 can be a molecule consisting of the amino acid sequence set forth in SEQ ID NO: 2 or SEQ ID NO: 4, the monkey TLR7 can be a molecule consisting of the amino acid sequence set forth in SEQ ID NO: 85, the mouse TLR7 can be a molecule consisting of the amino acid sequence set forth in SEQ ID NO: 83, and the rat TLR7 can be a molecule consisting of the amino acid sequence set forth in SEQ ID NO: 84, in the present invention.

For example, the antibody or the antigen-binding fragment of the antibody of the present invention can be an antibody against human TLR7 or an antigen-binding fragment of the antibody having the properties of:
(a) specifically binding to human TLR7 and not binding to mouse TLR7 and/or rat TLR7; and
(b) inhibiting a function of human TLR7, wherein the human TLR7 is a molecule consisting of the amino acid sequence set forth in SEQ ID NO: 2 or SEQ ID NO: 4, the mouse TLR7 is a molecule consisting of the amino acid sequence set forth in SEQ ID NO: 83, and the rat TLR7 is a molecule consisting of the amino acid sequence set forth in SEQ ID NO: 84.

For example, the antibody or the antigen-binding fragment of the antibody of the present invention can be an antibody to monkey TLR7 or an antigen-binding fragment of the antibody having the properties of:
(a) specifically binding to monkey TLR7 and not binding to mouse TLR7 and/or rat TLR7; and
(b) inhibiting a function of monkey TLR7, wherein the monkey TLR7 is a molecule consisting of the amino acid sequence set forth in SEQ ID NO: 85, the mouse TLR7 is a molecule consisting of the amino acid sequence set forth in SEQ ID NO: 83, and the rat TLR7 is a molecule consisting of the amino acid sequence set forth in SEQ ID NO: 84.

Hereinafter, the anti-TLR7 antibody of the present invention and a production method thereof are described with reference to the case of anti-human TLR7 antibody as an example. Anti-monkey TLR7 antibody also can be produced in the same manner as the production method of anti-human TLR7 antibody.

The antibody to human TLR7 of the present invention can be obtained by immunizing an animal with human TLR7 or any polypeptide selected from the amino acid sequence of human TLR7, and collecting and purifying the antibody produced in vivo, using conventional methods.

Human TLR7 serving as an antigen can be obtained by expressing a human TLR7 gene in a host cell by genetic engineering. Specifically, a vector capable of expressing the TLR7 gene may be prepared and introduced into a host cell to express the gene, and the TLR7 expressed may be purified.

The antibody to human TLR7 of the present invention can be obtained also by DNA immunization. The DNA immunization is a technique to induce immunity to an antigen by transfection of an antigen-expressing plasmid into an animal individual such as a mouse or a rat, thereby allowing the individual to express the antigen.

Examples of the transfection technique include a method of directly injecting the plasmid into a muscle, a method of injecting a conjugate of the plasmid with a liposome, polyethyleneimine, or the like into a vein, a technique using viral vectors, a technique of injecting gold particles with the plasmid attached using a Gene Gun, and a hydrodynamic method of rapidly injecting a large amount of a solution of the plasmid into a vein.

For improving the expression level in the transfection method by intramuscular injection of the expression plasmid, a technique of intramuscularly injecting the plasmid and thereafter applying electroporation to the same site (Aihara H, Miyazaki J. Nat Biotechnol. 1998 September; 16(9): 867-70 or Mir L M, Bureau M F, Gehl J, Rangara R, Rouy D, Caillaud J M, Delaere P, Branellec D, Schwartz B, Scherman D. Proc Natl Acad Sci USA. 1999 Apr. 13; 96(8): 4262-7) is known as in-vivo electroporation. In this technique, the expression level is further improved by treating a muscle with hyaluronidase before intramuscular injection of the plasmid (McMahon J M, Signori E, Wells K E, Fazio V M, Wells D J. Gene Ther. 2001 August; 8(16): 1264-70).

Further, a monoclonal antibody can also be obtained, according to a known method (for example, Kohler and Milstein, Nature (1975) 256, p. 495-497, Kennet, R. ed., Monoclonal Antibodies, p. 365-367, Plenum Press, N.Y. (1980)), by fusing an antibody-producing cell which produces an antibody to TLR7 with a myeloma cell to establish a hybridoma. Specific examples of such a method include those described in International publication No. WO 09/48072 (published on Apr. 16, 2009) and International publication No. WO 10/117011 (published on Oct. 14, 2010).

Examples of the mouse anti-human TLR7 antibody established as above can include the AT01 antibody, the NB7 antibody, and the FAN2 antibody.

The amino acid sequence of the heavy-chain variable region of the AT01 antibody is set forth in SEQ ID NO: 5 in the Sequence Listing, and the polynucleotide sequence encoding the amino acid sequence is set forth in SEQ ID NO: 6 in the Sequence Listing. The amino acid sequence of the heavy-chain variable region of the NB7 antibody is set forth in SEQ ID NO: 7 in the Sequence Listing, and the polynucleotide sequence encoding the amino acid sequence is set forth in SEQ ID NO: 8 in the Sequence Listing. The amino acid sequence of the heavy-chain variable region of the FAN2 antibody is set forth in SEQ ID NO: 9 in the Sequence Listing, and the polynucleotide sequence encoding the amino acid sequence is set forth in SEQ ID NO: 10 in the Sequence Listing.

Further, the amino acid sequence of the light-chain variable region of the AT01 antibody is set forth in SEQ ID NO: 11 in the Sequence Listing, and the polynucleotide sequence encoding the amino acid sequence is set forth in SEQ ID NO: 12 in the Sequence Listing. The amino acid sequence of the light-chain variable region of the NB7 antibody is set forth in SEQ ID NO: 13 in the Sequence Listing, and the polynucleotide sequence encoding the amino acid sequence is set forth in SEQ ID NO: 14 in the Sequence Listing. The amino acid sequence of the light-chain variable region of the FAN2 antibody is set forth in SEQ ID NO: 15 in the Sequence Listing, and the polynucleotide sequence encoding the amino acid sequence is set forth in SEQ ID NO: 16 in the Sequence Listing.

The heavy-chain variable region of the AT01 antibody comprises CDRH1 consisting of the amino acid sequence set forth in SEQ ID NO: 17 (GYTFTNNWLH), CDRH2 consisting of the amino acid sequence set forth in SEQ ID NO: 18 (DIYPSNGRTN), and CDRH3 consisting of the amino acid sequence set forth in SEQ ID NO: 19 (ERGYFDY). Further, the light-chain variable region of the antibody comprises CDRL1 consisting of the amino acid sequence set forth in SEQ ID NO: 20 (KASQDINKYIA), CDRL2 consisting of the amino acid sequence set forth in SEQ ID NO: 21 (YTSTLQP), and CDRL3 consisting of the amino acid sequence set forth in SEQ ID NO: 22 (LQYDYLLT). The amino acid sequences of the aforementioned CDRs are shown also in FIG. 24-1.

The heavy-chain variable region of the NB7 antibody comprises CDRH1 consisting of the amino acid sequence set forth in SEQ ID NO: 23 (GYSITSDYAWN), CDRH2 consisting of the amino acid sequence set forth in SEQ ID NO: 24 (HISYRGNTN), and CDRH3 consisting of the amino acid sequence set forth in SEQ ID NO: 25 (WNYYGYVDYAMDY). Further, the light-chain variable region of the antibody comprises CDRL1 consisting of the amino acid sequence set forth in SEQ ID NO: 26 (RASQDISNYLN), CDRL2 consisting of the amino acid sequence set forth in SEQ ID NO: 27 (YTSRLHS), and CDRL3 consisting of the amino acid sequence set forth in SEQ ID NO: 28 (QQGDTFPT). The amino acid sequences of the aforementioned CDRs are shown also in FIG. 24-2.

The heavy-chain variable region of the FAN2 antibody comprises CDRH1 consisting of the amino acid sequence set forth in SEQ ID NO: 29 (GFSLTGYGVN), CDRH2 consisting of the amino acid sequence set forth in SEQ ID NO: 30 (MIWGDGSTD), and CDRH3 consisting of the amino acid sequence set forth in SEQ ID NO: 31 (DKGYDGYYYAMDY). Further, the light-chain variable region of the antibody comprises CDRL1 consisting of the amino acid sequence set forth in SEQ ID NO: 32 (RASENIYSYLA), CDRL2 consisting of the amino acid sequence set forth in SEQ ID NO: 33 (DAKTLAE), and CDRL3 consisting of the amino acid sequence set forth in SEQ ID NO: 34 (QHHYGIPYT). The amino acid sequences of the aforementioned CDRs are shown also in FIG. 24-3.

In one embodiment, the antibody or the antigen-binding fragment of the antibody of the present invention can have a competitive inhibitory activity for binding to the human TLR7 with an antibody comprising the amino acid sequences of the heavy-chain variable region and the light-chain variable region of the AT01 antibody, the NB7 antibody or the FAN2 antibody.

In another embodiment, the antibody or the antigen-binding fragment of the antibody of the present invention can be an antibody or an antigen-binding fragment of the antibody comprising CDRH1 to CDRH3 of the AT01 antibody as complementarity determining regions in the heavy chain and CDRL1 to CDRL3 of the AT01 antibody as complementarity determining regions in the light chain, an antibody or an antigen-binding fragment of the antibody comprising CDRH1 to CDRH3 of the NB7 antibody as complementarity determining regions in the heavy chain and CDRL1 to CDRL3 of the NB7 antibody as complementarity determining regions in the light chain, or an antibody or an antigen-binding fragment of the antibody comprising CDRH1 to CDRH3 of the FAN2 antibody as complementarity determining regions in the heavy chain and CDRL1 to CDRL3 of the FAN2 antibody as complementarity determining regions in the light chain. In a preferred aspect, the antibody or the antigen-binding fragment of the antibody of the present invention can be an antibody or an antigen-binding fragment of the antibody comprising CDRH1 to CDRH3 of the AT01 antibody as complementarity determining regions in the heavy chain and CDRL1 to CDRL3 of the AT01 antibody as complementarity determining regions in the light chain.

In still another embodiment, the antibody or the antigen-binding fragment of the antibody of the present invention can be an antibody comprising the sequences of the heavy-chain variable region and the light-chain variable region of the AT01 antibody, the NB7 antibody or the FAN2 antibody.

The antibody of the present invention includes recombinant antibodies artificially modified for the purpose of reducing the heteroantigenicity to humans and the like, such as chimeric antibodies, humanized antibodies, and human antibodies, in addition to the aforementioned monoclonal antibodies to human TLR7. These antibodies can be produced using known methods.

Examples of the chimeric antibodies can include an antibody in which the variable region and the constant region of the antibody are heterogeneous to each other, such as a chimeric antibody with a variable region of a mouse- or rat-derived antibody joined to a human-derived constant region (see Proc. Natl. Acad. Sci. U.S.A, 81, 6851-6855, (1984)). Examples of the mouse anti-human TLR7 antibody (AT01 antibody)-derived chimeric antibody can include an antibody consisting of a heavy chain comprising a heavy-chain variable region consisting of the amino acid sequence of SEQ ID NO: 5 and a light chain comprising a light-chain variable region consisting of the amino acid sequence of SEQ ID NO: 11. Examples of the AT01 antibody-derived chimeric antibody can include an antibody consisting of a heavy chain consisting of the amino acid sequence at positions 20 to 465 in SEQ ID NO: 35 and a light chain consisting of an amino acid sequence at positions 21 to 233 in SEQ ID NO: 36. In this description, such an antibody is referred to as "cAT01" or "cAT01 antibody".

Further, examples of the mouse anti-human TLR7 antibody (NB7 antibody)-derived chimeric antibody can include an antibody consisting of a heavy chain comprising a heavy-chain variable region consisting of the amino acid sequence of SEQ ID NO: 7 and a light chain comprising a light-chain variable region consisting of the amino acid sequence of SEQ ID NO: 13. Examples of the NB7 antibody-derived chimeric antibody can include an antibody consisting of a heavy chain consisting of an amino acid sequence at positions 20 to 471 in SEQ ID NO: 37 and a light chain consisting of an amino acid sequence at positions 21 to 233 in SEQ ID NO: 38. In this description, such an antibody is referred to as "cNB7" or "cNB7 antibody".

Further, examples of the mouse anti-human TLR7 antibody (FAN2 antibody)-derived chimeric antibody can include an antibody consisting of a heavy chain comprising a heavy-chain variable region consisting of the amino acid sequence of SEQ ID NO: 9 and a light chain comprising a light-chain variable region consisting of the amino acid sequence of SEQ ID NO: 15. Examples of the FAN2 antibody-derived chimeric antibody can include an antibody consisting of a heavy chain consisting of an amino acid sequence at positions 20 to 470 in SEQ ID NO: 39 and a light chain consisting of an amino acid sequence at positions 21 to 234 in SEQ ID NO: 40. In this description, such an antibody is referred to as "cFAN2" or "cFAN2 antibody".

Humanized antibodies that are recombinant antibodies can be produced by artificially modifying the sequences of the aforementioned chimeric antibodies to human TLR7 for the purpose of reducing the heteroantigenicity to humans and the like. Further, the antibody of the present invention includes antibodies with modified CDRs of the humanized antibodies. These antibodies can be produced using known methods.

Examples of the humanized antibodies can include an antibody with only the CDRs integrated into a human-derived antibody (see Nature (1986) 321, p. 522-525), and an antibody with not only the sequences of CDRs but also the amino acid residues of some parts of the framework grafted into a human antibody (International publication No. WO 90/07861).

For example, humanized antibodies derived from the cAT01 antibody and the cNB7 antibody retain all of the 6 CDR sequences derived from cAT01 or cNB7 and have the activity of inhibiting a function of human TLR7.

Suitable cases of the aforementioned humanized antibodies can include cAT01 antibody-derived humanized antibodies (huAT01 antibodies) such as: an antibody consisting of a heavy chain comprising a heavy-chain variable region consisting of the amino acid sequence set forth in SEQ ID NO: 41 and a light chain comprising a light-chain variable region consisting of the amino acid sequence set forth in SEQ ID NO: 43; an antibody consisting of a heavy chain comprising a heavy-chain variable region consisting of the amino acid sequence set forth in SEQ ID NO: 41 and a light chain comprising a light-chain variable region consisting of the amino acid sequence set forth in SEQ ID NO: 44; an antibody consisting of a heavy chain comprising a heavy-chain variable region consisting of the amino acid sequence set forth in SEQ ID NO: 42 and a light chain comprising a light-chain variable region consisting of the amino acid sequence set forth in SEQ ID NO: 43; and an antibody consisting of a heavy chain comprising a heavy-chain variable region consisting of the amino acid sequence set forth in SEQ ID NO: 42 and a light chain comprising a light-chain variable region consisting of the amino acid sequence set forth in SEQ ID NO: 44.

Further, an antibody having an activity equivalent to the aforementioned huAT01 antibodies can be selected by combining sequences exhibiting high homology with the amino acid sequence of the heavy-chain variable region and the amino acid sequence of the light-chain variable region of the aforementioned huAT01 antibodies respectively. The homology is generally a homology of 80% or more, preferably a homology of 90% or more, more preferably a homology of 95% or more, most preferably a homology of 99% or more (however, the CDRs are the same as in the aforementioned antibodies). Further, an antibody having an activity equivalent to the aforementioned antibodies can also be selected by combining an amino acid sequence with one to several (for example, 2, 3, 4, 5, 6, 7, 8, 9, or 10) amino acid residues substituted, deleted, or added in the amino acid sequence of the heavy-chain variable region or the light-chain variable region (however, excluding the CDR sites).

Further suitable cases can include: an antibody consisting of a heavy chain consisting of the amino acid sequence at positions 20 to 465 in the amino acid sequence set forth in SEQ ID NO: 45 and a light chain consisting of the amino acid sequence at positions 21 to 233 in the amino acid sequence set forth in SEQ ID NO: 48; an antibody consisting of a heavy chain consisting of the amino acid sequence at positions 20 to 465 in the amino acid sequence set forth in SEQ ID NO: 45 and a light chain consisting of the amino acid sequence at positions 21 to 233 in the amino acid sequence set forth in SEQ ID NO: 49; an antibody consisting of a heavy chain consisting of the amino acid sequence at positions 20 to 465 in the amino acid sequence set forth in SEQ ID NO: 46 and a light chain consisting of the amino acid sequence at positions 21 to 233 in the amino acid sequence set forth in SEQ ID NO: 48; an antibody consisting of a heavy chain consisting of the amino acid sequence at positions 20 to 465 in the amino acid sequence set forth in SEQ ID NO: 46 and a light chain consisting of the amino acid sequence at positions 21 to 233 in the amino acid sequence set forth in SEQ ID NO: 49; an antibody consisting of a heavy chain consisting of the amino acid sequence at positions 20 to 462 in the amino acid sequence set forth in SEQ ID NO: 47 and a light chain consisting of the amino acid sequence at positions 21 to 233 in the amino acid sequence set forth in SEQ ID NO: 48; or an antibody consisting of a heavy chain consisting of the amino acid sequence at positions 20 to 462 in the amino acid sequence set forth in SEQ ID NO: 47 and a light chain consisting of the amino acid sequence at positions 21 to 233 in the amino acid sequence set forth in SEQ ID NO: 49.

Further, examples of the cNB7 antibody-derived humanized antibody (huNB7 antibody) can include an antibody consisting of a heavy chain comprising a heavy-chain variable region consisting of the amino acid sequence of SEQ ID NO: 50 and a light chain comprising a light-chain variable region consisting of the amino acid sequence of SEQ ID NO: 51.

Further, an antibody having an activity equivalent to the aforementioned huNB7 antibody can be selected by combining sequences exhibiting high homology with the amino acid sequence of the heavy-chain variable region and the amino acid sequence of the light-chain variable region of the aforementioned huNB7 antibody. The homology is generally a homology of 80% or more, preferably a homology of 90% or more, more preferably a homology of 95% or more, most preferably a homology of 99% or more (however, the CDRs are the same as in the aforementioned antibodies). Further, an antibody having an activity equivalent to the aforementioned antibody can also be selected by combining an amino acid sequence with one to several (for example, 2, 3, 4, 5, 6, 7, 8, 9, or 10) amino acid residues substituted, deleted, or added in the amino acid sequence of the heavy-chain variable region or the light-chain variable region (however, excluding the CDR sites).

Further suitable cases can include: an antibody consisting of a heavy chain consisting of the amino acid sequence at positions 20 to 471 in the amino acid sequence set forth in SEQ ID NO: 52 and a light chain consisting of the amino acid sequence at positions 21 to 233 in the amino acid sequence set forth in SEQ ID NO: 53; or an antibody consisting of a heavy chain consisting of the amino acid sequence at positions 20 to 468 in the amino acid sequence set forth in SEQ ID NO: 54 and a light chain consisting of the amino acid sequence at positions 21 to 233 in the amino acid sequence set forth in SEQ ID NO: 53.

The antibody of the present invention may be obtained by introducing further mutation into the aforementioned humanized antibodies to change the binding ability with respect to human TLR7. Such a technique is called affinity maturation, and specific examples thereof can include the ribosome display method. The ribosome display method is a method of isolating a gene sequence of a protein which binds to a target molecule, using a tripartite complex in which the protein and mRNA carrying the genetic information of the protein are bound together via ribosomes (Stafford R L. et. al. Protein Eng. Des. Sel. 2014 (4): 97-109).

In order to avoid injuring normal human TLR7-expressing cells, the antibody desirably has low effector activity. The effector activity is known to differ depending on the subclass of the antibody. For example, a feature of IgG4 is that it has low ADCC and CDC activities, and a feature of IgG2 is that it has CDC activity while having low ADCC activity. Based on such features, an antibody with reduced ADCC and CDC activities can be produced by substituting the constant region of IgG1 with the constant region of IgG2 or IgG4. Further, an IgG1 antibody with reduced ADCC and CDC activities can be produced by partially substituting the sequence of the constant region of IgG1 with reference to IgG2 or IgG4. As an example, Marjan Hezareh et. al. Journal of Virology, 75 (24): 12161-12168 (2001) shows that the ADCC and CDC activities are reduced by substituting leucine residues 234 and 235 (the numerals represent EU indices by Kabat et. al.) of IgG1 respectively with alanine residues.

The present invention includes modified forms of the antibody or the antigen-binding fragment of the antibody. The modified forms mean those formed by chemically or biologically modifying the antibody or the antigen-binding fragment of the antibody of the present invention. The chemically modified forms include chemically modified forms of carbohydrate chains by attachment of a chemical moiety to the amino acid backbone, N-linkage, or O-linkage. The biologically modified forms include those modified after translation (for example, by glycosylation to N-linkage or O-linkage, N-terminal or C-terminal processing, deamidation, isomerization of aspartic acid, and oxidation of methionine), and those with a methionine residue added at the N-terminal by expression using prokaryote host cells. Further, the meaning of the modified products also includes those labeled for enabling detection or isolation of the antibody of the present invention or antigen, such as enzyme-labeled bodies, fluorescence-labeled bodies, and affinity-labeled bodies. Such modified products of the antibody or the antigen-binding fragment of the antibody of the present invention are useful for improving the stability and the blood retention of the original antibody of the present invention, reducing the antigenicity, and detecting or isolating the antibody or antigen.

It is known that a lysine residue at the carboxyl terminus of the heavy chain of antibodies produced in cultured mammalian cells is deleted (Journal of Chromatography A, 705: 129-134 (1995)). Further, it is also known that two amino acid residues, glycine and lysine, at the carboxyl terminus of the same heavy chain are deleted, and a proline residue newly located at the carboxyl terminus is amidated (Analytical Biochemistry, 360: 75-83 (2007)).

However, such deletions and modifications of the heavy-chain sequence have no influence on the antigen-binding ability and the effector functions (such as complement activation and antibody-dependent cellular cytotoxicity) of the antibody.

Accordingly, examples of modified forms of the antibody and the antigen-binding fragment of the antibody of the present invention can include: deletion variants with one or two amino acids deleted at the carboxyl terminus of the heavy chain; and amidated deletion variants (such as a heavy chain with an amidated proline residue at the carboxyl terminal part). However, the deletion variants at the carboxyl terminus of the heavy chain of the antibody according to the present invention are not limited to the aforementioned types, as long as the antigen-binding ability and the effector functions are maintained.

Two heavy chains constituting the antibody according to the present invention may be a combination of any one or two types of heavy chains selected from the group consisting of the full length and the aforementioned deletion variants. The quantitative ratio of the deletion variants can be affected by the type of cultured mammalian cells and culture conditions for producing the antibody according to the present invention, but examples of the main component of the antibody according to the present invention can include a component with one amino acid residue deleted at the carboxyl terminus in each of the two heavy chains. That is, heavy chains consisting of amino acid sequences with one or two amino acids deleted at the carboxyl terminus of each heavy-chain sequence represented by an amino acid sequence at positions 20 to 465 in SEQ ID NO: 35, an amino acid sequence at positions 20 to 471 in SEQ ID NO: 37, an amino acid sequence at positions 20 to 470 in SEQ ID NO: 39, an amino acid sequence at positions 20 to 465 in SEQ ID NO: 45, an amino acid sequence at positions 20 to 465 in SEQ ID NO: 46, an amino acid sequence at positions 20 to 462 in SEQ ID NO: 47, an amino acid sequence at positions 20 to 471 in SEQ ID NO: 52, and an amino acid sequence at positions 20 to 468 in SEQ ID NO: 54, in the Sequence Listing can also be used for the antibody of the present invention.

The antibodies obtained by the aforementioned methods are evaluated for their binding property with respect to an antigen, so that a suitable antibody can be selected therefrom. Another indicator for comparing the properties of the antibodies can be the stability of the antibodies, for example. Differential scanning calorimetry (DSC) is a method that enables quick and accurate measurement of the thermal denaturation midpoint (Tm), which is a good indicator of the relative structural stability of proteins. The differences in thermostability can be compared by measuring the Tm values using DSC and comparing the values. It is known that the storage stability of antibodies shows some correlation with the thermostability of antibodies (Lori Burton, et. al., Pharmaceutical Development and Technology (2007) 12, p. 265-273), and a suitable antibody can be selected using the thermostability as an indicator. Examples of other indicators for selecting an antibody can include high yield in a suitable host cell and low aggregability in an aqueous solution. Since the antibody, for example, with the highest yield does not necessarily show the highest thermostability, comprehensive determination needs to be made based on the aforementioned indicators to select an antibody that is most suitable for administration to humans.

Further, a method of obtaining a single-chain immunoglobulin by linking the full-length sequences of the heavy and light chains of an antibody using a suitable linker is also known (Lee, H-S, et. al., Molecular Immunology (1999) 36, p. 61-71; Schirrmann, T. et. al., mAbs (2010), 2, (1) p. 73-76). Such a single-chain immunoglobulin is dimerized and thus can maintain a structure and an activity that are similar to those of an antibody that was originally a tetramer. Further, the antibody of the present invention may be an antibody comprising a single heavy-chain variable region and no light-chain sequences. Such an antibody is called a single domain antibody (sdAb) or nanobody and is reported to be actually observed in camels or llamas and maintain antigen-binding ability (Muyldermans S. et. al., Protein Eng. (1994) 7 (9), 1129-35, Hamers-Casterman C. et. al., Nature (1993) 363 (6428) 446-8). The aforementioned antibody can also be understood to be a kind of antigen-binding fragment of the antibody of the present invention.

Further, the antibody-dependent cellular cytotoxicity can be enhanced by adjusting the glycosylation bound to the antibody of the present invention. International publication No. WO 99/54342, International publication No. WO 00/61739, International publication No. WO 02/31140, International publication No. WO 2007/133855, International publication No. WO 2013/120066, and the like are known as techniques for adjusting glycosylation of antibodies, but there is no limitation to these.

In the case of producing an antibody by isolating an antibody gene once and thereafter introducing it into a suitable host cell, a combination of such a suitable host cell and an expression vector can be used.

Specific examples of the antibody gene can include a combination of a gene encoding the heavy-chain sequence and a gene encoding the light-chain sequence of the antibodies in this specification. More specifically, examples of the antibody gene can include a combination of a polynucleotide comprising a polynucleotide sequence encoding the antibody or the antigen-binding fragment of the antibody of the present invention, a polynucleotide comprising a polynucleotide sequence encoding the amino acid sequence of the heavy-chain variable region of the antibody or the antigen-binding fragment of the antibody of the present invention, and a polynucleotide comprising a polynucleotide sequence encoding the amino acid sequence of the light-chain variable region of the antibody or the antigen-binding fragment of the antibody of the present invention. The heavy-chain sequence gene constituting the antibody gene also includes a polynucleotide comprising a polynucleotide sequence of a polynucleotide which hybridizes with a polynucleotide consisting of a polynucleotide sequence complementary to the aforementioned polynucleotide sequence encoding the heavy-chain variable region under stringent conditions. Further, the light-chain sequence gene constituting the antibody gene also includes a polynucleotide comprising a polynucleotide sequence of a polynucleotide which hybridizes with a polynucleotide consisting of a polynucleotide sequence complementary to the aforementioned polynucleotide sequence encoding the light-chain variable region under stringent conditions.

When transforming the host cell, the heavy-chain sequence gene and the light-chain sequence gene can be inserted in the same expression vector or in separate expression vectors. In the case of using a eukaryotic cell as a host cell, animal cells, plant cells, and eukaryotic microorganisms can be used. Examples of the animal cells can include (1) mammalian cells such as COS cells (Gluzman, Y. Cell (1981) 23, p. 175-182, ATCC CRL-1650) which are monkey cells, and dihydrofolate reductase enzyme-deficient strains (Urlaub, G. and Chasin, L. A. Proc. Natl. Acad. Sci. U.S.A (1980) 77, p. 4126-4220) of mouse fibroblasts NIH3T3 (ATCC No. CRL-1658) and Chinese hamster ovary cells (CHO cells, ATCC CCL-61). Further, in the case of using prokaryotic cells, examples can include *Escherichia coli* and *Bacillus subtilis*. An antibody is obtained by introducing a target antibody gene into such a cell by transformation and culturing the transformed cell in vitro. Since the yield may differ depending on the sequence of the antibody in the aforementioned culture method, those easily produced as pharmaceuticals can be selected from amongst antibodies having the same binding activity using the yield as an indicator.

There is no limitation on the isotype of the antibody of the present invention, and examples thereof can include IgG (IgG1, IgG2, IgG3, and IgG4), IgM, IgA (IgA1 and IgA2), IgD, or IgE, preferably IgG or IgM, further preferably IgG1 or IgG4.

Further, the antibody of the present invention may be an antigen-binding fragment of an antibody comprising an antigen-binding site of the antibody or a modified product thereof. A fragment of the antibody can be obtained by treating the antibody with a protease such as papain and pepsin or modifying the antibody gene with a genetically engineered technique to allow expression in a suitable cultured cell. Among such antibody fragments, fragments maintaining all or part of the functions of the full-length molecules of the antibody can be called antigen-binding fragments of the antibody.

Examples of the functions of antibodies can generally include antigen-binding activity, the activity of neutralizing antigen activity, the activity of enhancing antigen activity, antibody-dependent cytotoxicity, complement-dependent cytotoxicity, and complement-dependent cellular cytotoxicity. The function of the antigen-binding fragment of the antibody in the present invention is binding activity to human TLR7, preferably the activity of inhibiting a function of human TLR7, more preferably the activity of suppressing production of IL-6 and/or type I interferon by TLR7-expressing cells.

Examples of the fragment of the antibody can include Fab, $F(ab')_2$, Fv, or single-chain Fv (scFv) obtained by linking heavy- and light-chain Fvs with a suitable linker, diabodies, linear antibodies, and multispecific antibodies formed from antibody fragments. Further, the fragment of the antibody also includes a monovalent Fab' fragment in a variable region of the antibody obtained by treating $F(ab')_2$ under reduced conditions.

Further, the antibody of the present invention may be a multispecific antibody having specificity to at least two types of different antigens. In general, such a molecule binds to two types of antigens (that is, a bispecific antibody), but the "multispecific antibody" in the present invention includes antibodies having specificity to more (for example, three types of) antigens.

The multispecific antibody of the present invention may be an antibody consisting of the full-length or a fragment of such an antibody (for example, $F(ab')_2$ bispecific antibody). The bispecific antibody can be produced also by binding the heavy and light chains (HL pairs) of two types of antibodies to each other or producing a bispecific antibody-producing fusion cell by fusing hybridomas which produce different monoclonal antibodies (Millstein et al., Nature (1983) 305, p. 537-539).

The antibody of the present invention may also be a single-chain antibody (which may be referred to also as scFv). The single-chain antibody can be obtained by linking the heavy-chain variable region and the light-chain variable region of an antibody by a polypeptide linker (Pluckthun, The Pharmacology of Monoclonal Antibodies, 113 (edited by Rosenberg and Moore), Springer Verlag, New York, p. 269-315 (1994), Nature Biotechnology (2005), 23, p. 1126-1136). Further, a BiscFv fragment produced by binding two scFvs with a polypeptide linker can also be used as a bispecific antibody.

Methods for producing single-chain antibodies are known in this technical field (for example, see U.S. Pat. Nos. 4,946,778, 5,260,203, 5,091,513, and 5,455,030). In such a scFv, the heavy-chain variable region and the light-chain variable region are linked via a linker which does not produce conjugates, preferably a polypeptide linker (Huston, J. S. et al., Proc. Natl. Acad. Sci. U.S.A. (1988), 85, p. 5879-5883). The heavy-chain variable region and the light-chain variable region in the scFv may be derived from the same antibody or separate antibodies. Any single-chain peptide consisting of 12 to 19 residues is, for example, used as the polypeptide linker which links the variable regions.

DNA encoding the scFv is obtained by PCR amplification using a DNA element encoding the whole or a desired part of the amino acid sequence of DNA encoding the heavy chain or the heavy-chain variable region of the antibody and DNA encoding the light chain or the light-chain variable region thereof as a template and a primer pair defining both ends thereof, and further amplification by combining DNA encoding a polypeptide linker portion and a primer pair defining both ends thereof so as to be linked respectively with the heavy chain and the light chain.

Further, once DNA encoding the scFv is produced, an expression vector containing the DNA and a host cell transformed by the expression vector can be obtained according to conventional methods. Further, the scFv can be obtained using the host cell according to a conventional method. Such an antibody fragment can be produced by obtaining and expressing a gene thereof in a host cell as described above.

The antibody of the present invention may be an antibody multimerized to increase the affinity for the antigen. The antibody to be multimerized may be one antibody or a plurality of antibodies which recognize a plurality of epitopes of the same antigen. Examples of the method for multimerizing the antibody can include binding of an IgG CH3 domain to two scFvs, binding to streptavidin, and introduction of a helix-turn-helix motif.

The antibody of the present invention may be a polyclonal antibody which is a mixture of a plurality of types of anti-human TLR7 antibodies comprising different amino acid sequences. As an example of the polyclonal antibody, there is a mixture of a plurality of types of antibodies comprising different CDRs. As such a polyclonal antibody, an antibody purified from a culture obtained by culturing a mixture of cells which produce different antibodies can be used (see International publication No. WO 2004/061104).

As a modified product of the antibody, an antibody bound to various molecules such as polyethylene glycol (PEG) can also be used.

The antibody of the present invention may further be an immunoconjugate formed by such an antibody and another drug. Examples of the antibody can include the antibody bound to a radioactive substance or a compound having a pharmacological action (Nature Biotechnology (2005) 23, p. 1137-1146).

The antibody obtained can be purified to homogeneity. For separating and purifying the antibody, common separation and purification methods used for proteins may be used. For example, the antibody can be separated and purified by appropriately selecting and combining column chromatography, filter filtration, ultrafiltration, salting-out, dialysis, preparative polyacrylamide gel electrophoresis, isoelectric focusing, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but there is no limitation to these.

Examples of the chromatography can include affinity chromatography, ion exchange chromatography, hydrophobic chromatography, gel filtration chromatography, reverse-phase chromatography, and adsorption chromatography. Such chromatography can be performed using liquid chromatography such as HPLC and FPLC. Examples of the column used for the affinity chromatography can include a protein A column and a protein G column. Examples of a column which is a protein A column can include Hyper D, POROS, Sepharose F. F. (pharmacia). Further, the antibody can also be purified, using a carrier with an immobilized antigen, by utilizing the binding property to the antigen.

3. Pharmaceutical Containing Anti-Human TLR7 Antibody

Antibodies that inhibit a function of human TLR7 can be obtained from the anti-human TLR7 antibodies obtained by the methods disclosed in "2. Anti-TLR7 antibody and production thereof" above. These antibodies that inhibit a function of human TLR7 can inhibit the biological activity of human TLR7 in vivo, that is, activation of human TLR7-expressing cells typified by blood cells by human TLR7 ligands, and therefore can be used as pharmaceuticals such as agents for treating and/or preventing diseases caused by a function of human TLR7.

The diseases and conditions caused by a function of human TLR7 can include immune inflammation-related diseases, allergic diseases, infections, or cancers.

Examples of the immune inflammation-related diseases can include diseases of the connective tissue and the musculoskeletal system (such as systemic lupus erythematosus, rheumatoid arthritis, juvenile idiopathic arthritis, adult-onset Still's disease, ankylosing spondylitis, systemic scleroderma, polymyositis, dermatomyositis, psoriatic arthritis, osteoarthritis, mixed connective tissue disease, and muscular dystrophy), the blood system (such as autoimmune hemolytic anemia, aplastic anemia, and idiopathic thrombocytopenic purpura), the digestive tract system (such as Crohn's disease, ulcerative colitis, and ileitis), the hepatobiliary pancreatic system and the endocrine system (such as autoimmune hepatitis, viral hepatitis, alcoholic hepatitis, nonalcoholic steatohepatitis, primary sclerosing cholangitis, primary biliary cirrhosis, Sjogren's syndrome, type 1 diabetes, autoimmune thyroiditis, Graves' disease, and Hashimoto's thyroiditis), the respiratory system (such as chronic obstructive pulmonary disease, cystic fibrosis, and interstitial pneumonia), the cranial nervous system (such as multiple sclerosis, myasthenia gravis, meningitis, encephalomyelitis, and autoimmune encephalitis), the visual system (such as uveitis, trachoma, and endophthalmitis), the cardiovascular system (such as vasculitis syndrome, polyangiitis granulomatosis Wegener's granulomatosis, myocarditis, ischemic heart disease, and atherosclerosis), the skin epidermis system (such as psoriasis, pemphigus, vitiligo, contact dermatitis, and eczema), the renal system (such as glomerulonephritis, diabetic nephropathy, IgA nephropathy, purpura nephritis, nephrosis, and interstitial cystitis), and the endocrine system (such as type 1 diabetes, autoimmune thyroiditis, Graves' disease, and Hashimoto's thyroiditis), and systemic inflammation (such as Behcet's disease, antiphospholipid antibody syndrome, IgG4-related diseases, sepsis, hemorrhage, hypersensitivity, transplantation rejection, and shock symptoms caused by, for example, cancer chemotherapy).

Examples of the allergic diseases can include atopic dermatitis, asthma, anaphylaxis, anaphylactoid reactions, food allergy, rhinitis, otitis media, drug reactions, insect sting reactions, plant reactions, latex allergy, conjunctivitis, and urticaria.

Examples of the infections can include diseases caused by infections by viruses (such as a single-stranded RNA virus, a double-stranded RNA virus, a single-stranded DNA virus, and a double-stranded DNA virus), bacteria (such as gram-negative bacteria, gram-positive bacteria, acid-fast bacteria, actinomycetes, spirochetes, spiral bacteria, *Rickettsia, Chlamydia*, and *Mycoplasma*), fungi (such as *Trichophyton, Candida, Cryptococcus, Aspergillus, Pneumocystis*, and *Malassezia*), and parasites (such as filariae, trematodes, cestodes, Distoma, *Echinococcus, Entamoeba histolytica*, fleas, lice, mites, Ascaridida, and Oxyuridae).

Examples of the cancer treatment can include treatments for lymphoma, leukemia, breast cancer, lung cancer, and skin cancer.

Examples of the anti-human TLR7 antibodies as pharmaceuticals can include chimeric antibodies and humanized antibodies, which are produced from the AT01 antibody and/or the NB7 antibody, and CDR modified forms thereof.

The inhibitory activity against a function of human TLR7 by the anti-human TLR7 antibodies in vitro can be measured, for example, based on the activity of suppressing the activation of blood cells expressing human TLR7. For example, the activity of suppressing IL-6 release from human PBMCs by CL264 stimulation can be measured by adding each anti-human TLR7 antibody to human PBMCs at various concentrations.

It has been experimentally proved and widely recognized that, in various immune inflammation-related diseases including systemic lupus erythematosus, the ligand concentration of human TLR7 is increased, human TLR7 expression is enhanced, or human TLR7 stimulation is caused. Inflammatory responses due to inflammatory cytokines such as interleukin 6 (IL-6) produced by the action of human TLR7 ligands on human TLR7-expressing cells and release of type I interferons due to enhancement and activation of antibody production cause systemic immune inflammatory responses and cause development of, or worsen, autoimmunity such as systemic lupus erythematosus. Accordingly, suppressing the production of cytokines which depend on human TLR7 stimulation leads to prevention and treatment of systemic lupus erythematosus and the like, and the usefulness of a human TLR7 antibody as a remedy can be determined using suppression activity as an indicator.

Examples of a suitable antibody in the present invention can include an antibody or an antigen-binding fragment of the antibody which binds specifically to human TLR7 comprising the amino acid sequence set forth in SEQ ID NO: 2 or 4 and reduces the amount of IL-6 released by CL264-treated human PBMCs in a concentration dependent manner.

Further, the treatment or prevention effects by the anti-human TLR7 antibody on various diseases can be checked based on an in-vivo evaluation system or ex-vivo evaluation system by administration of the anti-human TLR7 antibody to monkeys cross-reactive with the antibody, or also based on the following in-vivo evaluation system by administration of the anti-human TLR7 antibody to human TLR7 transgenic and mouse TLR7 knockout mice.

The effects on inflammatory cytokine production are evaluated by comparing the ability to produce cytokine in the peripheral blood between the anti-TLR7 antibody group and the non-administration group, in inflammation induced by intraperitoneally or intravenously administering TLR7 ligands to mice.

The effects on atopic dermatitis are evaluated by quantifying the behavior caused by atopic dermatitis spontaneously developed or induced by a method such as repeatedly applying a mite antigen cream to the auricle or the back 3 to 6 times every 3 days to 2 weeks, applying haptens to the auricle, the abdomen, or the back daily to once a week, administering a pruritus inducer intradermally in the auricle, subcutaneously in the back, or intrathecally, or using NC/Nga mice which are spontaneous atopic mice, through measurement of the frequency of pruritus using magnets mounted on both insteps of mice and a pruritus behavior measuring device, or inspection of the pathological features of the skin, the peripheral blood, the spinal cord tissue, and the like, and comparing the results between the anti-human TLR7 antibody group and the non-administration group.

The effects on psoriasis are evaluated by quantifying psoriasiform dermatitis induced by a method such as applying Imiquimod or R848 to the auricle and the back after shaving, administering cytokines such as IL-23 to mice intradermally in the auricle, through such as measurement of the weight and the thickness of the inflammation site or the myeloperoxidase activity of neutrophils infiltrating the site, flow cytometry analysis of the infiltrated cells, gene analysis, or measurement of the cytokine concentration, and comparing the results between the anti-TLR7 antibody group and the non-administration group.

The effects on arthritis are evaluated by inducing arthritis by a method such as administering an emulsion obtained by mixing a bovine type II collagen solution and a complete Freund's adjuvant intradermally to the tail base of mice and thereafter administering an emulsion obtained by mixing a bovine type II collagen solution and an incomplete Freund's adjuvant 2 to 3 weeks later, or administering an anti-bovine type II collagen antibody and TLR ligands, and comparing the scoring of subsequent joint swelling, measurement of the thickness of the footpad, the concentrations of antibodies, cytokines or blood biomarkers in the blood or tissues, or the proliferative activity, the ability to produce cytokine or the surface antigens of the cells obtained from the peripheral blood, the spleen, the lymph nodes, the bone marrow, the joint sites, or the like, between the anti-human TLR7 antibody group and the non-administration group.

The effects on colitis are evaluated by inducing colitis by a method such as administering trinitrobenzene sulfonic acid into the intestine of mice fasted for 24 hours, allowing ad libitum access to a 1 to 10% dextran sodium sulfate aqueous solution from a supply bottle for 4 days to 2 weeks, or transferring CD4+CD25-CD45RBhi T cells collected from the lymph nodes and the spleen of human TLR7 transgenic mice after purification intraperitoneally to Rag2-deficient mice, and comparing the body weight during the observation period, the thickening degree, the number and size of polyps, and the histopathological features of the intestine by autopsy after the completion of the test, the concentrations of antibodies, cytokines or blood biomarkers in the blood or tissues, the proliferative activity, the ability to produce cytokine or the surface antigens of the cells obtained from the intestine, the peripheral blood, the thymus, the spleen, the lymph nodes, the bone marrow, or Peyer's patches, or the like, between the anti-human TLR7 antibody group and the non-administration group.

The effects on systemic lupus erythematosus are evaluated by comparing between the anti-human TLR7 antibody group and the non-administration group: the concentrations of antibodies, cytokines or blood biomarkers in the blood or tissues collected from NZB/WF1 mice, MRL/lpr mice and BXSB mice which are spontaneous models over time, the antibody titer or the biomarker concentration in their urine, or a symptom induced by transferring cells prepared from an organ such as the spleen and the lymph nodes collected after the completion of the above test to untreated mice, or the like.

The effects on hepatitis are evaluated by inducing hepatitis by a method such as administering D-galactosamine alone or in combination with lipopolysaccharide intraperitoneally to mice and administering concanavalin A alone into the tail vein, and comparing the AST and ALT concentrations in the blood collected 1 hour to 1 week after administering an inflammatory substance, the cytokine concentration, and the histopathological condition of liver lesions, between the anti-human TLR7 antibody group and the non-administration group.

The thus obtained antibody that inhibits the biological activity of human TLR7 is useful as a pharmaceutical, particularly, as an antibody for preventing or treating immune inflammation-related diseases including systemic lupus erythematosus, allergic diseases, infections, or cancers.

As one example, the anti-human TLR7 antibody can be administered alone or in combination with at least one other therapeutic agent, for treating or preventing immune inflammation-related diseases, allergic diseases, infections, or cancers. Examples of the other therapeutic agent which can be administered in combination with the anti-human TLR7 antibody can include corticosteroids, non-steroidal anti-inflammatory drugs, nucleic acid antimetabolites, nucleic acid synthesis inhibitors, antifolates, calcineurin inhibitors, anti-malarial drugs, antithymocyte globulins, biologics targeting cell surface antigens, or biologics targeting cytokine interferons or cytokine interferon receptors, but there is no limitation to these examples.

Specific examples of the therapeutic agent can include Methylprednisolone as a corticosteroid, Loxoprofen Sodium Hydrate, Diclofenac sodium, Indomethacin, and Acetyl salicylic acid as non-steroidal anti-inflammatory drugs, Mycophenolate mofetil as a nucleic acid antimetabolite, Cyclophosphamide as a nucleic acid synthesis inhibitor, Cyclosporin and Taclorims as calcineurin inhibitors, Hydroxychloroquine as an anti-malarial drug, Methotrexate as an antifolate, Zetbulin, Lymphoglobuline, and Thymoglobulin as antithymocyte globulins, Alemtuzumab, Rituximab, and Abatacept as biologics targeting cell surface antigens, and Infliximab, Etanercept, Adalimumab, Tocilizumab, Belimumab and Anifrolumab as biologics targeting cytokine interferons or cytokine interferon receptors.

Depending on the condition of immune inflammation-related diseases, allergic diseases, infections or cancers and the degree of treatment and/or prevention targeted, two, three or more types of other therapeutic agents can also be administered, and the other therapeutic agents can be encapsulated in the same preparation so as to be administered at the same time. The other therapeutic agents and the anti-human TLR7 antibody can also be encapsulated in the same preparation so as to be administered at the same time. Further, the anti-human TLR7 antibody and the other therapeutic agents can also be encapsulated in separate preparations and administered at the same time. Further, the other therapeutic agents and the anti-human TLR7 antibody can also be administered separately one after another. That is, a therapeutic agent containing the anti-human TLR7 antibody or the antigen-binding fragment of the antibody as an active ingredient may be administered after the other therapeutic agents are administered, or the other therapeutic agents may be administered after a therapeutic agent containing the anti-human TLR7 antibody or the antigen-binding fragment of the antibody as an active ingredient is administered. In the case of administration in gene therapy, the gene of a protein therapeutic agent and the gene of the anti-human TLR7 antibody can be inserted downstream of the same or separate promoter regions and can be introduced into the same or separate vectors.

The targeted drug conjugates disclosed in M. C. Garnet "Targeted drug conjugates: principles and progress", Advanced Drug Delivery Reviews, (2001) 53, 171-216 can be produced by binding the therapeutic agents to the anti-human TLR7 antibody or its fragment. For this purpose, any antibody fragment can be applied, other than antibody molecules, as long as it does not completely lose T-cell recognition. Examples thereof can include fragments such as Fab, $F(ab')_2$, and Fv, and the antibody and such fragments can be used in the same manner as in the present invention. The binding mode of the anti-human TLR7 antibody, or the fragment of the antibody, to the therapeutic agents can be in various forms disclosed in M. C. Garnet "Targeted drug conjugates: principles and progress", Advanced Drug Delivery Reviews, (2001) 53, 171-216, G. T. Hermanson "Bioconjugate Techniques" Academic Press, California (1996), Putnam and J. Kopecek "Polymer Conjugates with Anticancer Activity" Advances in Polymer Science (1995) 122, 55-123, etc. That is, examples thereof can include a mode in which the anti-human TLR7 antibody is chemically bound to the therapeutic agents directly or via a spacer such as an oligopeptide, or bound via a suitable drug carrier. Examples of the drug carrier can include liposomes and water-soluble polymers. More specifically, examples of the mode of binding via such a drug carrier can include a mode in which the antibody and the therapeutic agents are included in a liposome, and the liposome is bound to the antibody, and a mode in which the therapeutic agents are chemically bound to a water-soluble polymer (compound with a molecular weight of about 1000 to 100000) directly or via a spacer such as an oligopeptide, and the antibody is bound to the water-soluble polymer. The antibody (or the fragment) can be bound to the therapeutic agents or the drug carriers such as liposomes and water-soluble polymers by a method known to those skilled in the art such as the method according to G. T. Hermanson "Bioconjugate Techniques" Academic Press, California (1996), Putnam and J. Kopecek "Polymer Conjugates with Anticancer Activity" Advances in Polymer Science (1995) 122, 55-123. The therapeutic agents can be included in the liposome by a method known to those skilled in the art such as the method according to D. D. Lasic "Liposomes: From Physics to Applications", Elsevier Science Publishers B. V., Amsterdam (1993). The therapeutic agents can be bound to the water-soluble polymer by a method known to those skilled in the art such as the method according to D. Putnam and J Kopecek "Polymer Conjugates with Anticancer Activity" Advances in Polymer Science (1995) 122, 55-123. The conjugates of the antibody (or the fragment) and a protein therapeutic agent (or the fragment) can be produced by a genetic engineering method known to those skilled in the art other than the aforementioned method.

The present invention also provides a pharmaceutical composition comprising an expression vector which comprises a polynucleotide comprising a polynucleotide sequence encoding at least one or those of the anti-human TLR7 antibody or the antigen-binding fragment of the antibody, as an active ingredient in an amount effective for treating and/or preventing disease, and a diluent, a carrier, a solubilizer, an emulsifier, a preservative and/or an additive, which are pharmaceutically acceptable.

The present invention also provides a pharmaceutical composition comprising an expression vector which comprises a polynucleotide comprising a polynucleotide sequence encoding at least one or those of the anti-human TLR7 antibody or the antigen-binding fragment of the antibody, in an amount effective for treating and/or preventing disease, at least one therapeutic agent in an amount effective for treating and/or preventing disease, and a diluent, a carrier, a solubilizer, an emulsifier, a preservative, and/or an additive, which are pharmaceutically acceptable.

Examples of the therapeutic agent can include antifolates, calcineurin inhibitors, corticosteroids, antithymocyte globulins, nucleic acid antimetabolites, nucleic acid synthesis inhibitors, biologics targeting cell surface antigens, or biologics targeting cytokines or cytokine receptors described above, but there is no limitation to these examples.

The substances used for preparations which are acceptable in the pharmaceutical composition of the present invention are preferably non-toxic, preferably at the administration dosage and the administration concentration, to a person to whom the pharmaceutical composition is administered.

The pharmaceutical composition of the present invention can contain substances used for preparations for changing or maintaining the pH, the osmotic pressure, the viscosity, the transparency, the color, the isotonicity, the sterility, the stability, the dissolution rate, the sustained release rate, the absorption rate and the penetration rate. Examples of the substances used for preparations can include, but are not limited to: amino acids such as glycine, alanine, glutamine, asparagine, arginine or lysine, antibacterial agents, antioxidants such as ascorbic acid, sodium sulfate or sodium bisulfite, buffers such as phosphoric acid, citric acid, boric acid buffer, sodium bicarbonate or a tris-hydrochloric acid (Tris-Hcl) solution, fillers such as mannitol or glycine, chelating agents such as ethylenediaminetetraacetic acid (EDTA), complexing agents such as caffeine, polyvinyl pyrrolidine, β-cyclodextrin, or hydroxypropyl-β-cyclodextrin, extenders such as glucose, mannose or dextrin, other carbohydrates such as monosaccharides or disaccharides, coloring agents, flavoring agents, diluents, emulsifiers, hydrophilic polymers such as polyvinyl pyrrolidine, preservatives such as low-molecular weight polypeptides, salt-forming counterions, benzalkonium chloride, benzoic acid, salicylic acid, thimerosal, phenethyl alcohol, methylparaben, propylparaben, chlorhexidine, sorbic acid or hydrogen peroxide, solvents such as glycerin, propylene glycol or polyethylene glycol, sugar alcohols such as mannitol or sorbitol, suspending agents, polysorbates such as sorbitan ester, polysorbate 20 or polysorbate 80, surfactants such as triton, tromethamine, lecithin or cholesterol, stability enhancers such as sucrose or sorbitol, elasticity enhancers such as sodium chloride, potassium chloride, mannitol or sorbitol, transport agents, excipients, and/or pharmaceutical auxiliary agents. The amount of the substances used for preparations is to be added at preferably 0.01 to 100 times, particularly 0.1 to 10 times, with respect to the weight of the anti-human TLR7 antibody. The suitable composition of the pharmaceutical composition in preparations can be appropriately determined by those skilled in the art, corresponding to the disease to be applied, the administration route to be applied, or the like.

Excipients or carriers in the pharmaceutical composition may be liquid or solid. Suitable excipients or carriers may be water for injection, normal saline, artificial cerebrospinal fluid, or other substances generally used for parenteral administration. Neutral normal saline or normal saline containing serum albumin can also be used for carriers. The pharmaceutical composition can contain a Tris buffer with a pH of 7.0 to 8.5, an acetate buffer with a pH of 4.0 to 5.5 or a citric acid buffer with a pH of 3.0 to 6.2. Further, these buffers can also contain sorbitol or other compounds. Examples of the pharmaceutical composition of the present invention can include a pharmaceutical composition comprising anti-human TLR7 antibody and a pharmaceutical composition comprising anti-human TLR7 antibody and at least one therapeutic agent, and the pharmaceutical composition of the present invention is prepared as a drug having a selected composition and a necessary purity, in the form of a freeze-dried product or liquid. A pharmaceutical composition comprising anti-human TLR7 antibody and a pharmaceutical composition comprising anti-human TLR7 antibody and at least one bone metabolism disorder therapeutic drug can be formed as a freeze-dried product using a suitable excipient such as sucrose.

The pharmaceutical composition of the present invention can be prepared for parenteral administration or can be prepared for oral gastrointestinal absorption. The composition and the concentration of the preparation can be determined depending on the administration method. Alternatively, an affinity that is a higher affinity (lower Kd value), in terms of the dissociation constant (Kd value) to human TLR7 of the anti-human TLR7 antibodies contained in the pharmaceutical composition of the present invention, enables the drug efficacy to be exerted with reduced dosage in humans, and therefore the dosage of the pharmaceutical composition of the present invention in humans can also be determined based on this affinity. The dosage in the present invention may be about 0.1 to 100 mg/kg once every 1 to 180 days when the anti-human TLR7 antibody is administered to a human.

Examples of embodiments of the pharmaceutical composition of the present invention can include injections including intravenous drip, suppositories, nasal preparations, sublingual preparations and transdermal drugs.

Although most approved antibody preparations are intravenously administered, subcutaneous administration is preferred in many medical settings. In such a case, the volume is limited to 1.0 to 1.5 mL, and thus a high-concentration antibody solution is required depending on the dosage. However, when the concentration is increased, the viscosity of the drug solution increases, and therefore the injection may be impossible due to the high viscosity with the thickness of commonly used injection needles. That is, in the case of selecting an injection, the property of low viscosity has an important meaning to be prioritized as an embodiment of the pharmaceutical composition, and a suitable antibody can be selected using the viscosity as an indicator.

EXAMPLES

Hereinafter, the present invention will be specifically described by way of examples, but the present invention is not limited to these examples. In the following examples, each operation related to genetic engineering is performed according to the method disclosed in "Molecular Cloning" (Sambrook, J., Fritsch, E. F. and Maniatis, T., Cold Spring Harbor Laboratory Press, 1989) or performed using a commercially available reagent or kit according to the instruction of the commercially available product, unless otherwise specified.

Example 1

Production of Mouse Anti-Human TLR7 Antibody

1)-1 Immunization

1)-1-1 Establishment of Ba/F3 Cell Line Expressing Human TLR7-Flag-His×6/Human Unc93B1-HAX2

The human TLR7 (variant 2) gene (SEQ ID NO: 3) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing human TLR7-Flag-His×6.

The human TLR7 encoded by the human TLR7 (variant 2) gene (SEQ ID NO: 3) comprises the amino acid sequence of SEQ ID NO: 4. The sequence is shown in FIG. 2.

The human Unc93B1 gene (SEQ ID NO: 55) was integrated into retroviral vectors, pMXs (Cell Biolabs, Inc.) tagged with HAX2 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to the Ba/F3 cell line expressing human TLR7-Flag-His×6 established above, and high-speed centrifugation was performed at 2000 rpm for 1 hour, to establish a Ba/F3 cell line expressing human TLR7-Flag-His×6/human Unc93B1-HAx2.

1)-1-2 Mouse Immunization

The Ba/F3 cell line expressing human TLR7-Flag-His×6/human Unc93B1-HAX2 established above in 1)-1-1 was mixed with an adjuvant, TITERMAX® Gold (TiterMax USA, Inc.), and the mixture was administered as an antigen to the sole, the tail base, and the peritoneal cavity of TLR9-deficient mice with BALB/c background produced by the Institute of Medical Science of the University of Tokyo a total of 3 times per week.

At the 4th time, the Ba/F3 cell line expressing human TLR7-Flag-His×6/human Unc93B1-HAX2 suspended in 1×PBS was intraperitoneally administered.

The spleen was removed 5 days after the last immunization and used for producing hybridomas.

1)-2 Production of Hybridomas

The spleen cells after the immunization were mixed with Sp2/o cell line (ATCC), and cell fusion was performed using an HVJ-E cell fusion kit (ISHIHARA SANGYO KAISHA, LTD). In order to select hybridomas, the cells were cultured from the day after the cell fusion operation in RPMI1640 (Life Technologies) containing a HAT (Thermo Fisher Scientific)-containing culture solution (10% FBS), 50-μM 2-Mercaptoethanol (Life Technologies), 50-U/mL Penicillin, and 50-μg/mL Streptomycin (Life Technologies), and the hybridoma colonies that emerged were collected to produce monoclonal hybridomas.

1)-3 Screening of Antibody Binding to Human TLR7 by Flow Cytometry

The culture supernatant was collected from hybridomas forming colonies under a microscope and used for screening. A Ba/F3 cell line expressing hTLR7-Flag-His×6/hUnc93B1-HAX2 subjected to membrane permeation with 0.1% Saponin (Sigma-Aldrich Co. LLC) and Ba/F3 cells expressing nothing were each stained with the culture supernatant and analyzed by flow cytometry (LSRFortessaTMX-20, Becton, Dickinson and Company), to select hybridomas producing anti-hTLR7 antibody.

1)-4 Screening of Human TLR7 Antibody Inhibition of Human TLR7 Function by Flow Cytometry The human TLR7 (variant 2) gene (SEQ ID NO: 3) and the human Unc93B1 D34A mutant-HAX2 gene (SEQ ID NO: 86) were introduced into a Ba/F3 cell line (RIKEN, BRC) using a retrovirus. Further, a NF-κB-green fluorescence protein (GFP) reporter plasmid (STRATAGENE) was transfected into the cells by the electroporation method, so that a Ba/F3 cell line expressing hTLR7/hUnc93B1 D34A mutant-HAX2 and capable of analyzing NF-κB activation was established, and the hybridoma culture supernatant was added to the cell line. The cells were stimulated 4 hours later with 25 ng/ml of a TLR7 ligand, R848 (InvivoGen). As a result of analyzing the inhibitory effects of human TLR7 response by measuring the GFP fluorescence intensity using flow cytometry 24 hours later, three mouse anti-human TLR7 antibody-producing hybridomas were selected and were named AT01, NB7, and FAN2, respectively.

In this description, antibodies produced by hybridomas AT01, NB7, and FAN2 are referred to as AT01 antibody, NB7 antibody, and FAN2 antibody, respectively.

1)-5 Determination of Isotype of Antibody

The isotypes of the antibodies produced by the mouse anti-human TLR7 antibody-producing hybridomas (AT01, NB7, and FAN2) obtained in 1)-4 were each determined using an IsoStrip Mouse Monoclonal Antibody Isotyping Kit (Merck KGaA). As a result, the isotypes of AT01 antibody, NB7 antibody, and FAN2 antibody were each determined to be an IgG1/κ chain.

1)-6 Preparation of Mouse Anti-Human TLR7 Antibody

The mouse anti-human TLR7 monoclonal antibody was purified from ascites collected about 10 days after each hybridoma was intraperitoneally administered to ICR-CD1-Foxnl nude mice (ICR-nu, CHARLES RIVER LABORATORIES JAPAN, INC.) pretreated with pristane (Sigma-Aldrich Co. LLC., currently, Merck KGaA).

First, pristane was intraperitoneally administered to ICR-nu, and the mice were bred for 7 days or more. Thereafter, the AT01, NB7, or FAN2-producing hybridoma was cultured in RPMI1640 (Life Technologies) containing 10% FBS, 50-μM 2-Mercaptoethanol (Life Technologies), 50-U/mL Penicillin, and 50-μg/mL Streptomycin (Life Technologies), followed by proliferation to a sufficient volume. Thereafter, the hybridoma was suspended in 1×PBS and intraperitoneally administered to the ICR-nu.

Ascites was collected 10 days later, and the blood cells were sedimented by a high-speed centrifuge, to collect a supernatant. After 10-fold dilution with 1×PBS, the ascites was passed through a 0.45 μm filter (Millipore).

The antibody was purified from the aforementioned ascites on a proteinG column (GE Healthcare Japan Corporation) using an AKTAprime plus (GE Healthcare Japan Corporation).

Subsequently, buffer replacement with saline was performed together with enrichment using PD-10 (GE Healthcare Japan Corporation), to prepare the antibody at a concentration of 1.0 mg/mL or more.

Finally, sterilization with Millex-GV 0.22 μm (Millipore) was performed, to give a purified sample.

Example 2

In Vitro Evaluation of Mouse Anti-Human TLR7 Antibody

2)-1 Evaluation of Binding Selectivity of Mouse Anti-Human TLR7 Antibody

2)-1-1 Establishment of Ba/F3 Cell Line Expressing Mouse TLR7-Flag-His×6

The mouse TLR7 gene (SEQ ID NO: 56) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing mouse TLR7-Flag-His×6.

The mouse TLR7 encoded by the mouse TLR7 gene (SEQ ID NO: 56) comprises the amino acid sequence of SEQ ID NO: 83. The sequence is shown in FIG. 3.

2)-1-2 Establishment of Ba/F3 Cell Line Expressing Rat TLR7-Flag-His×6

The rat TLR7 gene (SEQ ID NO: 57) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to establish a Ba/F3 cell line expressing rat TLR7-Flag-His×6.

The rat TLR7 encoded by the rat TLR7 gene (SEQ ID NO: 57) comprises the amino acid sequence of SEQ ID NO: 84. The sequence is shown in FIG. 4.

2)-1-3 Establishment of Ba/F3 Cell Line Expressing Monkey TLR7-Flag-His×6

The monkey TLR7 gene (SEQ ID NO: 58) was integrated into retroviral vectors, pMXs (Cell Biolabs, Inc.) tagged with Flag-His×6 added to the C-terminus of the gene using an enzyme, IN FUSION® (Takara Bio Inc). The retroviral vectors were transfected into a packaging cell line based on the HEK293 cell line, Plat-E (Cell Biolabs, Inc.) using a transfection reagent, FUGENE® 6 (Roche). The culture supernatant was collected 24 hours later and used as a virus suspension. The virus suspension was mixed with a transfection reagent, DOTAP (Roche), the mixture was added to a Ba/F3 cell line (RIKEN, BRC), and high-speed centrifugation was performed at 2000 rpm for 1 hour, to construct a Ba/F3 cell line expressing monkey TLR7-Flag-His×6.

The monkey TLR7 encoded by the monkey TLR7 gene (SEQ ID NO: 58) comprises the amino acid sequence of SEQ ID NO: 85. The sequence is shown in FIG. 5.

2)-1-4 Evaluation of Binding Selectivity of Mouse Anti-Human TLR7 Antibody by Flow Cytometry The Ba/F3 cell line expressing human TLR7-Flag-His×6/human Unc93B1-HAX2 established above in 1)-1-1, the Ba/F3 cell line expressing mouse TLR7-Flag-His×6 established above in 2)-1-1, the Ba/F3 cell line expressing rat TLR7-Flag-His×6×2 established above in 2)-1-2, and the Ba/F3 cell line expressing monkey TLR7-Flag-His×6 established above in 2)-1-3 were subjected to membrane permeation with 0.1% Saponin and stained using AT01 antibody, NB7 antibody, and FAN2 antibody, and a secondary antibody, Goat anti-mouse IgG (H+L)-PE (eBioscience). The binding selectivity of each antibody was evaluated by comparing the average fluorescence intensity (MFI) based on flow cytometry analysis.

The results indicate that AT01 antibody, NB7 antibody, and FAN2 antibody specifically bound to human TLR7 or monkey TLR7 and did not bind to mouse TLR7 or rat TLR7.

2)-2 Evaluation of Binding Ability of Mouse Anti-Human TLR7 Antibody

The Ba/F3 cell line expressing human TLR7-Flag-His×6/human Unc93B1-HAx2 established above in 1)-1-1 was subjected to membrane permeation with 0.1% Saponin and stained using a dilution series of AT01 antibody, NB7 antibody, and FAN2 antibody, and a secondary antibody, Goat anti-mouse IgG (H+L)-PE (eBioscience). The binding activity of each antibody was evaluated by comparing the mean fluorescence intensity (MFI) based on flow cytometry analysis.

The results indicate that the antibody having the highest binding activity was in the order of AT01 antibody, NB7 antibody, and FAN2 antibody.

2)-3 Inhibitory Activity of Mouse Anti-Human TLR7 Antibody on Cytokine Production Human PBMCs were purchased from Cellular Technology Limited as a frozen product and thawed according to the instructions for use.

The PBMCs suspended at a concentration of $2.5\times10^6$ cells/mL in RPMI1640 (Life Technologies Corp.) containing 10% FBS, 1-mM Sodium Pyruvate (Life Technologies Corp.), 0.1-mM MEM Non-Essential Amino Acids (Life Technologies Corp.), 50-μM 2-Mercaptoethanol (Life Technologies Corp.), 50-U/mL Penicillin, and 50-μg/mL Streptomycin (Life Technologies Corp.) were seeded in a 96-well cell culture plate at 100 μL each, and the mouse anti-human TLR7 antibody, AT01 antibody, NB7 antibody, or FAN2 antibody, or a mouse IgG control antibody (BioLegend, Inc.) was added thereto at 80 μL/well, followed by pretreatment in an incubator at 37° C. for 4 hours.

Thereafter, 1-mg/mL CL-264 (InvivoGen) was added thereto at 20 μL/well, and the mixture was stirred well, followed by culturing at 37° C. for about 20 hours under 5% $CO_2$. The plate was stirred well and thereafter centrifuged at 1500 rpm for 5 minutes, and the concentration of interleukin-6 (IL-6) contained in the supernatant was measured by the FRET method (Cisbio Bioassay. Inc).

FIG. 6 shows the results. The mouse anti-human TLR7 antibody suppressed the production of IL-6 from the human PBMCs treated with CL-264 in a concentration dependent manner. The AT01 antibody, NB7 antibody, and FAN2 antibody inhibited the production of IL-6 from the human PBMCs in a concentration dependent manner. The half-inhibitory concentrations (IC50 of AT01 antibody, NB7 antibody and FAN2 antibody were 192 ng/mL, 771 ng/mL, and 8389 ng/mL, respectively, which were calculated from the concentrations of the two values, which are either side of the 50% inhibitory activity, and the inhibitory activity when each of the two concentrations were added.

Meanwhile, inhibition was not observed in the mouse IgG control antibody even at a concentration of 10 μg/mL.

Example 3

Determination of Nucleotide Sequence and Amino Acid Sequence of cDNA Encoding Variable Region of Mouse Anti-Human TLR7 Antibody 3)-1 Synthesis of cDNA Total RNA was collected from the hybridomas of AT01, NB7, and FAN2 using a TRIzol Reagent (Ambion). Subsequently, cDNA was synthesized using a PrimeScript 1st Strand cDNA Synthesis Kit (TAKARA).

3)-2 Amplification and Sequencing of Mouse Immunoglobulin Heavy- and Light-Chain Variable Region Gene Fragments The nucleotide sequences encoding the variable regions of the antibody contained in the synthesized cDNA were determined by GenScript Corporation.

3)-2-1 Mouse Anti-Human TLR7 Antibody (AT01)

The amino acid sequence encoded by the nucleotide sequence of cDNA encoding the heavy-chain variable region of AT01 antibody determined above is set forth in SEQ ID NO: 5 in the Sequence Listing.

The amino acid sequence encoded by the nucleotide sequence of cDNA encoding the light-chain variable region of AT01 antibody determined above is set forth in SEQ ID NO: 11 in the Sequence Listing.

3)-2-2 Mouse Anti-Human TLR7 Antibody (NB7)

The amino acid sequence encoded by the nucleotide sequence of cDNA encoding the heavy-chain variable region of NB7 antibody determined above is set forth in SEQ ID NO: 7 in the Sequence Listing.

The amino acid sequence encoded by the nucleotide sequence of cDNA encoding the light-chain variable region of NB7 antibody determined above is set forth in SEQ ID NO: 13 in the Sequence Listing.

3)-2-3 Mouse Anti-Human TLR7 Antibody (FAN2)

The amino acid sequence encoded by the nucleotide sequence of cDNA encoding the heavy-chain variable region of FAN2 antibody determined above is set forth in SEQ ID NO: 9 in the Sequence Listing.

The amino acid sequence encoded by the nucleotide sequence of cDNA encoding the light-chain variable region of FAN2 antibody determined above is set forth in SEQ ID NO: 15 in the Sequence Listing.

Example 4

Production of Chimeric Anti-Human TLR7 Antibody

4)-1 Construction of Expression Vector of Chimeric Anti-TLR7 Antibody

4)-1-1 Construction of Chimeric Light-Chain Expression Vector, pCMA-LK

A DNA fragment (SEQ ID NO: 59) containing an approximately 5.4-kb fragment obtained by digesting plasmid pcDNA3.3-TOPO/LacZ (Invitrogen Corp.) with restriction enzymes, XbaI and PmeI and a DNA sequence encoding the human light-chain signal sequence and the human kappa-chain constant region were bound together using an In-Fusion HD PCR cloning kit (Clontech Laboratories, Inc.), to produce pcDNA3.3/LK. pCMA-LK was constructed by removing the neomycin expression unit from pcDNA3.3/LK.

4)-1-2 Construction of Chimeric IgG1 Heavy-Chain Expression Vector, pCMA-G1

A DNA fragment (SEQ ID NO: 60) containing a DNA fragment obtained by digesting pCMA-LK with XbaI and PmeI and removing the light chain signal sequence and the human kappa-chain constant region was bound to a DNA sequence encoding the human heavy-chain signal sequence and the human IgG1 constant region using an In-Fusion HD PCR cloning kit (Clontech Laboratories, Inc.), to construct pCMA-G1.

4)-1-3 Construction of AT01 Chimeric Anti-Human TLR7 Antibody Expression Vector

A DNA fragment comprising the nucleotide sequence encoding the heavy-chain variable region of cAT01 antibody represented by nucleotides 36 to 422 in the nucleotide sequence set forth in SEQ ID NO: 61 was synthesized (Geneart AG). The synthesized DNA fragment was inserted into the site where pCMA-G1 was cut with a restriction enzyme, BlpI, using an In-Fusion HD PCR cloning kit (Clontech Laboratories, Inc.), thereby constructing a cAT01 antibody heavy-chain expression vector. The heavy chain of cAT01 antibody comprises the amino acid sequence of SEQ ID NO: 35 including the signal sequence. The sequence is shown in FIG. 7.

The DNA fragment (SEQ ID NO: 62) comprising a DNA sequence encoding the light chain of cAT01 antibody was synthesized (Geneart AG). Using the pCMA-LK produced in Example 4)-1-1, a cAT01 antibody light-chain expression vector was constructed in the same manner as above. The light chain of cAT01 antibody comprises the amino acid sequence of SEQ ID NO: 36 including the signal sequence. The sequence is shown in FIG. 7.

4)-1-4 Construction of NB7 Chimeric Anti-Human TLR7 Antibody Expression Vector

A DNA fragment comprising the nucleotide sequence encoding the heavy-chain variable region of cNB7 antibody represented by nucleotides 36 to 440 in the nucleotide sequence set forth in SEQ ID NO: 63 was synthesized (Geneart AG). A cNB7 heavy-chain expression vector was constructed in the same manner as in Example 4)-1-3. The heavy chain of cNB7 antibody comprises the amino acid sequence of SEQ ID NO: 37 including the signal sequence. The sequence is shown in FIG. 8.

A DNA fragment (SEQ ID NO: 64) comprising the DNA sequence encoding the cNB7 light chain was synthesized (Geneart AG). Using the pCMA-LK produced in Example 4)-1-1, a cNB7 light-chain expression vector was constructed in the same manner as in Example 4)-1-3. The light chain of cNB7 antibody comprises the amino acid sequence of SEQ ID NO: 38 including the signal sequence. The sequence is shown in FIG. 8.

4)-1-5 Construction of FAN2 Chimeric Anti-Human TLR7 Antibody Expression Vector

A DNA fragment comprising the nucleotide sequence encoding the heavy-chain variable region of cFAN2 antibody represented by nucleotides 36 to 437 in the nucleotide sequence set forth in SEQ ID NO: 65 was synthesized (Geneart AG). A cFAN2 heavy-chain expression vector was constructed in the same manner as in Example 4)-1-3. The heavy chain of cFAN2 antibody comprises the amino acid sequence of SEQ ID NO: 39 including the signal sequence. The sequence is shown in FIG. 9.

A DNA fragment (SEQ ID NO: 66) comprising the DNA sequence encoding the cFAN2 light chain was synthesized (Geneart AG). Using the pCMA-LK produced in Example 4)-1-1, a cFAN2 light-chain expression vector was constructed in the same manner as in Example 4)-1-3. The light chain of cFAN2 antibody comprises the amino acid sequence of SEQ ID NO: 40 including the signal sequence. The sequence is shown in FIG. 9.

4)-2 Production of Chimeric Anti-Human TLR7 Antibody

4)-2-1 Production of Chimeric AT01 Antibody

FreeStyle 293F cells (Invitrogen Corp.) were passaged and cultured according to the manual. $1.2\times10^9$ FreeStyle 293F cells (Invitrogen Corp.) in the logarithmic growth phase were seeded in a 3-L Fernbach Erlenmeyer Flask (Corning Incorporated) and diluted with a FreeStyle293 expression medium (Invitrogen Corp.) at a concentration of to $2.0\times10^6$ cell/mL. 0.24 mg of the heavy-chain expression vector constructed above in 4)-1-3, 0.36 mg of the light-chain expression vector constructed above in 4)-1-3, and 1.8 mg of Polyethyleneimine (Polyscience #24765) were added to 40 mL of an Opti-Pro SFM medium (Invitrogen Corp.), followed by gentle stirring and further standing for 5 minutes. Thereafter, the mixture was added to the FreeStyle 293F cells. After shaking culture in an incubator at 37° C. under 8% $CO_2$ for 4 hours at 90 rpm, 600 ml of EX-CELL VPRO medium (SAFC Biosciences), 18 ml of GlutaMAX I (Gibco), and 30 mL of Yeastolate Ultrafiltrate (Gibco) were added thereto, followed by shaking culture in an incubator at 37° C. under 8% $CO_2$ at 90 rpm for 7 days, and the culture supernatant obtained was filtered with a Disposable Capsule Filter (Advantec #CCS-045-E1H), to produce a chimeric AT01 antibody.

4)-2-2 Production of Chimeric NB7 Antibody

Using the heavy-chain expression vector and light-chain expression vector constructed in 4)-1-4 above, a chimeric NB7 antibody was produced by the method of 4)-2-1.

4)-2-3 Production of Chimeric FAN2 Antibody

Using the heavy-chain expression vector and light-chain expression vector constructed in 4)-1-5 above, a chimeric FAN2 antibody was produced by the method of 4)-2-1.

4)-3 Purification of Chimeric Anti-Human TLR7 Antibody

An antibody of interest was purified from each culture supernatant obtained in Example 4)-2 by a one-step process of rProtein A affinity chromatography. The culture supernatant was applied to a column (GE Healthcare Bioscience) filled with MabSelectSuRe equilibrated with PBS, and thereafter the column was washed with PBS in a volume of twice or more the column volume. Next, elution was carried out with a 2M arginine hydrochloride solution (pH 4.0), to collect a fraction containing the antibody. The fraction was subjected to buffer replacement with PBS(−) by dialysis (Slide-A-Lyzer Dialysis Cassette, Thermo Scientific). The antibody was concentrated with a Centrifugal UF Filter Device, VIVASPIN20 (fraction molecular weight UF10K, Sartorius AG), to prepare the IgG at a concentration of 10 mg/mL or more. Finally, filtration was carried out with a Minisart-Plus filter (Sartorius AG), to give a purified sample.

Example 5

In Vitro Activity of Chimeric Anti-Human TLR7 Antibody

5)-1 Antigen-Binding Activity of Chimeric Anti-Human TLR7 Antibody by Flow Cytometry A Ba/F3 cell line expressing human TLR7-Flag-His×6/hUnc93B1-HA×2 was subjected to membrane permeation with 0.1% Saponin and stained using the dilution series of chimeric AT01 antibody, NB7 antibody, and FAN2 antibody at the antibody concentrations obtained in Example 4, and the secondary antibody, Goat anti-human IgG Fc-PE (eBioscience). The binding activity of each antibody was evaluated by comparing the MFI based on flow cytometry analysis. The results indicate that the antibody having the highest binding activity was in the order of chimeric AT01 antibody (cAT01), chimeric NB7 antibody (cNB7), and chimeric FAN2 antibody (cFAN2).

5)-2 Inhibitory Activity of Chimeric Anti-Human TLR7 Antibody on Cytokine Production Human PBMCs were purchased from Cellular Technology Limited as a frozen product and thawed according to the instructions for use. The PBMCs suspended at a concentration of $2.5\times10^6$ cells/mL in RPMI1640 (Life Technologies Corp.) containing 10% FBS, 1 mM Sodium Pyruvate (Life Technologies Corp.), 0.1-mM MEM Non-Essential Amino Acids (Life Technologies Corp.), 50 μM 2-Mercaptoethanol (Life Technologies Corp.), 50 U/mL Penicillin, and 50 μg/mL Streptomycin (Life Technologies Corp.) were seeded in a 96-well cell culture plate at 100 μL each, and the chimeric anti-human TLR7 antibody, cAT01, cNB7, or cFAN2, or a human IgG control antibody (Eureka Therapeutics) was added thereto at 80 μL/well, followed by pretreatment in an incubator at 37° C. for 4 hours. Thereafter, 1-mg/mL CL-264 (InvivoGen) was added thereto at 20 μL/well, and the mixture was stirred well, followed by culturing at 37° C. for about 20 hours under 5% $CO_2$. The plate was stirred well and thereafter centrifuged at 1500 rpm for 5 minutes, and the concentration of IL-6 contained in the supernatant was measured by the FRET method (Cisbio Bioassay. Inc).

Figure 10:
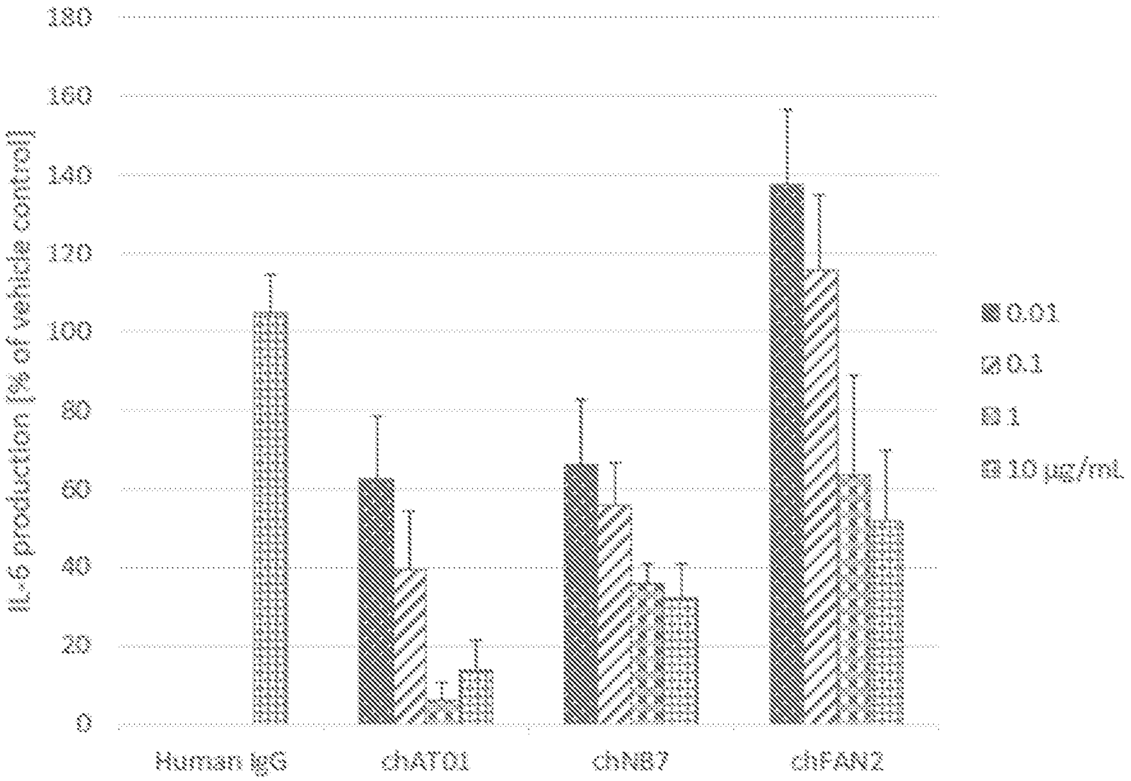
FIG. 10 is a graph showing that cAT01, cNB7, and cFAN2, which are chimeric anti-human TLR7 antibodies, suppress the production of IL-6 from human PBMCs treated with CL-264 in a concentration dependent manner.

FIG. 10 shows that the chimeric anti-human TLR7 antibody suppresses the production of IL-6 from the human PBMCs treated with CL-264 depending in a concentration dependent manner. The antibodies cAT01, cNB7, and cFAN2 inhibited the production of IL-6 from the human PBMCs depending on the concentration added. The half-inhibitory concentrations (IC50) of the antibodies cAT01, cNB7 and cFAN2 were 35 ng/mL, 196 ng/mL, 10000 ng/mL or more, respectively, which were calculated from the concentrations of the two values, which are either side of the 50% inhibitory activity, and the inhibitory activity when each of the two concentrations were added.

Meanwhile, inhibition was not observed in the human IgG control antibody even at a concentration of 10 μg/mL.

Example 6

Production of Humanized Anti-Human TLR7 Antibody

6)-1 Humanized Design of Anti-Human TLR7 Antibody

6)-1-1 Molecular Modeling of Antibody Variable Regions

The molecular modeling of the variable regions was performed by a method known as homology modeling (Methods in Enzymology, 203, 121-153, (1991)) using a commercially available protein three-dimensional structure analysis program, BioLuminate (Schrodinger K.K). The template used was a structure registered in the Protein Data Bank (Nuc. Acid Res. 35, D301-D303 (2007)) having high sequence identity to the variable regions of the heavy and light chains.

6)-1-2 Design of Humanized Amino Acid Sequence

A technique known as CDR grafting (Proc. Natl. Acad. Sci. USA 86, 10029-10033(1989)) was used for humanization. Acceptors having high identity were selected from the consensus sequences defined in Kabat et al. (Sequences of Proteins of Immunological Interest, 5th Ed. Public Health Service National Institutes of Health, Bethesda, Md. (1991)) and the human germline sequences registered in IMGT® (THE INTERNATIONAL IMMUNOGENETICS INFORMATION SYSTEM, www.imgt.org), and donor residues to be transferred onto the acceptors were selected by analyzing the three-dimensional models with reference to the standards given by Queen et al. (Proc. Natl. Acad. Sci. USA 86, 10029-10033 (1989)).

6)-1-3 Design of Humanized Amino Acid Sequence of AT01 Antibody

The consensus sequences of human gamma-chain subgroup 1 and kappa-chain subgroup 1 having high identity to the framework regions of cAT01 were selected as the acceptors of cAT01. In the molecular modeling of the variable regions, a known structure (PDB ID: 1E4W) was used as a template.

6)-1-3-1 Humanization of AT01 Antibody Heavy Chain (1) The heavy chain designed was named huAT01_H1_IgG1LALA. huAT01_H1_IgG1LALA comprises the amino acid sequence set forth in SEQ ID NO: 45 including the signal sequence as a heavy-chain full-length amino acid sequence. The sequence is shown in FIG. 11. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 45 comprises the sequence set forth in SEQ ID NO: 67. Further, the nucleotide sequence encoding the heavy-chain variable region comprises the sequence set forth in SEQ ID NO: 77.

(2) The heavy chain designed was named huAT01_H3_IgG1LALA. huAT01_H3_IgG1LALA including the signal sequence as a heavy-chain full-length amino acid sequence comprises the amino acid sequence set forth in SEQ ID NO: 46. The sequence is shown in FIG. 12. In the sequence, the amino acid sequence at positions 1 to 19 is the signal sequence, the amino acid sequence at positions 20 to 135 is the variable region, and the amino acid sequence at positions 136 to 465 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 46 comprises the sequence set forth in SEQ ID NO: 68. Further, the nucleotide sequence encoding the heavy-chain variable region comprises the sequence set forth in SEQ ID NO: 78.

(3) The heavy chain designed was named huAT01_H3_IgG4Pro. huAT01_H3_IgG4Pro including the signal sequence as a heavy-chain full-length amino acid sequence comprises the amino acid sequence set forth in SEQ ID NO: 47. The sequence is shown in FIG. 13. In the sequence, the amino acid sequence at positions 1 to 19 is the signal sequence, the amino acid sequence at positions 20 to 135 is the variable region, and the amino acid sequence at positions 136 to 462 is the constant region. Further, the amino acid sequence at positions 45 to 54 is CDRH1, the amino acid sequence at positions 69 to 78 is CDRH2, and the amino acid sequence at positions 118 to 124 is CDRH3.

The nucleotide sequence encoding the amino acid sequence of SEQ ID NO: 47 comprises the sequence set forth in SEQ ID NO: 69. Further, the nucleotide sequence encoding the heavy-chain variable region comprises the sequence set forth in SEQ ID NO: 78.

FIG. 14 shows the comparison of the amino acid sequence (SEQ ID NO: 5) of the variable region of cAT01_H which is the heavy chain of chimeric antibody cAT01 (which will be hereinafter referred to as cAT01_H), the amino acid sequence (SEQ ID NO: 41) of the variable region of the humanized antibody heavy chain, huAT01_H1_IgG1LALA (which will be hereinafter referred to as huAT01_H1), and the amino acid sequence (SEQ ID NO: 42) of the variable region of huAT01_H3_IgG1LALA (which will be hereinafter referred to as huAT01_H3). In the sequences of huAT01_H1 and huAT01_H3, the symbol "•" represents the same amino acid residue as that of cAT01_H, and a substituted amino acid residue is shown in the site where the amino acid residue is described.

6)-1-3-2 Humanization of AT01 Antibody Light Chain

The light chain designed was named huAT01_L1. huAT01_L1 comprises the amino acid sequence set forth in SEQ ID NO: 48 including the signal sequence as a light-chain full-length amino acid sequence. The sequence is shown in FIG. 15. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 48 comprises the sequence set forth in SEQ ID NO: 70. Further, the nucleotide sequence encoding the light-chain variable region comprises the sequence set forth in SEQ ID NO: 79.

The light chain designed was named huAT01_L2. huAT01_L2 comprises the amino acid sequence set forth in SEQ ID NO: 49 including the signal sequence as a light-chain full-length amino acid sequence. The sequence is shown in FIG. 16. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 49 is set forth in SEQ ID NO: 71. Further, the nucleotide sequence encoding the light-chain variable region comprises the sequence set forth in SEQ ID NO: 80.

FIG. 17 shows the comparison of the amino acid sequence (SEQ ID NO: 11) of the variable region of cAT01_L, which is the light chain of chimeric antibody cAT01 (which will be hereinafter referred to as cAT01_L), the amino acid sequence (SEQ ID NO: 43) of the variable region of humanized antibody light chain huAT01_L1 (which will be hereinafter referred to as huAT01_L1), and the amino acid sequence (SEQ ID NO: 44) of the variable region of huAT01_L2 (which will be hereinafter referred to as huAT01_L2). In the sequences of huAT01_L1 and huAT01_L2, the symbol "•" represents the same amino acid residue as that of cAT01_L, and a substituted amino acid residue is shown in the site where the amino acid residue is described.

6)-1-4 Design of Humanized Amino Acid Sequence of NB7

Human germline sequences IGHV4-30-4*02 and IGHJ6*01 having high identity to the framework regions of cNB7 were selected as the acceptors of cNB7. In the molecular modeling of the variable regions, a known structure (PDB ID: 3CDF) was used as a template.

6)-1-4-1 Humanization of NB7 Antibody Heavy Chain (1) The heavy chain designed was named huNB7_H3_IgG1LALA. huNB7_H3_IgG1LALA comprises the amino acid sequence set forth in SEQ ID NO: 52 including the signal sequence as a heavy-chain full-length amino acid sequence. The sequence is shown in FIG. 18. In the sequence, the amino acid sequence at positions 1 to 19 is the signal sequence, the amino acid sequence at positions 20 to 141 is the variable region, and the amino acid sequence at positions 142 to 471 is the constant region. Further, the amino acid sequence at positions 45 to 55 is CDRH1, the amino acid sequence at positions 70 to 78 is CDRH2, the amino acid sequence at positions 118 to 130 is CDRH3.

The nucleotide sequence encoding the amino acid sequence of SEQ ID NO: 52 is set forth in SEQ ID NO: 72. Further, the nucleotide sequence encoding the heavy-chain variable region comprises the sequence set forth in SEQ ID NO: 81.

(2) The heavy chain designed was named huNB7_H3_IgG4Pro. huNB7_H3_IgG4Pro comprises the amino acid sequence set forth in SEQ ID NO: 54 including the signal sequence as a heavy-chain full-length amino acid sequence. The sequence is shown in FIG. 19. In the sequence, the amino acid sequence at positions 1 to 19 is the signal sequence, the amino acid sequence at positions 20 to 141 is the variable region, and the amino acid sequence at positions 142 to 468 is the constant region. Further, the amino acid sequence at positions 45 to 55 is CDRH1, the amino acid sequence at positions 70 to 78 is CDRH2, the amino acid sequence at positions 118 to 130 is CDRH3.

The nucleotide sequence encoding the amino acid sequence of SEQ ID NO: 54 is set forth in SEQ ID NO: 73. Further, the nucleotide sequence encoding the heavy-chain variable region comprises the sequence set forth in SEQ ID NO: 81.

FIG. 20 shows the comparison of the amino acid sequence (SEQ ID NO: 7) of the variable region of cNB7_H, which is the heavy chain of chimeric antibody cNB7 (which will be hereinafter referred to as cNB7_H) and the amino acid sequence (SEQ ID NO: 50) of the variable region of humanized antibody heavy chain huNB7_H3_IgG1LALA (which will be hereinafter referred to as huNB7_H3). In huNB7_H3, the symbol "•" represents the same amino acid residue as that of cNB7_H, and a substituted amino acid residue is shown in the site where the amino acid residue is described.

6)-1-4-2 Humanization of NB7 Antibody Light Chain

The light chain designed was named huNB7_L3. huNB7_L3 comprises the amino acid sequence set forth in SEQ ID NO: 53 including the signal sequence as a light-chain full-length amino acid sequence. The sequence is shown in FIG. 21. In the sequence, the amino acid sequence at positions 1 to 20 is the signal sequence, the amino acid sequence at positions 21 to 126 is the variable region, and the amino acid sequence at positions 127 to 233 is the constant region. Further, the amino acid sequence at positions 44 to 54 is CDRL1, the amino acid sequence at positions 70 to 76 is CDRL2, and the amino acid sequence at positions 109 to 116 is CDRL3.

The nucleotide sequence encoding the amino acid sequence of SEQ ID NO: 53 is set forth in SEQ ID NO: 74. Further, the nucleotide sequence encoding the light-chain variable region comprises the sequence set forth in SEQ ID NO: 82.

FIG. 22 shows the comparison of the amino acid sequence (SEQ ID NO: 13) of the variable region of cNB7_L, which is the light chain of chimeric antibody cNB7 (which will be hereinafter referred to as cNB7_L) and the amino acid sequence (SEQ ID NO: 51) of the variable region of humanized antibody light chain huNB7_L3 (which will be hereinafter referred to as huNB7_L3). In huNB7_L3, the symbol "•" represents the same amino acid residue as that of cNB7_L, and a substituted amino acid residue is shown in the site where the amino acid residue is described.

6)-2 Design of Humanized Antibody by Combining Heavy and Light Chains

6)-2-1 Design of Humanized AT01 Anti-TLR7 Antibody (1) An antibody comprising huAT01_H1_IgG1LALA consisting of the amino acid sequence at positions 20 to 465 in SEQ ID NO: 45 as the heavy chain and huAT01_L1 consisting of the amino acid sequence at positions 21 to 233 in SEQ ID NO: 48 as the light chain was named "huAT01_H1L1_IgG1LALA antibody" or "huAT01_H1L1_IgG1LALA".

(2) An antibody comprising huAT01_H3_IgG1LALA consisting of the amino acid sequence at positions 20 to 465 in SEQ ID NO: 46 as the heavy chain and huAT01_L1 consisting of the amino acid sequence at positions 21 to 233 in SEQ ID NO: 48 as the light chain was named "huAT01_H3L1_IgG1LALA antibody" or "huAT01_H3L1_IgG1LALA".

(3) An antibody comprising huAT01_H3_IgG1LALA consisting of the amino acid sequence at positions 20 to 465 in SEQ ID NO: 46 as the heavy chain and huAT01_L2 consisting of the amino acid sequence at positions 21 to 233 in SEQ ID NO: 49 as the light chain was named "huAT01_H3L2_IgG1LALA antibody" or "huAT01_H3L2_IgG1LALA".

(4) An antibody comprising huAT01_H3_IgG4Pro consisting of the amino acid sequence at positions 20 to 462 in SEQ ID NO: 47 as the heavy chain and huAT01_L2 consisting of the amino acid sequence at positions 21 to 233 in SEQ ID NO: 49 as the light chain was named "huAT01_H3L2_IgG4Pro antibody" or "huAT01_H3L2_IgG4Pro".

6)-2-2 Design of Humanized NB7 Anti-TLR7 Antibody (1) An antibody consisting of huNB7_H3_IgG1LALA consisting of the amino acid sequence at positions 20 to 471 in SEQ ID NO: 52 as the heavy chain and huNB7_L3 consisting of the amino acid sequence at positions 21 to 233 in SEQ ID NO: 53 as the light chain was named "huNB7_H3L3_IgG1LALA antibody" or "huNB7_H3L3_IgG1LALA".

(2) An antibody consisting of huNB7_H3_IgG4Pro consisting of the amino acid sequence at positions 20 to 468 in SEQ ID NO: 54 as the heavy chain and huNB7_L3 consisting of the amino acid sequence at positions 21 to 233 in SEQ ID NO: 53 as the light chain was named "huNB7_H3L3_IgG4Pro antibody" or "huNB7_H3L3_IgG4Pro".

6)-3 Production of Humanized Anti-Human TLR7 Antibody

6)-3-1 Construction of Humanized IgG1LALA Type Heavy-Chain Expression Vector, pCMA-G1LALA pCMA-G1LALA was constructed in the same manner as in Example 4)-1-2 using DNA fragments comprising the nucleotide sequences encoding the amino acid sequences of the human heavy-chain signal sequence and the human IgG1LALA constant region (SEQ ID NO: 75).

6)-3-2 Construction of Humanized IgG4Pro Type Heavy-Chain Expression Vector, pCMA-G4Pro pCMA-G4Pro was constructed in the same manner as in Example 4)-1-2 using DNA fragments comprising the nucleotide sequences encoding the amino acid sequences of the human heavy-chain signal sequence and the human IgG4Pro constant region (SEQ ID NO: 76).

6)-3-3 Construction of AT01 Humanized Heavy-Chain Expression Vector

6)-3-3-1 Construction of huAT01_H1_IgG1LALA Expression Vector

A DNA fragment represented by nucleotides 36 to 422 in the nucleotide sequence of huAT01_H1_IgG1LALA set forth in SEQ ID NO: 46 was synthesized (Geneart AG). The DNA fragment synthesized was inserted into the site where pCMA-G1LALA was cut with a restriction enzyme, BlpI, using an In-Fusion HD PCR cloning kit (Clontech Laboratories, Inc.), thereby constructing a huAT01_H1_IgG1LALA expression vector.

6)-3-3-2 Construction of huAT01_H3_IgG1LALA Expression Vector

A DNA fragment represented by nucleotides 36 to 422 in the nucleotide sequence of huAT01_H3_IgG1LALA set forth in SEQ ID NO: 68 was synthesized (Geneart AG). A huAT01_H3_IgG1LALA expression vector was constructed in the same manner as in Example 6)-3-3-1.

6)-3-3-3 Construction of huAT01_H3_IgG4Pro Expression Vector

A DNA fragment represented by nucleotides 36 to 422 in the nucleotide sequence of huAT01_H3_IgG4Pro set forth in SEQ ID NO: 69 was synthesized (Geneart AG). The DNA fragment synthesized was inserted into the site where pCMA-G4Pro was cut with a restriction enzyme, BlpI, using an In-Fusion HD PCR cloning kit (Clontech Laboratories, Inc.), thereby constructing a huAT01_H3_IgG4Pro expression vector.

6)-3-4 Construction of AT01 Humanized Light-Chain Expression Vector

6)-3-4-1 Construction of huAT01_L1 Expression Vector

A DNA fragment represented by nucleotides 37 to 399 in the nucleotide sequence of huAT01_L1 set forth in SEQ ID NO: 70 was synthesized (Geneart AG). The DNA fragment synthesized was inserted into the site where pCMA-LK was cut with a restriction enzyme, BsiWI, using an In-Fusion HD PCR cloning kit (Clontech Laboratories, Inc.), thereby constructing a huAT01_L1 expression vector.

6)-3-4-2 Construction of huAT01_L2 Expression Vector

A DNA fragment represented by nucleotides 37 to 399 in the nucleotide sequence of huAT01_L2 set forth in SEQ ID NO: 71 was synthesized (Geneart AG). A huAT01_L1 expression vector was constructed in the same manner as in Example 6)-3-4-1 using an In-Fusion HD PCR cloning kit (Clontech Laboratories, Inc).

6)-3-5 Construction of NB7 Humanized Heavy-Chain Expression Vector

6)-3-5-1 Construction of huNB7_H3_IgG1LALA Expression Vector

A DNA fragment represented by nucleotides 36 to 440 in the nucleotide sequence of huNB7_H3_IgG1LALA set forth in SEQ ID NO: 72 was synthesized (Geneart AG). A huNB7_H3_IgG1LALA expression vector was constructed in the same manner as in Example 6)-3-3-1.

6)-3-5-2 Construction of huNB7_H3_IgG4Pro Expression Vector

A DNA fragment represented by nucleotides 36 to 440 in the nucleotide sequence of huNB7_H3_IgG4Pro set forth in SEQ ID NO: 73 was synthesized (Geneart AG). A huNB7_H3_IgG4Pro expression vector was constructed in the same manner as in Example 6)-3-3-3.

6)-3-6 Construction of NB7 Humanized Light-Chain Expression Vector

6)-3-6-1 Construction of huNB7_L3 Expression Vector

A DNA fragment represented by nucleotides 37 to 399 in the nucleotide sequence of huNB7_L3 set forth in SEQ ID NO: 74 was synthesized (Geneart AG). A huNB7_L3 expression vector was constructed in the same manner as in Example 6)-3-4-1 using an In-Fusion HD PCR cloning kit (Clontech Laboratories, Inc).

6)-3-7 Preparation of Humanized Antibodies

6)-3-7-1 Production of Humanized Antibodies

Humanized antibodies of huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro were produced by the combination of the heavy and light chains designed in Example 6)-2, using the expression vectors constructed in Examples 6)-3-1 to 6)-3-6, in the same manner as in Example 4)-2.

6)-3-7-2 Purification of Humanized Antibodies

The culture supernatant obtained in Example 6)-3-7-1 was purified by a two-step process of rProtein A affinity chromatography and ceramic hydroxyapatite.

The culture supernatant was applied to a column (GE Healthcare Bioscience) filled with MabSelectSuRe equilibrated with PBS, and thereafter the column was washed with PBS in a volume of twice or more the column volume. Next, each antibody was eluted with a 2M arginine hydrochloride solution (pH 4.0).

The fraction containing the antibody was subjected to buffer replacement with PBS by dialysis (Slide-A-Lyzer Dialysis Cassette, Thermo Scientific), diluted 5-fold with a 5 mM sodium phosphate/50-mM MES/pH 7.0 buffer, and applied to a ceramic hydroxyapatite column (Japan Bio-Rad Laboratories, Inc., Bio-Scale CHT Type-1 Hydroxyapatite Column) equilibrated with a 5-mM NaPi/50-mM MES/30 mM NaCl/pH 7.0 buffer.

Linear concentration gradient elution with sodium chloride was performed, and a fraction containing the antibody was collected. The fraction was subjected to buffer replacement with HBSor (25 mM histidine/5% sorbitol, pH 6.0) by dialysis (Slide-A-Lyzer Dialysis Cassette, Thermo Scientific). The antibody was concentrated with a Centrifugal UF Filter Device, VIVASPIN20 (fraction molecular weight UF10K, Sartorius AG), to prepare the IgG at a concentration of 50 mg/mL. Finally, filtration was carried out with a Minisart-Plus filter (Sartorius AG), to give a purified sample.

Example 7

In Vitro Activity of Humanized Anti-Human TLR7 Antibody

7)-1 Inhibitory Activity of Humanized Anti-Human TLR7 Antibody on Cytokine Production Human PBMCs were purchased from Cellular Technology Limited as a frozen product and thawed according to the instructions for use.

The PBMCs suspended at a concentration of $2.5\times10^6$ cells/mL in RPMI1640 (Life Technologies Corp.) containing 10% FBS, 1 mM Sodium Pyruvate (Life Technologies Corp.), 0.1 mM MEM Non-Essential Amino Acids (Life Technologies Corp.), 50 μM 2-Mercaptoethanol (Life Technologies Corp.), 50 U/mL Penicillin, and 50-μg/mL Streptomycin (Life Technologies Corp.) were seeded in a 96-well cell culture plate at 100 μL each, and the humanized anti-human TLR7 antibody, huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, or huNB7_H3L3_IgG4Pro, or a human IgG control antibody (Eureka Therapeutics) was added thereto at 80 μL/well, followed by pretreatment in an incubator at 37° C. for 4 hours.

Thereafter, 1 mg/mL CL-264 (InvivoGen) was added thereto at 20 μL/well, and the mixture was stirred well, followed by culturing at 37° C. for about 20 hours under 5% $CO_2$.

The plate was stirred well and thereafter centrifuged at 1500 rpm for 5 minutes, and the concentration of IL-6 contained in the supernatant was measured by the FRET method (Cisbio Bioassay. Inc).

Figure 23:
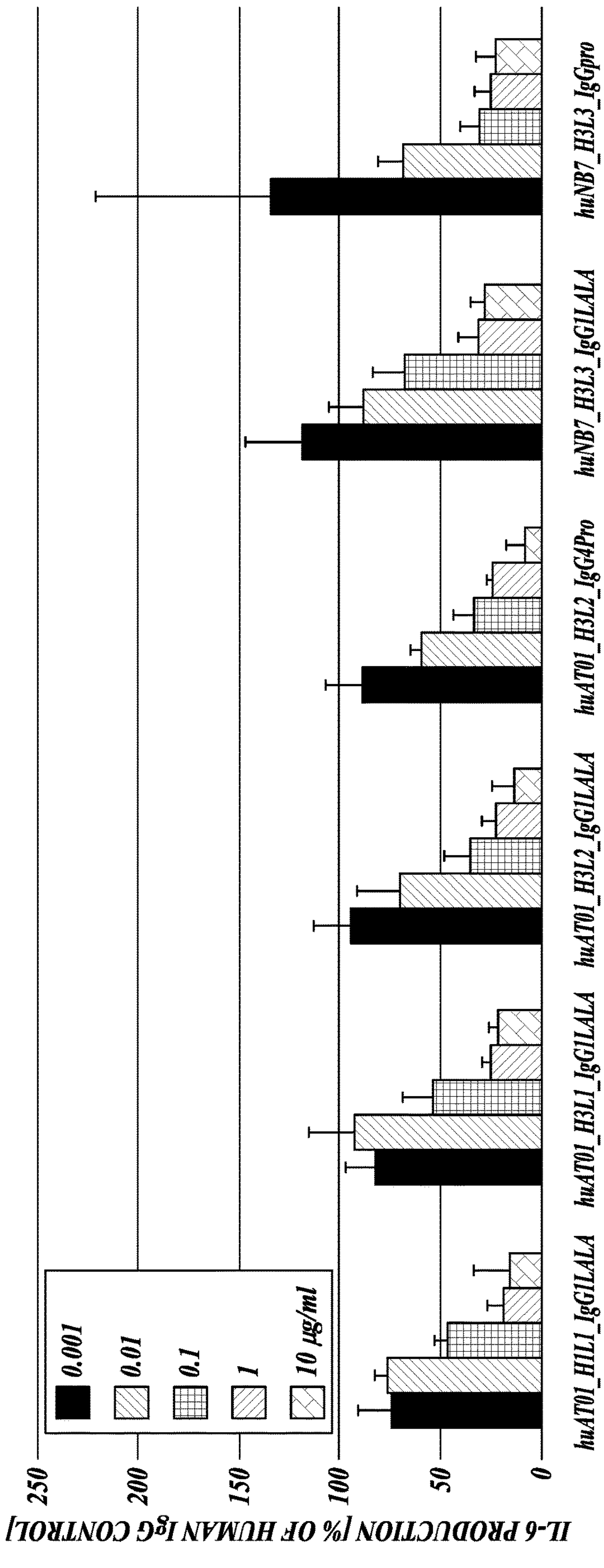
FIG. 23 is a graph showing that humanized anti-human TLR7 antibodies (huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro) suppress the production of IL-6 from human PBMCs treated with CL-264 in a concentration dependent manner.
Figure 25:
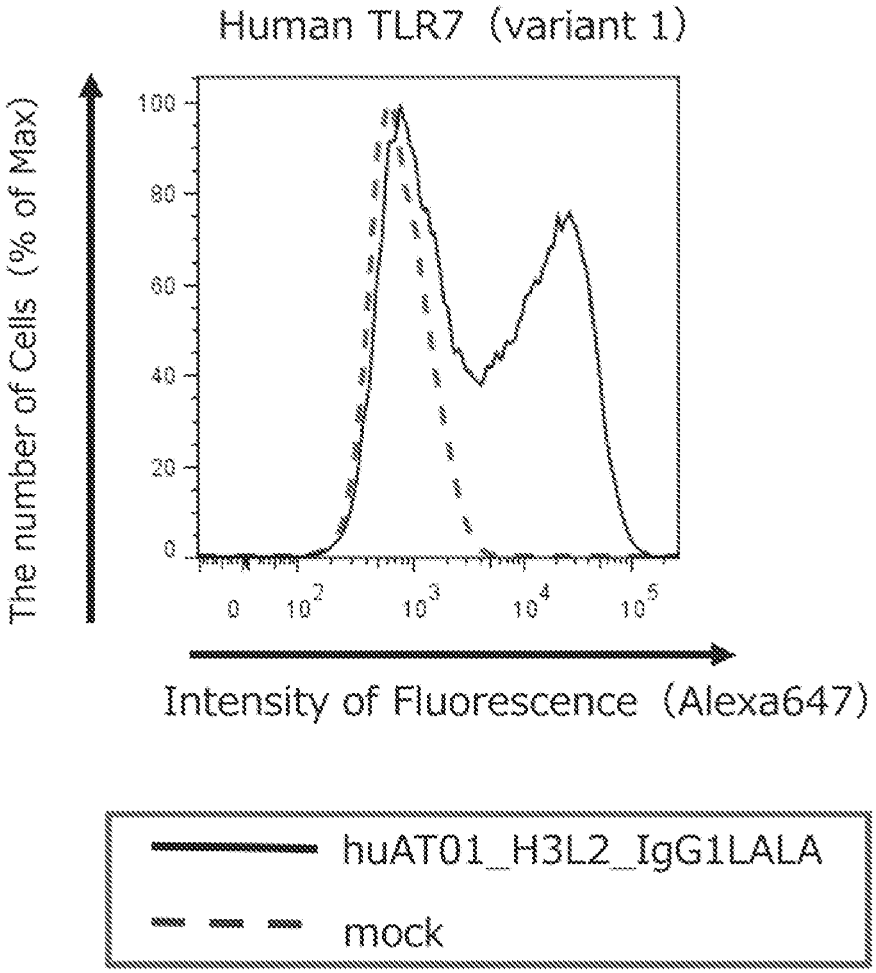
FIG. 25 shows the results of a flow cytometry analysis on binding to an antigen (human TLR7: variant 1) of humanized anti-human TLR7 antibody (huAT01_H3L2_IgG1LALA) and is a graph showing specific binding to the antigen.
Figure 26:
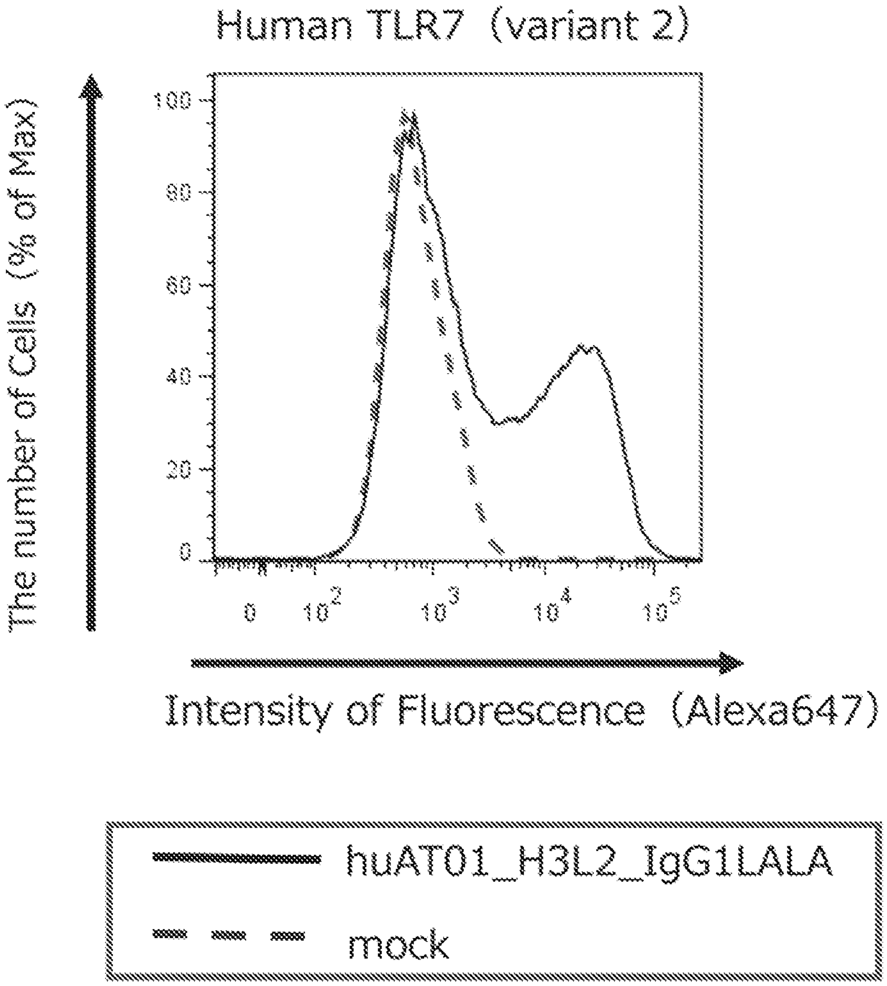
FIG. 26 shows the results of a flow cytometry analysis on binding to an antigen (human TLR7: variant 2) of humanized anti-human TLR7 antibody (huAT01_H3L2_IgG1LALA) and is a graph showing specific binding to the antigen.
Figure 27:
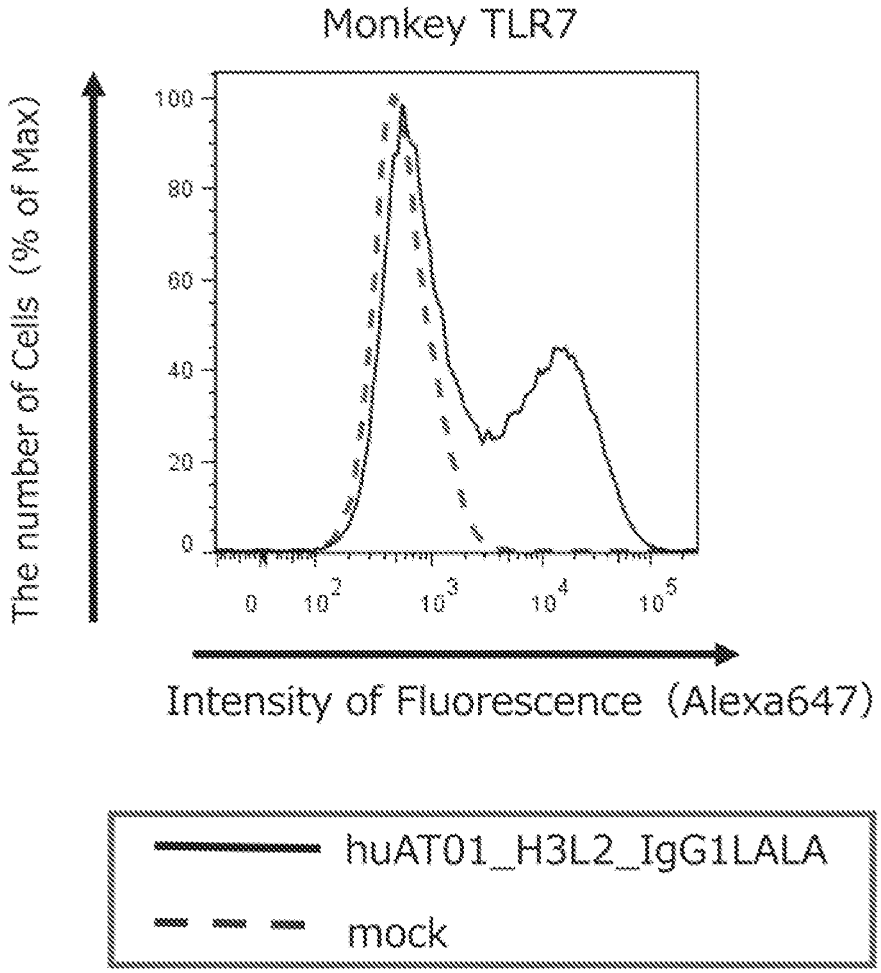
FIG. 27 shows the results of a flow cytometry analysis on binding to an antigen (monkey TLR7) of humanized anti-human TLR7 antibody (huAT01_H3L2_IgG1LALA) and is a graph showing specific binding to the antigen.
Figure 28:
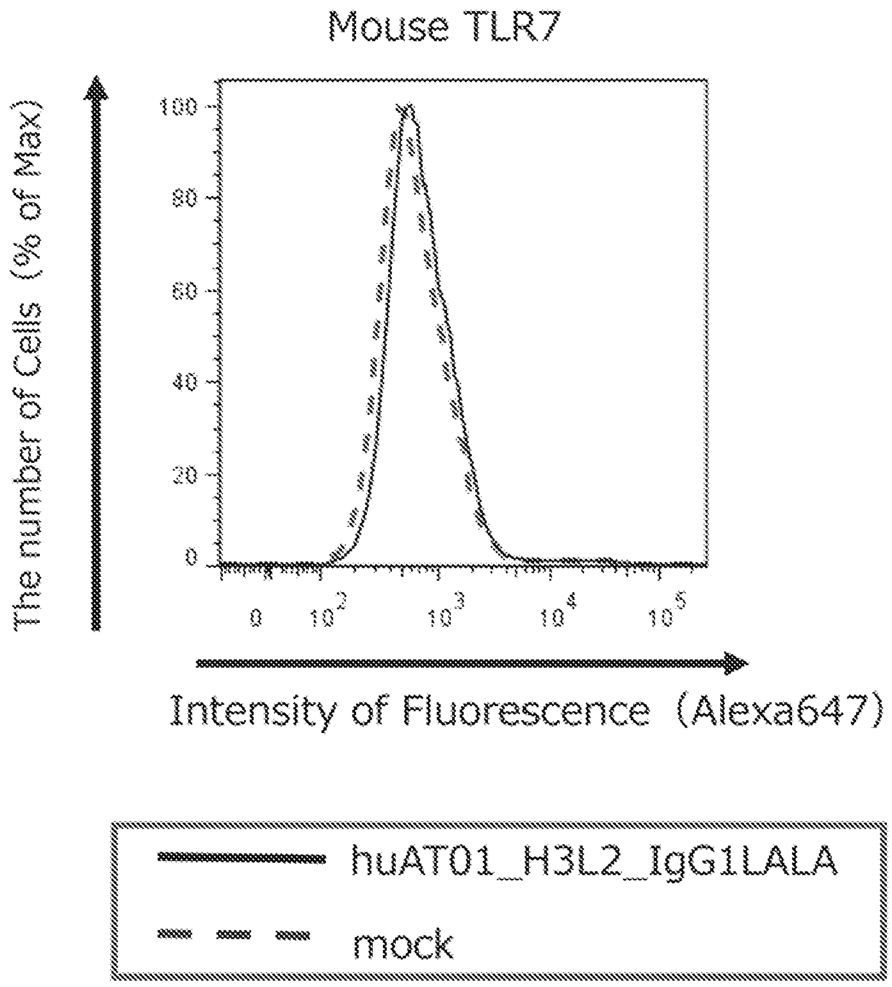
FIG. 28 shows the results of a flow cytometry analysis on binding to an antigen (mouse TLR7) of humanized anti-human TLR7 antibody (huAT01_H3L2_IgG1LALA) and is a graph showing non-binding to the antigen.
Figure 29:
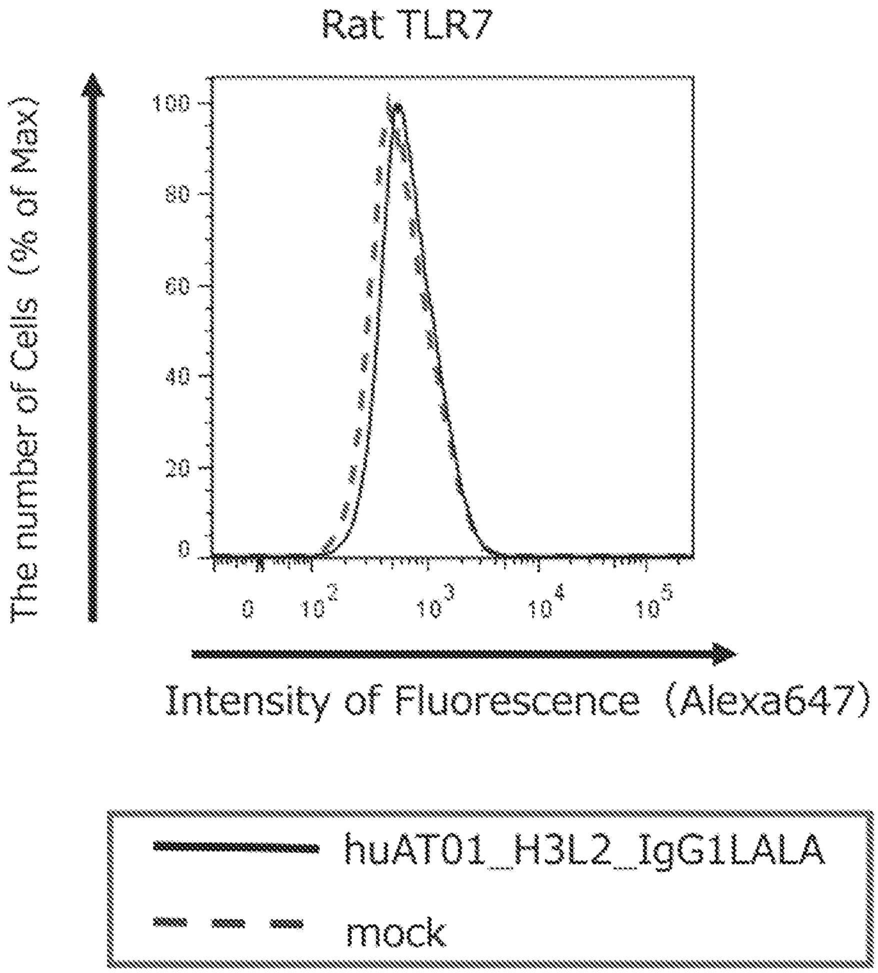
FIG. 29 shows the results of a flow cytometry analysis on binding to an antigen (rat TLR7) of humanized anti-human TLR7 antibody (huAT01_H3L2_IgG1LALA) and is a graph showing non-binding to the antigen.

FIG. 23 shows that the humanized anti-human TLR7 antibody suppresses the production of IL-6 from the human PBMCs treated with CL-264 in a concentration dependent manner.

The antibodies huAT01_H1L1_IgG1LALA, huAT01_H3L1_IgG1LALA, huAT01_H3L2_IgG1LALA, huAT01_H3L2_IgG4Pro, huNB7_H3L3_IgG1LALA, and huNB7_H3L3_IgG4Pro inhibited the production of IL-6 from the human PBMCs in a concentration dependent manner.

The half-inhibitory concentrations (IC50 of the antibodies huAT01_H1L1_IgG1LALA, huAT01_H3L1_IgG1LALA, huAT01_H3L2_IgG1LALA, huAT01_H3L2_IgG4Pro, huNB7_H3L3_IgG1LALA and huNB7_H3L3_IgG4Pro were 74 ng/mL, 138 ng/mL, 38 ng/mL, 24 ng/mL, 307 ng/mL and 31 ng/mL, respectively, which were calculated from the concentrations of the two values, which are either side of the 50% inhibitory activity, and the inhibitory activity when each of the two concentrations were added.

Example 8

Confirmation of Antigen Binding to Humanized Anti-Human TLR7 Antibody

8)-1 Preparation of HEK293 Cells Expressing Human TLR7 (Variant 1)-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50 μg/mL Streptomycin (Life Technologies Corp.) under conditions of 37° C. and 5% $CO_2$.

On the next day, plasmids expressing pcDNA3.1-human TLR7 (variant 1)-Flag, produced by GenScript Corporation, were transfected into LENTI-X® HEK293 T cells (Clontech Laboratories, Inc.) using a transfection reagent, LIPOFECTAMINE 2000 (Life Technologies Corp.), and the cells were further cultured overnight under conditions of 37° C. and 5% $CO_2$.

On the next day, the expression plasmid-introduced cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that human TLR7 was expressed in the cells transfected with the plasmids expressing pcDNA3.1-human TLR7 (variant 1)-Flag, by flow cytometry (Miltenyi Biotec K.K.) using an anti-Flag-PE antibody (BioLegend, Inc.) or an isotype control antibody (BioLegend, Inc.) as a negative control.

The amino acid sequence of human TLR7 (variant 1) and a polynucleotide sequence encoding the amino acid sequence are set forth in SEQ ID NOs: 2 and 1 in the Sequence Listing, respectively.

8)-2 Preparation of HEK293 Cells Forcibly Expressing Human TLR7 (Variant 2)-Flag LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-human TLR7 (variant 2)-Flag, produced by GenScript Biotech Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that human TLR7 was expressed in the cells transfected with the plasmids expressing pcDNA3.1-human TLR7 (variant 2)-Flag, by flow cytometry (Miltenyi Biotec K.K.) using an anti-Flag-PE antibody (BioLegend, Inc.) or an isotype control antibody (BioLegend, Inc.) as a negative control.

8)-3 Preparation of HEK293 Cells Expressing Monkey TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-monkey TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that monkey TLR7 was expressed in the cells transfected with the plasmids expressing pcDNA3.1-monkey TLR7-Flag, by flow cytometry (Miltenyi Biotec K.K.), using an anti-Flag-PE antibody (BioLegend, Inc.) or an isotype control antibody (BioLegend, Inc.) as a negative control.

8)-4 Preparation of HEK293 Cells Expressing Mouse TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50-U/mL Penicillin, and 50-μg/mL Streptomycin (Life Technologies Corp.) under conditions of 37° C. and 5% $CO_2$.

On the next day, plasmids expressing pcDNA3.1-mouse TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that mouse TLR7 was expressed in the cells transfected with the plasmids expressing pcDNA3.1-mouse TLR7-Flag by flow cytometry (Miltenyi Biotec K.K.), using an anti-Flag-PE antibody (BioLegend, Inc.) or an isotype control antibody (BioLegend, Inc.) as a negative control.

8)-5 Preparation of HEK293 Cells Expressing Rat TLR7-Flag

LENTI-X® HEK293 T cells (Clontech Laboratories, Inc.) at a concentration of $4.5\times10^6$ cells/flask were seeded in a 75-$cm^2$ flask (Sumitomo Bakelite Co., Ltd.) and cultured overnight in a DMEM medium (FUJIFILM Wako Pure Chemical Corporation) containing 10% FBS, 50 U/mL Penicillin, and 50-μg/mL Streptomycin (Life Technologies Corp.) under conditions of 37° C. and 5% $CO_2$.

On the next day, plasmids expressing pcDNA3.1-rat TLR7-Flag, produced by GenScript Corporation, were transfected into LENTI-X® HEK293 T cells (Clontech Laboratories, Inc.) using a transfection reagent, LIPOFECTAMINE® 2000 (Life Technologies Corp.), and the cells were further cultured overnight under conditions of 37° C. and 5% $CO_2$.

On the next day, the expression vector-transfected cells were treated with TrypLE Express (Life Technologies Corporation), and the cells after the treatment were washed with a Flow Cytometry Staining Buffer (Life Technologies Corporation) and thereafter suspended in a Flow Cytometry Staining Buffer (Life Technologies Corporation). The cell suspension obtained was used in flow cytometry analysis.

It was confirmed that rat TLR7 was expressed in the cells transfected with the plasmids expressing pcDNA3.1-rat TLR7-Flag by flow cytometry (Miltenyi Biotec K.K.), using an anti-Flag-PE antibody (BioLegend, Inc.) or an isotype control antibody (BioLegend, Inc.) as a negative control.

8)-6 Evaluation of Binding Selectivity of Humanized Anti-Human TLR7 Antibody by Flow Cytometry The HEK293 cells expressing human TLR7 (variant 1)-Flag prepared in 8)-1, the HEK293 cells expressing human TLR7 (variant 2)-Flag prepared in 8)-2, the HEK293 cells expressing monkey TLR7-Flag prepared in 8)-3, the HEK293 cells expressing mouse TLR7-Flag prepared in 8)-4, and the HEK293 cells expressing rat TLR7-Flag prepared in 8)-5 were immobilized/subjected to membrane permeation with a Fixation and Permeabilization Solution (Becton, Dickinson and Company) and thereafter stained using huAT01_H3L2_IgG1LALA, which is one of the humanized anti-human TLR7 antibodies, and ALEXA FLUOR® 647 AffiniPure Goat anti-human IgG+IgM (H+L) (Jackson ImmunoResearch Inc.), which is the secondary antibody.

The binding of the humanized anti-human TLR7 antibody to human TLR7 was detected based on flow cytometry (Miltenyi Biotec K.K.), and the data was analyzed using software (Flowjo) which analyzes the data of flow cytometry.

The results indicate that huAT01_H3L2_IgG1LALA, which is one of the humanized anti-human TLR7 antibodies, bound specifically to human TLR7 (variant 1), human TLR7 (variant 2), or monkey TLR7, and did not bind to mouse TLR7 or rat TLR7. FIGS. 25 to 29 show the results.

Example 9 Evaluation of In Vivo Inhibitory Effects of Anti-Human TLR7 Antibody 9-1) Establishment of Human TLR7 Transgenic/Mouse TLR7 Knockout Mice 9-1-1) Preparation of Human TLR7 Transgenic Mouse ROSA26 locus was targeted in murine embryonic stem (ES) cells to generate human TLR7 transgenic mice.

Namely, human TLR7 plasmids were produced by incorporating human TLR7 gene (SEQ ID NO:3) into CTV (CAG-STOP-eGFP-ROSA26TV) plasmid (Addgene) by using GIBSON ASSEMBLY® systems (New England BioLabs Inc.).

Next, the human TLR7 plasmids produced above were introduced into JM8. A3 (KOMP), which is ES cells derived from C57BL/6N mice, by electroporation.

The ES cells in which human TLR7 plasmids were introduced were then selected by using neomycin.

From ES cell clones resistant to neomycin, clones in which homologous recombination occurred were selected by Southern blotting.

The selected ES cell clones were injected into mouse embryos derived from C57BL/6N mice (Japan SLC, Inc.) and the said embryos were transplanted into C57BL/6N mice (Japan SLC, Inc.) which were foster parent mice, and chimeric mice were produced.

9-1-2) Preparation of Mouse TLR7 Knockout Mice

Mouse TLR7 knockout mice were generated by using known genetic modification techniques.

That is, a guide RNA (gaacaguuggccaaucucucagg: SEQ ID NO: 87) targeting the sequence on exon 5 of the mouse TLR7 gene (SEQ ID NO:56) and a hCas9 protein (S.p. Cas9 Nuclease V3:IDT) were injected into fertilized eggs obtained from pregnant mice by mating C57BL/6N mice (Japan SLC, Inc.) to perform gene editing for deleting 4 bases on exon 5 of the mouse TLR7 gene.

Subsequently, the said fertilized eggs were transplanted into C57BL/6N mice (Japan SLC, Inc.) which were foster parent mice.

DNA was extracted from the tail of the offspring of the foster parent mice, and the said offspring of the foster parent mice was genotyped by the PCR method, and consequently the individual in which 4 bases on exon 5 of the mouse TLR7 gene were deleted, was recognized.

The said individual was confirmed to be a mouse TLR7 knockout mouse without expressing normal mouse TLR7 protein by frameshift.

9-1-3) Mating of Human TLR7 Transgenic Mice and Mouse TLR7 Knockout Mice

Human TLR7 transgenic mice produced in 9-1-1) and mouse TLR7 knockout mice produced in 9-1-2) were mated, and human TLR7 transgenic/mouse TLR7 knockout mice were established.

9-2) Evaluation of Inhibitory Effects of Anti-Human TLR7 Antibody Using Human TLR7 Transgenic/Mouse TLR7 Knockout Mice 9-2-1) Antibody Administration, R848 Administration, and Blood Sampling Human TLR7 transgenic/mouse TLR7 knockout mice established in 9-1-3) were administered 500 μg of a control antibody that does not bind human TLR7 or a humanized anti-human TLR7 antibody (huAT01_H3L2_IgG1LALA) obtained in Example 6)-3-7 intraperitoneally.

Seven days after the administration of the said antibodies, 20 μg of R848 (InvivoGen), which is a ligand of TLR7 was administered intraperitoneally for activating TLR7 function.

Blood was collected from mice of each treatment group after 6 hours from R848 administration.

After blood collection, centrifugation was performed at 10,000 rpm for 15 minutes, and sera were collected.

9-2-2) Measurement of IL-6 Production Using Sera

Amount of IL-6 production was measured by ELISA kits (Thermo Fisher Scientific) using sera collected in 9-2-1).

Figure 30:
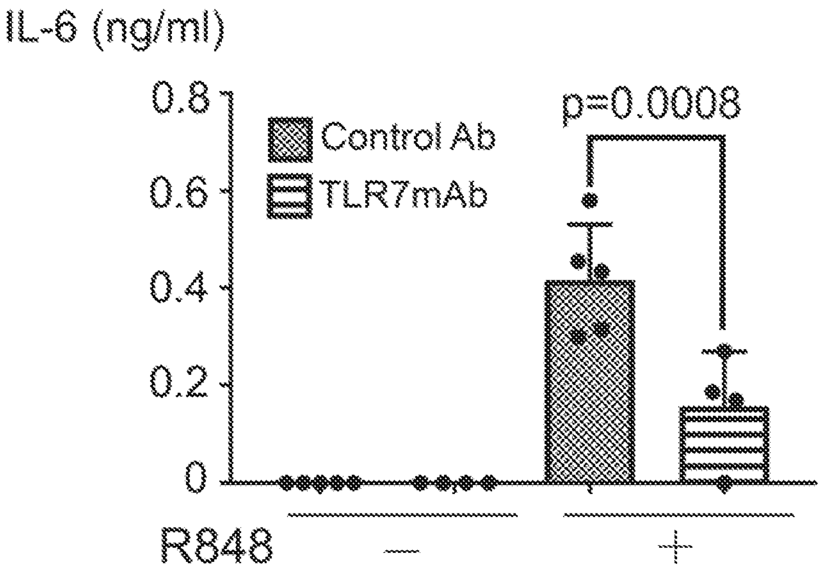
FIG. 30 shows the results of evaluation of in vivo inhibitory effects of anti-human TLR7 antibody using human TLR7 transgenic/mouse TLR7 knockout mice. Amount of IL-6 production was measured by ELISA kits using sera collected from mice treated with the control antibody or the humanized anti-human TLR7 antibody (huAT01_H3L2_IgG1LALA) and then with a ligand of TLR7 (R848).

The result is shown in FIG. 30.

Compared with the group of mice treated with the control antibody, the group of mice treated with the humanized anti-human TLR7 antibody significantly reduced the amount of IL-6 production ($p=0.0008$).

INDUSTRIAL APPLICABILITY

The humanized anti-TLR7 antibody of the present invention has a human TLR7 function-inhibitory activity-suppressing action and thus can be an agent for treating or preventing immune inflammation-related diseases and the like.

SEQUENCE LISTING

SEQ ID NO: 1: Nucleotide sequence encoding human TLR7 (variant 1)

SEQ ID NO: 2: Amino acid sequence of human TLR7 (variant 1)

SEQ ID NO: 3: Nucleotide sequence encoding human TLR7 (variant 2)

SEQ ID NO: 4: Amino acid sequence of human TLR7 (variant 2)

SEQ ID NO: 5: Amino acid sequence of heavy-chain variable region of AT01 antibody SEQ ID NO: 6: Nucleotide sequence encoding heavy-chain variable region of cAT01 antibody SEQ ID NO: 7: Amino acid sequence of heavy-chain variable region of NB7 antibody SEQ ID NO: 8: Nucleotide sequence encoding heavy-chain variable region of cNB7 antibody SEQ ID NO: 9: Amino acid sequence of heavy-chain variable region of FAN2 antibody SEQ ID NO: 10: Nucleotide sequence encoding heavy-chain variable region of cFAN2 antibody SEQ ID NO: 11: Amino acid sequence of light-chain variable region of AT01 antibody SEQ ID NO: 12: Nucleotide sequence encoding light-chain variable region of cAT01 antibody SEQ ID NO: 13: Amino acid sequence of light-chain variable region of NB7 antibody SEQ ID NO: 14: Nucleotide sequence encoding light-chain variable region of cNB7 antibody SEQ ID NO: 15: Amino acid sequence of light-chain variable region of FAN2 antibody SEQ ID NO: 16: Nucleotide sequence encoding light-chain variable region of cFAN2 antibody SEQ ID NO: 17: Amino acid sequence of CDRH1 of AT01 antibody SEQ ID NO: 18: Amino acid sequence of CDRH2 of AT01 antibody
SEQ ID NO: 19: Amino acid sequence of CDRH3 of AT01 antibody
SEQ ID NO: 20: Amino acid sequence of CDRL1 of AT01 antibody
SEQ ID NO: 21: Amino acid sequence of CDRL2 of AT01 antibody
SEQ ID NO: 22: Amino acid sequence of CDRL3 of AT01 antibody
SEQ ID NO: 23: Amino acid sequence of CDRH1 of NB7 antibody
SEQ ID NO: 24: Amino acid sequence of CDRH2 of NB7 antibody
SEQ ID NO: 25: Amino acid sequence of CDRH3 of NB7 antibody
SEQ ID NO: 26: Amino acid sequence of CDRL1 of NB7 antibody
SEQ ID NO: 27: Amino acid sequence of CDRL2 of NB7 antibody
SEQ ID NO: 28: Amino acid sequence of CDRL3 of NB7 antibody
SEQ ID NO: 29: Amino acid sequence of CDRH1 of FAN2 antibody
SEQ ID NO: 30: Amino acid sequence of CDRH2 of FAN2 antibody
SEQ ID NO: 31: Amino acid sequence of CDRH3 of FAN2 antibody
SEQ ID NO: 32: Amino acid sequence of CDRL1 of FAN2 antibody
SEQ ID NO: 33: Amino acid sequence of CDRL2 of FAN2 antibody
SEQ ID NO: 34: Amino acid sequence of CDRL3 of FAN2 antibody
SEQ ID NO: 35: Amino acid sequence of heavy chain of AT01 chimeric anti-human TLR7 antibody (cAT01)
SEQ ID NO: 36: Amino acid sequence of light chain of AT01 chimeric anti-human TLR7 antibody (cAT01)
SEQ ID NO: 37: Amino acid sequence of heavy chain of NB7 chimeric anti-human TLR7 antibody (cNB7)
SEQ ID NO: 38: Amino acid sequence of light chain of NB7 chimeric anti-human TLR7 antibody (cNB7)
SEQ ID NO: 39: Amino acid sequence of heavy chain of FAN2 chimeric anti-human TLR7 antibody (cFAN2)
SEQ ID NO: 40: Amino acid sequence of light chain of FAN2 chimeric anti-human TLR7 antibody (cFAN2)
SEQ ID NO: 41: Amino acid sequence of heavy-chain variable region of huAT01_H1_IgG1LALA
SEQ ID NO: 42: Amino acid sequence of heavy-chain variable region of huAT01_H3_IgG1LALA
SEQ ID NO: 43: Amino acid sequence of light-chain variable region of huAT01_L1
SEQ ID NO: 44: Amino acid sequence of light-chain variable region of huAT01_L2
SEQ ID NO: 45: Amino acid sequence of huAT01_H1_IgG1LALA
SEQ ID NO: 46: Amino acid sequence of huAT01_H3_IgG1LALA
SEQ ID NO: 47: Amino acid sequence of huAT01_H3_IgG4Pro
SEQ ID NO: 48: Amino acid sequence of huAT01_L1
SEQ ID NO: 49: Amino acid sequence of huAT01_L2
SEQ ID NO: 50: Amino acid sequence of heavy-chain variable region of huNB7_H3_IgG1LALA
SEQ ID NO: 51: Amino acid sequence of light-chain variable region of huNB7_L3
SEQ ID NO: 52: Amino acid sequence of huNB7_H3_IgG1LALA
SEQ ID NO: 53: Amino acid sequence of huNB7_L3
SEQ ID NO: 54: Amino acid sequence of huNB7_H3_IgG4Pro
SEQ ID NO: 55: Nucleotide sequence of human Unc93B1 gene
SEQ ID NO: 56: Nucleotide sequence of mouse TLR7 gene
SEQ ID NO: 57: Nucleotide sequence of rat TLR7 gene
SEQ ID NO: 58: Nucleotide sequence of monkey TLR7 gene
SEQ ID NO: 59: Nucleotide sequences of DNA fragments comprising nucleotide sequences encoding human light-chain signal sequence and human kappa-chain constant region
SEQ ID NO: 60: Nucleotide sequences of DNA fragments comprising nucleotide sequences encoding human heavy-chain signal sequence and human IgG1 constant region
SEQ ID NO: 61: Nucleotide sequence encoding heavy chain of cAT01 antibody
SEQ ID NO: 62: Nucleotide sequence of DNA fragment comprising nucleotide sequence encoding light chain of cAT01 antibody
SEQ ID NO: 63: Nucleotide sequence encoding heavy chain of cNB7 antibody
SEQ ID NO: 64: Nucleotide sequence of DNA fragment comprising nucleotide sequence encoding light chain of cNB7 antibody
SEQ ID NO: 65: Nucleotide sequence encoding heavy chain of cFAN2 antibody
SEQ ID NO: 66: Nucleotide sequence of DNA fragment comprising nucleotide sequence encoding cFAN2 antibody light chain
SEQ ID NO: 67: Nucleotide sequence encoding huAT01_H1_IgG1LALA
SEQ ID NO: 68: Nucleotide sequence encoding huAT01_H3_IgG1LALA
SEQ ID NO: 69: Nucleotide sequence encoding huAT01_H3_IgG4Pro
SEQ ID NO: 70: Nucleotide sequence encoding huAT01_L1
SEQ ID NO: 71: Nucleotide sequence encoding huAT01_L2
SEQ ID NO: 72: Nucleotide sequence encoding huNB7_H3_IgG1LALA
SEQ ID NO: 73: Nucleotide sequence encoding huNB7_H3_IgG4Pro
SEQ ID NO: 74: Nucleotide sequence encoding huNB7_L3
SEQ ID NO: 75: Nucleotide sequences of DNA fragments comprising nucleotide sequences encoding human heavy-chain signal sequence and human IgG1LALA constant region
SEQ ID NO: 76: Nucleotide sequences of DNA fragments comprising nucleotide sequences encoding human heavy-chain signal sequence and human IgG4Pro constant region
SEQ ID NO: 77: Nucleotide sequence encoding heavy-chain variable region of huAT01_H1
SEQ ID NO: 78: Nucleotide sequence encoding heavy-chain variable region of huAT01_H3
SEQ ID NO: 79: Nucleotide sequence encoding light-chain variable region of huAT01_L1
SEQ ID NO: 80: Nucleotide sequence encoding light-chain variable region of huAT01_L2
SEQ ID NO: 81: Nucleotide sequence encoding heavy-chain variable region of huNB7_H3
SEQ ID NO: 82: Nucleotide sequence encoding light-chain variable region of huNB7_L3
SEQ ID NO: 83: Amino acid sequence of mouse TLR7
SEQ ID NO: 84: Amino acid sequence of rat TLR7
SEQ ID NO: 85: Amino acid sequence of monkey TLR7
SEQ ID NO: 86: Nucleotide sequence of human Unc93B1 D34A mutant-HAX2 gene
SEQ ID NO: 87: guide RNA targeting the sequence on exon 5 of the mouse TLR7 gene

The invention claimed is:

1. A polynucleotide comprising a polynucleotide sequence encoding an antibody or an antigen-binding fragment of the antibody, wherein the antibody or an antigen-binding fragment of the antibody having the properties of:

(a) specifically binding to human TLR7 or monkey TLR7 and not binding to mouse TLR7 or rat TLR7;

(b) inhibiting a function of human TLR7 or monkey TLR7; and (c) comprising CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

2. The polynucleotide comprising a polynucleotide sequence encoding the antibody or the antigen-binding fragment of the antibody according to claim 1, wherein the human TLR7 is a molecule consisting of the amino acid sequence set forth in SEQ ID NO: 2 or SEQ ID NO: 4, the monkey TLR7 is a molecule consisting of the amino acid sequence set forth in SEQ ID NO: 85, the mouse TLR7 is a molecule consisting of the amino acid sequence set forth in SEQ ID NO: 83, or the rat TLR7 is a molecule consisting of the amino acid sequence set forth in SEQ ID NO: 84.

3. The polynucleotide comprising a polynucleotide sequence encoding the antibody or the antigen-binding fragment of the antibody according to claim 1, wherein the antibody or the antigen-binding fragment of the antibody comprising: a heavy-chain variable region consisting of the amino acid sequence set forth in SEQ ID NO: 5 and a light-chain variable region consisting of the amino acid sequence set forth in SEQ ID NO: 11.

4. The polynucleotide comprising a polynucleotide sequence encoding the antibody or the antigen-binding fragment of the antibody according to claim 1, wherein a constant region is a human-derived constant region.

5. The polynucleotide comprising a polynucleotide sequence encoding the antibody or the antigen-binding fragment of the antibody according to claim 4, comprising: a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36.

6. The polynucleotide comprising a polynucleotide sequence encoding the antibody or the antigen-binding fragment of the antibody according to claim 1, wherein the antibody or the antigen-binding fragment of the antibody is humanized.

7. The polynucleotide comprising a polynucleotide sequence encoding the antibody or the antigen-binding fragment of the antibody according to claim 6, comprising:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43; or (d) a heavy-chain variable region consisting of the amino acid sequence set forth in SEQ ID NO: 42 and a light-chain variable region consisting of the amino acid sequence set forth in SEQ ID NO: 44.

8. The polynucleotide comprising a polynucleotide sequence encoding the antibody or the antigen-binding fragment of the antibody according to claim 7, comprising a heavy-chain variable region consisting of the amino acid sequence set forth in SEQ ID NO: 42 and a light-chain variable region consisting of the amino acid sequence set forth in SEQ ID NO: 44.

9. The polynucleotide comprising a polynucleotide sequence encoding the antibody or the antigen-binding fragment of the antibody according to claim 7, comprising:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48; or (f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

10. The polynucleotide comprising a polynucleotide sequence encoding the antibody or the antigen-binding fragment of the antibody according to claim 9, comprising a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

11. The polynucleotide comprising a polynucleotide sequence encoding the antibody or the antigen-binding fragment of the antibody according to claim 1, wherein the antigen-binding fragment is selected from the group consisting of Fab, $F(ab)_2$, Fab' and Fv.

12. A polynucleotide comprising a polynucleotide sequence encoding an antibody or an antigen-binding fragment of the antibody, wherein the antibody or an antigen-binding fragment of the antibody having the properties of:

(a) specifically binding to human TLR7, (b) inhibiting a function of human TLR7, and (c) comprising CDRH1 consisting of the amino acid sequence set forth in SEQ ID NO: 17, CDRH2 consisting of the amino acid sequence set forth in SEQ ID NO: 18 and CDRH3 consisting of the amino acid sequence set forth in SEQ ID NO: 19, as complementarity determining regions in the heavy chain, and CDRL1 consisting of the amino acid sequence set forth in SEQ ID NO: 20, CDRL2 consisting of the amino acid sequence set forth in SEQ ID NO: 21 and CDRL3 consisting of the amino acid sequence set forth in SEQ ID NO: 22, as complementarity determining regions in the light chain.

13. The polynucleotide comprising the polynucleotide sequence encoding the antibody or the antigen-binding fragment of the antibody according to claim 12, wherein the antibody or the antigen-binding fragment of the antibody comprises a heavy-chain variable region consisting of the amino acid sequence set forth in SEQ ID NO: 5 and a light-chain variable region consisting of the amino acid sequence set forth in SEQ ID NO: 11.

14. The polynucleotide comprising the polynucleotide sequence encoding the antibody or the antigen-binding fragment of the antibody according to claim 12, wherein a constant region is a human-derived constant region.

15. The polynucleotide comprising the polynucleotide sequence encoding the antibody or the antigen-binding fragment of the antibody according to claim 14, wherein the antibody or the antigen-binding fragment of the antibody comprises a heavy chain consisting of an amino acid sequence at positions 20 to 465 in the amino acid sequence set forth in SEQ ID NO: 35 and a light chain consisting of an amino acid sequence at positions 21 to 233 in the amino acid sequence set forth in SEQ ID NO: 36.

16. The polynucleotide comprising the polynucleotide sequence encoding the antibody or the antigen-binding fragment of the antibody according to claim 12, wherein the antibody or the antigen-binding fragment of the antibody is humanized.

17. The polynucleotide comprising the polynucleotide sequence encoding the antibody or the antigen-binding fragment of the antibody according to claim 16, wherein the antibody or the antigen-binding fragment of the antibody comprises:

(a) a heavy-chain variable region consisting of the amino acid sequence set forth in SEQ ID NO: 41 and a light-chain variable region consisting of the amino acid sequence set forth in SEQ ID NO: 43;

(b) a heavy-chain variable region consisting of the amino acid sequence set forth in SEQ ID NO: 41 and a light-chain variable region consisting of the amino acid sequence set forth in SEQ ID NO: 44;

(c) a heavy-chain variable region consisting of the amino acid sequence set forth in SEQ ID NO: 42 and a light-chain variable region consisting of the amino acid sequence set forth in SEQ ID NO: 43; or (d) a heavy-chain variable region consisting of the amino acid sequence set forth in SEQ ID NO: 42 and a light-chain variable region consisting of the amino acid sequence set forth in SEQ ID NO: 44.

18. The polynucleotide comprising the polynucleotide sequence encoding the antibody or the antigen-binding fragment of the antibody according to claim 17, wherein the antibody or the antigen-binding fragment of the antibody comprises a heavy-chain variable region consisting of the amino acid sequence set forth in SEQ ID NO: 42 and a light-chain variable region consisting of the amino acid sequence set forth in SEQ ID NO: 44.

19. The polynucleotide comprising the polynucleotide sequence encoding the antibody or the antigen-binding fragment of the antibody according to claim 17, wherein the antibody or the antigen-binding fragment of the antibody comprises:

(a) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 48;

(b) a heavy chain consisting of an amino acid sequence at positions 20 to 465 in the amino acid sequence set forth in SEQ ID NO: 45 and a light chain consisting of an amino acid sequence at positions 21 to 233 in the amino acid sequence set forth in SEQ ID NO: 49;

(c) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 48;

(d) a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49;

(e) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 48; or (f) a heavy chain consisting of an amino acid sequence at positions 20 to 462 in the amino acid sequence set forth in SEQ ID NO: 47 and a light chain consisting of an amino acid sequence at positions 21 to 233 in the amino acid sequence set forth in SEQ ID NO: 49.

20. A polynucleotide comprising a polynucleotide sequence encoding an antibody or an antigen-binding fragment of the antibody, wherein the antibody or the antigen-binding fragment of the antibody comprises a heavy chain consisting of an amino acid sequence at positions 20 to 465 in the amino acid sequence set forth in SEQ ID NO: 46 and a light chain consisting of an amino acid sequence at positions 21 to 233 in the amino acid sequence set forth in SEQ ID NO: 49.

21. The polynucleotide comprising a polynucleotide sequence encoding an antibody or an antigen-binding fragment of the antibody according to claim 12, wherein the antigen-binding fragment of the antibody is selected from the group consisting of Fab, $F(ab)_2$, Fab' and Fv.

22. The polynucleotide comprising a polynucleotide sequence encoding an antibody or an antigen-binding fragment of the antibody according to claim 12, comprising:

a polynucleotide sequence selected from the group consisting of:

(a) a polynucleotide sequence encoding the heavy-chain variable region set forth in SEQ ID NO: 77;

(b) a polynucleotide sequence encoding the heavy-chain variable region set forth in SEQ ID NO: 78; and (c) a polynucleotide sequence of a polynucleotide which hybridizes with a polynucleotide consisting of a polynucleotide sequence complementary to the polynucleotide sequence (a) or (b) under stringent conditions; and a polynucleotide sequence selected from the group consisting of:

(d) a polynucleotide sequence encoding the light-chain variable region set forth in SEQ ID NO: 79;

(e) a polynucleotide sequence encoding the light-chain variable region set forth in SEQ ID NO: 80; and (f) a polynucleotide sequence of a polynucleotide which hybridizes with a polynucleotide consisting of a polynucleotide sequence complementary to the polynucleotide sequence (d) or (e) under stringent conditions.

23. The polynucleotide according to claim 22, comprising:

(a) a polynucleotide sequence encoding the heavy-chain variable region set forth in SEQ ID NO: 77 and a polynucleotide sequence encoding the light-chain variable region set forth in SEQ ID NO: 79;

(b) a polynucleotide sequence encoding the heavy-chain variable region set forth in SEQ ID NO: 77 and a polynucleotide sequence encoding the light-chain variable region set forth in SEQ ID NO: 80;

(c) a polynucleotide sequence encoding the heavy-chain variable region set forth in SEQ ID NO: 78 and a polynucleotide sequence encoding the light-chain variable region set forth in SEQ ID NO: 79; or (d) a polynucleotide sequence encoding the heavy-chain variable region set forth in SEQ ID NO: 78 and a polynucleotide sequence encoding the light-chain variable region set forth in SEQ ID NO: 80.

24. An expression vector comprising the polynucleotide according to claim 1.

25. A host cell transformed with the expression vector according to claim 24.

26. The host cell according to claim 25, wherein the host cell is a eukaryotic cell.

27. A method for producing an antibody or an antigen-binding fragment of the antibody, comprising the steps of:

culturing the host cell according to claim 25; and collecting the antibody or the fragment of interest from the culture obtained in the above step.

28. An expression vector comprising the polynucleotide according to claim 12.

29. A host cell transformed with the expression vector according to claim 28.

30. The host cell according to claim 29, wherein the host cell is a eukaryotic cell.

31. A method for producing an antibody or an antigen-binding fragment of the antibody, comprising the steps of:

culturing the host cell according to claim 29; and collecting the antibody or the fragment of interest from the culture obtained in the above step.

32. An expression vector comprising the polynucleotide according to claim 20.

33. A host cell transformed with the expression vector according to claim 32.

34. The host cell according to claim 33, wherein the host cell is a eukaryotic cell.

35. A method for producing an antibody or an antigen-binding fragment of the antibody, comprising the steps of:

culturing the host cell according to claim 33; and collecting the antibody or the fragment of interest from the culture obtained in the above step.

36. An expression vector comprising the polynucleotide according to claim 22.

37. A host cell transformed with the expression vector according to claim 36.

38. The host cell according to claim 37, wherein the host cell is a eukaryotic cell.

39. A method for producing an antibody or an antigen-binding fragment of the antibody, comprising the steps of:

culturing the host cell according to claim 37; and collecting the antibody or the fragment of interest from the culture obtained in the above step.

* * * * *